(12) United States Patent
Moon et al.

(10) Patent No.: US 7,843,567 B2
(45) Date of Patent: *Nov. 30, 2010

(54) METHODS OF IDENTIFYING AN ANALYTE AND NUCLEIC ACID ANALYSIS

(75) Inventors: John A. Moon, Wallingford, CT (US); Alan D. Kersey, South Glastonbury, CT (US); Martin A. Putnam, Cheshire, CT (US); Tuo Li, East Lyme, CT (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/644,255

(22) Filed: Dec. 22, 2009

(65) Prior Publication Data

US 2010/0099574 A1  Apr. 22, 2010

Related U.S. Application Data

(63) Continuation of application No. 11/607,837, filed on Nov. 30, 2006, now Pat. No. 7,659,983, which is a continuation of application No. 10/763,995, filed on Jan. 22, 2004, now Pat. No. 7,164,533, and a continuation-in-part of application No. 10/661,234, filed on Sep. 12, 2003, now Pat. No. 7,106,513, and a continuation-in-part of application No. 10/661,031, filed on Sep. 12, 2003, now Pat. No. 7,349,158, and a continuation-in-part of application No. 10/661,836, filed on Sep. 12, 2003, now Pat. No. 7,399,643.

(60) Provisional application No. 60/519,932, filed on Nov. 14, 2003, provisional application No. 60/441,678, filed on Jan. 22, 2003.

(51) Int. Cl.
*G01N 21/25* (2006.01)

(52) U.S. Cl. .................................. 356/417

(58) Field of Classification Search ................. 356/317, 356/417
See application file for complete search history.

(56) References Cited

U.S. PATENT DOCUMENTS 3,074,634 A  1/1963  Gamo (Continued)

FOREIGN PATENT DOCUMENTS

CH  598661  5/1978

(Continued)

OTHER PUBLICATIONS

Jain KK, Nanodiagnostics: Application of Nanotechnology in Molecular Diagnostics, Expert Review of Molecular Diagnostics 3(2):153-161 (2003), XP008038849.

(Continued)

*Primary Examiner*—Kara E Geisel
(74) *Attorney, Agent, or Firm*—The Small Patent Law Group; Dean D. Small; Jason P. Gross

(57) ABSTRACT

A method of identifying an analyte. The method includes providing a plurality of microparticles. The microparticles have optically detectable codes extending along bodies of the corresponding microparticle. The microparticles have the chemical probes attached thereto. Each of the chemical probes is associated with a corresponding one of the codes. The method also includes selectively binding target analytes to the chemical probes on the microparticles to produce labeled microparticles and distributing the labeled microparticles to random locations of a substrate. The method also includes determining the codes for the labeled microparticles in the random array and code positions of the codes in the random array. The method further includes detecting the label on the labeled microparticles in the random array and label positions of the labels in the random array. The method also includes using the code positions and the label positions to analyze the target analyte.

49 Claims, 26 Drawing Sheets

U.S. PATENT DOCUMENTS

| | | |
|---|---|---|
| 3,600,223 A | 8/1971 | Glick |
| 3,614,193 A | 10/1971 | Beiser |
| 3,660,233 A | 5/1972 | Dalke et al. |
| 3,791,788 A | 2/1974 | Taylor |
| 3,858,979 A | 1/1975 | Elbe |
| 3,880,497 A | 4/1975 | Bryngdahl |
| 3,891,302 A | 6/1975 | Dabby |
| 3,903,415 A | 9/1975 | Holzapfel |
| 3,916,182 A | 10/1975 | Dabby |
| 3,968,476 A | 7/1976 | McMahon |
| 4,011,435 A | 3/1977 | Phelps |
| 4,023,010 A | 5/1977 | Horst |
| 4,053,228 A | 10/1977 | Schiller |
| 4,053,433 A | 10/1977 | Lee |
| 4,131,337 A | 12/1978 | Moraw |
| 4,168,146 A | 9/1979 | Grubb |
| 4,301,139 A | 11/1981 | Feingers |
| 4,386,274 A | 5/1983 | Altshuler |
| 4,400,616 A | 8/1983 | Chevillat |
| 4,445,229 A | 4/1984 | Tasto |
| 4,447,546 A | 5/1984 | Hirschfeld |
| 4,537,504 A | 8/1985 | Baltes |
| 4,560,881 A | 12/1985 | Briggs |
| 4,562,157 A | 12/1985 | Lowe |
| 4,647,544 A | 3/1987 | Nicoli |
| 4,678,752 A | 7/1987 | Thorne |
| 4,685,480 A | 8/1987 | Eck |
| 4,688,240 A | 8/1987 | Hosemann |
| 4,690,907 A | 9/1987 | Hibino |
| 4,701,754 A | 10/1987 | Provonchee |
| 4,716,121 A | 12/1987 | Block |
| 4,725,110 A | 2/1988 | Glenn |
| 4,740,468 A | 4/1988 | Weng |
| 4,740,688 A | 4/1988 | Edwards |
| 4,748,110 A | 5/1988 | Paul |
| 4,762,420 A | 8/1988 | Bowley |
| 4,767,719 A | 8/1988 | Finlan |
| 4,770,295 A | 9/1988 | Carveth et al. |
| 4,807,950 A | 2/1989 | Glenn |
| 4,815,027 A | 3/1989 | Tokumitsu |
| 4,816,659 A | 3/1989 | Bianco |
| 4,822,746 A | 4/1989 | Walt |
| 4,841,140 A | 6/1989 | Sullivan |
| 4,843,631 A | 6/1989 | Steinpichler |
| 4,877,747 A | 10/1989 | Stewart |
| 4,880,752 A | 11/1989 | Keck |
| 4,882,288 A | 11/1989 | North |
| 4,921,805 A | 5/1990 | Gebeyehu |
| 4,931,384 A | 6/1990 | Layton |
| 4,937,048 A | 6/1990 | Sakai |
| 4,958,376 A | 9/1990 | Leib |
| 4,992,385 A | 2/1991 | Godfrey |
| 5,002,867 A | 3/1991 | Macevicz |
| 5,003,600 A | 3/1991 | Deason |
| RE33,581 E | 4/1991 | Nicoli |
| 5,028,545 A | 7/1991 | Soini |
| 5,030,558 A | 7/1991 | Litman |
| 5,033,826 A | 7/1991 | Kolner |
| 5,048,139 A | 9/1991 | Matsumi et al. |
| 5,065,008 A | 11/1991 | Hakamata |
| 5,067,155 A | 11/1991 | Bianco |
| 5,081,012 A | 1/1992 | Flanagan |
| 5,089,387 A | 2/1992 | Tsay |
| 5,090,807 A | 2/1992 | Tai |
| 5,091,636 A | 2/1992 | Takada |
| 5,095,194 A | 3/1992 | Barbanell |
| 5,100,238 A | 3/1992 | Nailor |
| 5,104,209 A | 4/1992 | Hill |
| 5,105,305 A | 4/1992 | Betzig |
| 5,114,864 A | 5/1992 | Walt |
| 5,115,121 A | 5/1992 | Bianco |
| 5,118,608 A | 6/1992 | Layton |
| 5,129,974 A | 7/1992 | Aurenius |
| 5,138,468 A | 8/1992 | Barbanell |
| 5,141,848 A | 8/1992 | Donovan |
| 5,143,853 A | 9/1992 | Walt |
| 5,144,461 A | 9/1992 | Horan |
| 5,160,701 A | 11/1992 | Brown, III |
| 5,166,813 A | 11/1992 | Metz |
| 5,192,980 A | 3/1993 | Dixon |
| 5,196,350 A | 3/1993 | Backman |
| 5,200,794 A | 4/1993 | Nishiguma |
| 5,218,594 A | 6/1993 | Tanno |
| 5,239,178 A | 8/1993 | Derndinger |
| 5,244,636 A | 9/1993 | Walt |
| 5,283,777 A | 2/1994 | Tanno |
| 5,291,006 A | 3/1994 | Nishiguma |
| 5,291,027 A | 3/1994 | Kita |
| 5,300,764 A | 4/1994 | Hoshino |
| 5,307,332 A | 4/1994 | Tinet |
| 5,310,686 A | 5/1994 | Sawyers |
| 5,329,352 A | 7/1994 | Jacobsen |
| 5,342,790 A | 8/1994 | Levine |
| 5,349,442 A | 9/1994 | Deason |
| 5,352,582 A | 10/1994 | Lichtenwalter |
| 5,364,797 A | 11/1994 | Olson |
| 5,367,588 A | 11/1994 | Hill |
| 5,372,783 A | 12/1994 | Lackie |
| 5,374,816 A | 12/1994 | Bianco |
| 5,374,818 A | 12/1994 | Bianco |
| 5,388,173 A | 2/1995 | Glenn |
| 5,394,234 A | 2/1995 | Bianco |
| 5,395,558 A | 3/1995 | Tsai |
| 5,410,147 A | 4/1995 | Riza |
| 5,426,297 A | 6/1995 | Dunphy |
| 5,432,329 A | 7/1995 | Colgate |
| 5,442,433 A | 8/1995 | Hoshino |
| 5,448,659 A | 9/1995 | Tsutsui |
| 5,451,528 A | 9/1995 | Raymoure |
| 5,455,178 A | 10/1995 | Fattinger |
| 5,461,475 A | 10/1995 | Lerner |
| 5,465,176 A | 11/1995 | Bianco |
| 5,468,649 A | 11/1995 | Shah |
| 5,472,515 A | 12/1995 | Roberts et al. |
| 5,506,674 A | 4/1996 | Inoue |
| 5,514,785 A | 5/1996 | Van Ness |
| 5,528,045 A | 6/1996 | Hoffman |
| 5,547,849 A | 8/1996 | Baer |
| 5,559,613 A | 9/1996 | Deveaud-Pledran |
| 5,585,639 A | 12/1996 | Dorsel |
| 5,587,832 A | 12/1996 | Krause |
| 5,607,188 A | 3/1997 | Bahns |
| 5,610,287 A | 3/1997 | Nikiforov |
| 5,620,853 A | 4/1997 | Smethers |
| 5,621,515 A | 4/1997 | Hoshino |
| 5,624,850 A | 4/1997 | Kumar |
| 5,625,472 A | 4/1997 | Mizrahi |
| 5,627,040 A | 5/1997 | Bierre |
| 5,627,663 A | 5/1997 | Horan |
| 5,633,724 A | 5/1997 | King |
| 5,633,975 A | 5/1997 | Gary |
| 5,663,790 A | 9/1997 | Ekstrom |
| 5,667,976 A | 9/1997 | Van Ness |
| 5,671,308 A | 9/1997 | Inoue |
| 5,682,244 A | 10/1997 | Barlow |
| 5,712,912 A | 1/1998 | Tomko |
| 5,721,435 A | 2/1998 | Troll |
| 5,729,365 A | 3/1998 | Sweatt |
| 5,736,330 A | 4/1998 | Fulton |
| 5,742,432 A | 4/1998 | Bianco |
| 5,745,615 A | 4/1998 | Atkins |
| 5,745,617 A | 4/1998 | Starodubov |
| 5,759,778 A | 6/1998 | Li |
| 5,760,961 A | 6/1998 | Tompkin |

| | | | | | | |
|---|---|---|---|---|---|---|
| 5,766,956 | A | 6/1998 | Groger | 6,218,194 B1 | 4/2001 | Lyndin |
| 5,771,251 | A | 6/1998 | Kringlebotn | 6,221,579 B1 | 4/2001 | Everhart |
| 5,776,694 | A | 7/1998 | Sheiness | 6,229,635 B1 | 5/2001 | Wulf |
| 5,793,502 | A | 8/1998 | Bianco | 6,229,827 B1 | 5/2001 | Fernald |
| 5,798,273 | A | 8/1998 | Shuler | 6,229,941 B1 | 5/2001 | Yoon |
| 5,799,231 | A | 8/1998 | Gates | 6,242,056 B1 | 6/2001 | Spencer |
| 5,801,857 | A | 9/1998 | Heckenkamp | 6,259,450 B1 | 7/2001 | Chiabrera |
| 5,804,384 | A | 9/1998 | Muller | 6,262,846 B1 | 7/2001 | Nakai |
| 5,812,272 | A | 9/1998 | King | 6,268,128 B1 | 7/2001 | Collins |
| 5,822,472 | A | 10/1998 | Danielzik | 6,277,628 B1 | 8/2001 | Johann |
| 5,824,478 | A | 10/1998 | Muller | 6,284,459 B1 | 9/2001 | Nova |
| 5,824,557 | A | 10/1998 | Burker | 6,285,806 B1 | 9/2001 | Kersey |
| 5,830,622 | A | 11/1998 | Canning | 6,288,220 B1 | 9/2001 | Kambara |
| 5,831,698 | A | 11/1998 | Depp | 6,292,282 B1 | 9/2001 | Mossberg |
| 5,837,475 | A | 11/1998 | Dorsel | 6,292,319 B1 | 9/2001 | Thomas, III |
| 5,837,552 | A | 11/1998 | Cotton | 6,301,047 B1 | 10/2001 | Hoshino |
| 5,841,555 | A | 11/1998 | Bianco | 6,304,263 B1 | 10/2001 | Chiabrera |
| 5,846,737 | A | 12/1998 | Kang | 6,306,587 B1 | 10/2001 | Royer |
| 5,861,113 | A | 1/1999 | Choquette et al. | 6,309,601 B1 | 10/2001 | Juncosa |
| 5,874,187 | A | 2/1999 | Colvin | 6,312,961 B1 | 11/2001 | Voirin |
| 5,881,197 | A | 3/1999 | Dong | 6,313,771 B1 | 11/2001 | Munroe |
| 5,895,750 | A | 4/1999 | Mushahwar | 6,314,220 B1 | 11/2001 | Mossberg |
| 5,922,550 | A | 7/1999 | Everhart | 6,319,668 B1 | 11/2001 | Nova |
| 5,922,617 | A | 7/1999 | Wang | 6,321,007 B1 | 11/2001 | Sanders |
| 5,925,562 | A | 7/1999 | Nova | 6,322,932 B1 | 11/2001 | Colvin |
| 5,925,878 | A | 7/1999 | Challener | RE37,473 E | 12/2001 | Challener |
| 5,945,679 | A | 8/1999 | Dorsel | 6,328,209 B1 | 12/2001 | O'Boyle |
| 5,972,542 | A | 10/1999 | Starodubov | 6,329,963 B1 | 12/2001 | Chiabrera |
| 5,976,896 | A | 11/1999 | Kumar | 6,331,273 B1 | 12/2001 | Nova |
| 5,981,166 | A | 11/1999 | Mandecki | 6,335,824 B1 | 1/2002 | Overbeck |
| 5,986,838 | A | 11/1999 | Thomas, III | 6,340,588 B1 | 1/2002 | Nova |
| 5,989,923 | A | 11/1999 | Lowe | 6,352,854 B1 | 3/2002 | Nova |
| 5,992,742 | A | 11/1999 | Sullivan | 6,355,198 B1 | 3/2002 | Kim |
| 5,998,796 | A | 12/1999 | Liu | 6,355,432 B1 | 3/2002 | Fodor |
| 6,001,510 | A | 12/1999 | Meng | 6,356,681 B1 | 3/2002 | Chen |
| 6,005,691 | A | 12/1999 | Grot | 6,359,734 B1 | 3/2002 | Staub |
| 6,017,754 | A | 1/2000 | Chesnut | 6,361,958 B1 | 3/2002 | Shieh |
| 6,025,129 | A | 2/2000 | Nova | 6,363,097 B1 | 3/2002 | Linke |
| 6,025,283 | A | 2/2000 | Robers | 6,371,370 B2 | 4/2002 | Sadler |
| 6,027,694 | A | 2/2000 | Boulton | 6,372,428 B1 | 4/2002 | Nova |
| 6,030,581 | A | 2/2000 | Virtanen | 6,383,754 B1 | 5/2002 | Kaufman |
| 6,035,082 | A | 3/2000 | Murphy | 6,391,562 B2 | 5/2002 | Kambara |
| 6,036,807 | A | 3/2000 | Brongers | 6,395,558 B1 | 5/2002 | Duveneck |
| 6,043,880 | A | 3/2000 | Andrews | 6,399,295 B1 | 6/2002 | Kaylor |
| 6,046,925 | A | 4/2000 | Tsien | 6,399,935 B1 | 6/2002 | Jovin |
| 6,049,727 | A | 4/2000 | Crothall | 6,403,320 B1 | 6/2002 | Read |
| 6,057,107 | A | 5/2000 | Fulton | 6,406,841 B1 | 6/2002 | Lee |
| 6,060,256 | A | 5/2000 | Everhart | 6,406,848 B1 | 6/2002 | Bridgham |
| 6,067,167 | A | 5/2000 | Atkinson | 6,416,714 B1 | 7/2002 | Nova |
| 6,067,392 | A | 5/2000 | Wakami | 6,416,952 B1 | 7/2002 | Pirrung |
| 6,078,048 | A | 6/2000 | Stevens | 6,417,010 B1 | 7/2002 | Cargill |
| 6,084,995 | A | 7/2000 | Clements | 6,424,056 B1 | 7/2002 | Irvin |
| 6,087,186 | A | 7/2000 | Cargill | 6,428,707 B1 | 8/2002 | Berger |
| 6,096,496 | A | 8/2000 | Frankel | 6,428,957 B1 | 8/2002 | Delenstarr |
| 6,096,596 | A | 8/2000 | Gonzalez | 6,429,022 B1 | 8/2002 | Kunz |
| 6,097,485 | A | 8/2000 | Lievan | 6,433,849 B1 | 8/2002 | Lowe |
| 6,103,535 | A | 8/2000 | Pilevar | 6,436,651 B1 | 8/2002 | Everhart |
| 6,118,127 | A | 9/2000 | Liu | 6,440,667 B1 | 8/2002 | Fodor |
| 6,128,077 | A | 10/2000 | Jovin | 6,456,762 B1 | 9/2002 | Nishiki |
| 6,137,931 | A | 10/2000 | Ishikawa | RE37,891 E | 10/2002 | Collins |
| 6,143,247 | A | 11/2000 | Sheppard, Jr. | 6,462,770 B1 | 10/2002 | Cline |
| 6,156,501 | A | 12/2000 | McGall | 6,489,606 B1 | 12/2002 | Kersey |
| 6,159,748 | A | 12/2000 | Hechinger | 6,496,287 B1 | 12/2002 | Seiberle |
| 6,160,240 | A | 12/2000 | Momma | 6,506,342 B1 | 1/2003 | Frankel |
| 6,160,656 | A | 12/2000 | Mossberg | 6,514,767 B1 | 2/2003 | Natan |
| 6,164,548 | A | 12/2000 | Curiel | 6,515,753 B2 | 2/2003 | Maher |
| 6,165,592 | A | 12/2000 | Berger | 6,522,406 B1 | 2/2003 | Rovira |
| 6,165,648 | A | 12/2000 | Colvin | 6,524,793 B1 | 2/2003 | Chandler |
| 6,174,648 | B1 | 1/2001 | Terao | 6,533,183 B2 | 3/2003 | Aasmul |
| 6,194,563 | B1 | 2/2001 | Cruickshank | 6,542,673 B1 | 4/2003 | Holter |
| 6,204,068 | B1 | 3/2001 | Soini et al. | 6,544,739 B1 | 4/2003 | Fodor |
| 6,204,969 | B1 | 3/2001 | Jang | 6,545,758 B1 | 4/2003 | Sandstrom |
| 6,214,560 | B1 | 4/2001 | Yguerabide | 6,552,809 B1 | 4/2003 | Bergeron |

| | | |
|---|---|---|
| 6,560,017 B1 | 5/2003 | Bianco |
| 6,565,770 B1 | 5/2003 | Mayer |
| 6,576,424 B2 | 6/2003 | Fodor |
| 6,578,712 B2 | 6/2003 | Lawandy |
| 6,592,036 B2 | 7/2003 | Sadler |
| 6,594,421 B1 | 7/2003 | Johnson |
| 6,609,728 B1 | 8/2003 | Voermann |
| 6,613,581 B1 | 9/2003 | Wada |
| 6,618,342 B1 | 9/2003 | Johnson |
| 6,622,916 B1 | 9/2003 | Bianco |
| 6,628,439 B2 | 9/2003 | Shiozawa |
| 6,632,655 B1 | 10/2003 | Mehta |
| 6,635,470 B1 | 10/2003 | Vann |
| 6,635,863 B1 | 10/2003 | Nihommori |
| 6,646,243 B2 | 11/2003 | Pirrung |
| 6,657,758 B1 | 12/2003 | Garner |
| 6,660,147 B1 | 12/2003 | Woudenberg |
| 6,678,429 B2 | 1/2004 | Mossberg |
| RE38,430 E | 2/2004 | Rosenstein |
| 6,689,316 B1 | 2/2004 | Blyth |
| 6,692,031 B2 | 2/2004 | McGrew |
| 6,692,912 B1 | 2/2004 | Boles |
| 6,708,618 B1 | 3/2004 | Tsai |
| 6,750,941 B2 | 6/2004 | Satoh et al. |
| 6,794,658 B2 | 9/2004 | MacAulay |
| 6,806,954 B2 | 10/2004 | Sandstrom |
| 6,858,184 B2 | 2/2005 | Pelrine |
| 6,874,639 B2 | 4/2005 | Lawandy |
| 6,881,789 B2 | 4/2005 | Bossé |
| 6,892,001 B2 | 5/2005 | Ohta |
| 6,905,885 B2 | 6/2005 | Colston |
| 6,908,737 B2 | 6/2005 | Ravkin |
| 6,919,009 B2 | 7/2005 | Stonas |
| 6,982,996 B1 | 1/2006 | Putnam |
| 7,045,049 B1 | 5/2006 | Natan |
| 7,065,032 B2 | 6/2006 | Horimai |
| 7,092,160 B2 | 8/2006 | Putnam |
| 7,106,513 B2 | 9/2006 | Moon |
| 7,122,384 B2 | 10/2006 | Prober |
| 7,126,755 B2 | 10/2006 | Moon |
| 7,164,533 B2 | 1/2007 | Moon |
| 7,190,522 B2 | 3/2007 | Moon |
| 7,215,628 B2 | 5/2007 | Horimai |
| 7,225,082 B1 | 5/2007 | Natan |
| 7,321,541 B2 | 1/2008 | Horimai |
| 7,339,148 B2 | 3/2008 | Kawano |
| 7,349,158 B2 | 3/2008 | Moon |
| 7,375,890 B2 | 5/2008 | Putnam |
| 7,399,643 B2 | 7/2008 | Moon et al. |
| 7,433,123 B2 | 10/2008 | Putnam et al. |
| 7,441,703 B2 | 10/2008 | Moon |
| 7,508,608 B2 | 3/2009 | Kersey et al. |
| 7,602,952 B2 | 10/2009 | Kersey |
| 7,604,173 B2 | 10/2009 | Kersey et al. |
| 7,619,819 B2 | 11/2009 | Moon et al. |
| 7,623,624 B2 | 11/2009 | Moon |
| 7,659,983 B2 | 2/2010 | Moon et al. |
| 2001/0007775 A1 | 7/2001 | Seul |
| 2001/0029049 A1* | 10/2001 | Walt et al. .................... 436/518 |
| 2002/0000471 A1 | 1/2002 | Aasmul |
| 2002/0006664 A1 | 1/2002 | Sabatini |
| 2002/0018430 A1 | 2/2002 | Heckenkamp |
| 2002/0021003 A1 | 2/2002 | McGrew |
| 2002/0022273 A1 | 2/2002 | Empedocles |
| 2002/0025534 A1 | 2/2002 | Goh |
| 2002/0031783 A1 | 3/2002 | Empedocles |
| 2002/0034747 A1 | 3/2002 | Bruchez |
| 2002/0039728 A1* | 4/2002 | Kain et al. .................... 435/6 |
| 2002/0039732 A1 | 4/2002 | Bruchez |
| 2002/0074513 A1 | 6/2002 | Abel |
| 2002/0084329 A1 | 7/2002 | Kaye |
| 2002/0090650 A1 | 7/2002 | Empedocles |
| 2002/0094528 A1 | 7/2002 | Salafsky |
| 2002/0097658 A1 | 7/2002 | Worthington |
| 2002/0155490 A1 | 10/2002 | Skinner |
| 2002/0174918 A1 | 11/2002 | Fugimura et al. |
| 2002/0197456 A1 | 12/2002 | Pope |
| 2003/0008323 A1 | 1/2003 | Ravkin |
| 2003/0021003 A1 | 1/2003 | Ono |
| 2003/0032203 A1 | 2/2003 | Sabatini |
| 2003/0077038 A1 | 4/2003 | Murashima |
| 2003/0082568 A1 | 5/2003 | Phan |
| 2003/0082587 A1 | 5/2003 | Seul |
| 2003/0129654 A1 | 7/2003 | Ravkin |
| 2003/0138208 A1 | 7/2003 | Pawlak |
| 2003/0142704 A1 | 7/2003 | Lawandy |
| 2003/0142713 A1 | 7/2003 | Lawandy |
| 2003/0153006 A1 | 8/2003 | Washizu |
| 2003/0162296 A1 | 8/2003 | Lawandy |
| 2003/0184730 A1 | 10/2003 | Price |
| 2003/0203390 A1 | 10/2003 | Kaye |
| 2003/0228610 A1 | 12/2003 | Seul |
| 2004/0027968 A1 | 2/2004 | Horimai |
| 2004/0047030 A1 | 3/2004 | MacAulay |
| 2004/0062178 A1 | 4/2004 | Horimai |
| 2004/0075907 A1 | 4/2004 | Moon |
| 2004/0100636 A1 | 5/2004 | Somekh |
| 2004/0100892 A1 | 5/2004 | Horimai |
| 2004/0125370 A1 | 7/2004 | Montagu |
| 2004/0125424 A1 | 7/2004 | Moon |
| 2004/0126875 A1 | 7/2004 | Putnam |
| 2004/0132205 A1 | 7/2004 | Moon |
| 2004/0156471 A1 | 8/2004 | Sakata |
| 2004/0170356 A1 | 9/2004 | Iazikov |
| 2004/0175842 A1 | 9/2004 | Roitman |
| 2004/0179267 A1 | 9/2004 | Moon |
| 2004/0209376 A1 | 10/2004 | Natan |
| 2004/0233485 A1 | 11/2004 | Moon |
| 2004/0263923 A1 | 12/2004 | Moon |
| 2005/0042764 A1 | 2/2005 | Sailor |
| 2005/0056587 A1 | 3/2005 | Allen et al. |
| 2005/0220408 A1 | 10/2005 | Putnam |
| 2005/0227252 A1 | 10/2005 | Moon |
| 2005/0270603 A1 | 12/2005 | Putnam |
| 2006/0023310 A1 | 2/2006 | Putnam |
| 2006/0028727 A1 | 2/2006 | Moon |
| 2006/0050544 A1 | 3/2006 | Horimai |
| 2006/0057729 A1 | 3/2006 | Moon |
| 2006/0063271 A1 | 3/2006 | Putnam |
| 2006/0067179 A1 | 3/2006 | Matsumoto |
| 2006/0071075 A1 | 4/2006 | Moon et al. |
| 2006/0072177 A1 | 4/2006 | Putnam |
| 2006/0118630 A1 | 6/2006 | Kersey |
| 2006/0119913 A1 | 6/2006 | Moon |
| 2006/0132877 A1 | 6/2006 | Kersey |
| 2006/0134324 A1 | 6/2006 | Putnam |
| 2006/0139635 A1 | 6/2006 | Kersey |
| 2006/0140074 A1 | 6/2006 | Horimai |
| 2006/0160208 A1 | 7/2006 | Putnam |
| 2007/0121181 A1 | 5/2007 | Moon |
| 2007/0236789 A1 | 10/2007 | Moon |
| 2008/0085565 A1 | 4/2008 | Moon |
| 2008/0129990 A1 | 6/2008 | Moon |
| 2008/0165656 A1 | 7/2008 | Moon et al. |
| 2008/0170664 A1 | 7/2008 | Kalman |
| 2008/0192311 A1 | 8/2008 | Horimai |
| 2009/0034078 A1 | 2/2009 | Putnam et al. |
| 2009/0040885 A1 | 2/2009 | Horimai |
| 2009/0073520 A1 | 3/2009 | Kersey et al. |
| 2009/0194589 A1 | 8/2009 | Moon et al. |
| 2010/0025482 A1 | 2/2010 | Moon |
| 2010/0072278 A1 | 3/2010 | Putnam |

| | | |
|---|---|---|
| 2010/0099574 A1 | 4/2010 | Moon |

FOREIGN PATENT DOCUMENTS

| | | |
|---|---|---|
| DE | 2416652 | 10/1975 |
| EP | 0 395 300 | 10/1990 |
| EP | 0 723 149 | 7/1996 |
| EP | 0 798 573 A1 | 10/1997 |
| EP | 0 911 667 A1 | 4/1999 |
| EP | 916981 | 5/1999 |
| EP | 0 972 817 A1 | 1/2000 |
| EP | 1182054 | 2/2002 |
| EP | 1219979 | 7/2002 |
| GB | 2 118 189 | 10/1983 |
| GB | 2129551 | 5/1984 |
| GB | 2 138 821 | 10/1984 |
| GB | 2 299 235 | 9/1996 |
| GB | 2 306 484 | 5/1997 |
| GB | 2 319 838 | 6/1998 |
| GB | 2372100 | 8/2002 |
| JP | 58143254 | 8/1983 |
| JP | 08102544 | 4/1986 |
| JP | 01047950 | 2/1989 |
| JP | 05307119 | 11/1993 |
| JP | 6333102 | 12/1994 |
| JP | 08272923 | 10/1996 |
| JP | 10160705 | 6/1998 |
| JP | 11119029 | 4/1999 |
| JP | 20035521 | 2/2000 |
| JP | 00249706 | 9/2000 |
| JP | 200191715 | 4/2001 |
| JP | 2002182022 | 2/2002 |
| JP | 2002513166 | 5/2002 |
| JP | 200300467 | 1/2003 |
| WO | WO 91/06496 | 5/1991 |
| WO | WO 93/09668 | 5/1993 |
| WO | WO 94/28119 | 12/1994 |
| WO | WO 96/24061 | 8/1996 |
| WO | WO 96/36436 | 11/1996 |
| WO | WO9636436 | 11/1996 |
| WO | WO 97/12680 | 4/1997 |
| WO | WO 97/15390 | 5/1997 |
| WO | WO 97/15690 | 5/1997 |
| WO | WO 97/17258 | 5/1997 |
| WO | WO 97/31282 | 8/1997 |
| WO | WO 97/34171 | 9/1997 |
| WO | WO 98/04740 | 2/1998 |
| WO | WO 98/24549 | 6/1998 |
| WO | WO 99/02266 | 1/1999 |
| WO | WO 99/09042 | 2/1999 |
| WO | WO 99/32654 | 7/1999 |
| WO | WO 99/42209 | 8/1999 |
| WO | WO 00/08443 | 2/2000 |
| WO | WO0016893 | 3/2000 |
| WO | WO 00/19262 | 6/2000 |
| WO | WO 00/37914 | 6/2000 |
| WO | WO 00/37969 | 6/2000 |
| WO | WO 00/39617 | 7/2000 |
| WO | WO 00/63419 | 10/2000 |
| WO | WO0061198 | 10/2000 |
| WO | WO0158583 | 8/2001 |
| WO | WO0171322 | 9/2001 |
| WO | WO 01/78889 | 10/2001 |
| WO | WO0178889 | 10/2001 |
| WO | WO 01/90225 | 11/2001 |
| WO | WO 02/059603 | 8/2002 |
| WO | WO 02/064829 | 8/2002 |
| WO | WO02059306 | 8/2002 |
| WO | WO03061983 | 7/2003 |
| WO | WO 03/091731 | 11/2003 |
| WO | WO 2004/011940 | 2/2004 |
| WO | WO 2004/015418 | 2/2004 |
| WO | WO 2004/019276 | 3/2004 |
| WO | WO 2004/025561 | 3/2004 |
| WO | WO 2004/025563 | 3/2004 |
| WO | WO2004019276 | 3/2004 |
| WO | WO2004024328 | 3/2004 |
| WO | WO2004025562 | 3/2004 |
| WO | WO 2004/034012 | 4/2004 |
| WO | WO 2004/046697 | 6/2004 |
| WO | WO2004066210 | 8/2004 |
| WO | WO 2005/026729 | 3/2005 |
| WO | WO 2005/027031 | 3/2005 |
| WO | WO 2005/029047 | 3/2005 |
| WO | WO 2005/033681 | 4/2005 |
| WO | WO 2005/050207 | 6/2005 |
| WO | WO 2005/079544 | 9/2005 |
| WO | WO 2006/020363 | 2/2006 |
| WO | WO 2006/055735 | 5/2006 |
| WO | WO 2006/055736 | 5/2006 |
| WO | WO 2006/076053 | 7/2006 |

OTHER PUBLICATIONS

Lide (CRC Handbook of Chemistry and Physics, 71st ed.).
Othonos, X. Lee; Superimposed Multiple Bragg Gratings, Nov. 10, 1994, vol. 30, No. 23.
Patil et al. (AAPS PharmSciTech, Mar. 24, 2006, vol. 7, pp. E1-E7).
Po Ki Yuen, Microbarcode Sorting Device; Science & Technology, Corning Incorporated, Corning, New York 14831-0007, USA.
International Search Report and Written Opinion for International Application No. PCT/US2003/26315.
International Search Report and Written Opinion for International Application No. PCT/US2003/26316.
International Search Report for International Application No. PCT/US2003/28862.
International Search Report for International Application No. PCT/US2003/28874.
International Search Report for International Application No. PCT/US2003/28875.
International Search Report for International Application No. PCT/US2003/28887.
International Search Report for International Application No. PCT/US2003/28890.
International Search Report and Written Opinion for International Application No. PCT/US2003/29164.
International Search Report for International Application No. PCT/US2003/29244.
International Search Report and Written Opinion for International Application No. PCT/US2004/01685.
International Search Report and Written Opinion for International Application No. PCT/US2004/30037.
International Search Report and Written Opinion for International Application No. PCT/US2004/30038.
International Search Report and Written Opinion for International Application No. PCT/US2004/30300.
International Search Report and Written Opinion for International Application No. PCT/US2004/32084.
International Search Report and Written Opinion for International Application No. PCT/US2004/38416.
International Search Report and Written Opinion for International Application No. PCT/US2005/05743.
International Search Report and Written Opinion for International Application No. PCT/US2005/05745.
International Search Report and Written Opinion for International Application No. PCT/US2005/26289.
International Search Report and Written Opinion for International Application No. PCT/US2005/33694.
International Search Report and Written Opinion for International Application No. PCT/US2005/41730.
International Search Report and Written Opinion for International Application No. PCT/US2005/41731.
"Compact Disc Arrayer"; V&P; Scientific; Nov. 17, 2003; pp. 1-4.
"Electronically Scanned Confocal Imaging System"; IBM Technical Disclosure Bulletin; vol. 36; No. 06B; Jun. 1993; pp. 261-262.

"Ben Beune Patent Licensing Director of Philips IP&S"; Replication & Duplication—News & Technology; Jan.-Feb. 2002; pp. 1-2.

Andrew Marshall; "DNA Chips: Array of Possibilities"; Nature Biotechnology vol. 16 Jan. 1998; pp. 27-31.

Burstein Technology, Inc.; "Angel Strategies Tombstone"; 1 pg.

de Beer et al., "Forward-Scattering Degenerate Four-Wave Mixing for Sensitive Absorption Detection in Microseparation Systems Coupling to Micro-Column Liquid Chromatography"; Journal of Chromatography A. 811 (1998); pp. 35-45.

Fonjallaz et al., "Interferometric Side Diffraction Technique for the Characterisation of Fiber Gratings"; 1999 OSA Conference, Sep. 23-25; 3 pgs.

G. Kakarantzas et al.;"Transmission Filters Based on periodically Micro-tapered Fibre"; CLE0/2000/Friday Morning; 8:45 a.m.; pp. 574-575, 2000.

Hideki Kambara; Recent Progress in fluorescent DNA Analyzers and Methods; Current Topics in Analytical checmistry; vol. 1, (1998) pp. 21-36.

Ivan Oransky; "Sequencing on Compact Disc? Microgenomics of Breast Cancer; Better Binding Site Prediction"; vol. 17 / Issue 13 / 35 / Jun. 30, 2003; 13 pgs.

Kashyap R.; "Fiber Bragg Gratings"; Academic Press, Ch. 9; pp. 430-433.

Kogelnik H; "Coupled Wave Theory for Thick Hologram Gratings"; The Bell System Technical Journal, 48(9):2909-2947 (1969).

Krug P., "Measurement of Index Modulation Along an Optical Fiber Bragg Grating"; Optics Letters, 20(17):1767-1769, 1995.

Leith et al., "Holographic Data Storage in Three-Dimensional Media"; Applied Optics, vol. 5, No. 8, Aug. 1966; 21 pgs.

Mark O. Worthington; "Curriculum Vitae"; Jan. 5, 2004; 4 pgs.

Masato Mitsuhashi; "Gene Manipulation on Plastic Plates"; Nature, vol. 357, Jun. 11, 1992; pp. 519-520.

Michael C. Needels et al.; "Generation and Screening of an Oligonucleotide-Encoded Synthetic Peptide Library"; Proc Natl. Acad. Sci. USA, vol. 90;pp. 10700-10704, Nov. 1993.

Michael J. Kozal; "Extensive Polymorphisms Observed in HIV-1 Clade B Protease Gene Using High-Density Oligonucleotide Arrays"; Nature Medicine, vol. 2, No. 7, Jul. 1996; pp. 753-759.

Shelia R. Nicerwarner-Peña, "Submicrometer Metallic Barcodes"; Science, vol. 294; Oct. 5, 2001; 5 pgs.

Thomas Laurell; "Enhanced Enzyme Activity in Silicon Integrated Enzyme Reactors Utilizing Porous Silicon as the Coupling Matrix"; Sensor & Actuators B 31 (1996); pp. 161-166.

Vander Lugt; "Design Relationships For Holographic Memories"; Applied Optics, vol. 12, No. 7, Jul. 1973; pp. 1675-1685.

W.R. Rigby; "An Anodizing Process for the Production of Inorganic Microfiltration Membranes"; 2436Transactions of the Institute of Metal Finishing;68,Aug. 1990,Part 3 p. 95-98.

Yoshinobu Kohara; "DNA Probes on Beads Arrayed in a Capillary, 'Bead-Array',Exhibited High Hybridization Performance"; Nucleic Acids Research, 2002, vol. 30, No. 16 e87; 7 pgs.

Material Safety Data Sheet Aquaclean 900; Aquabond Technologies (ABT); 1 pg., revised May 2000.

US 6,780,301, 08/2004, Natan (withdrawn)

* cited by examiner

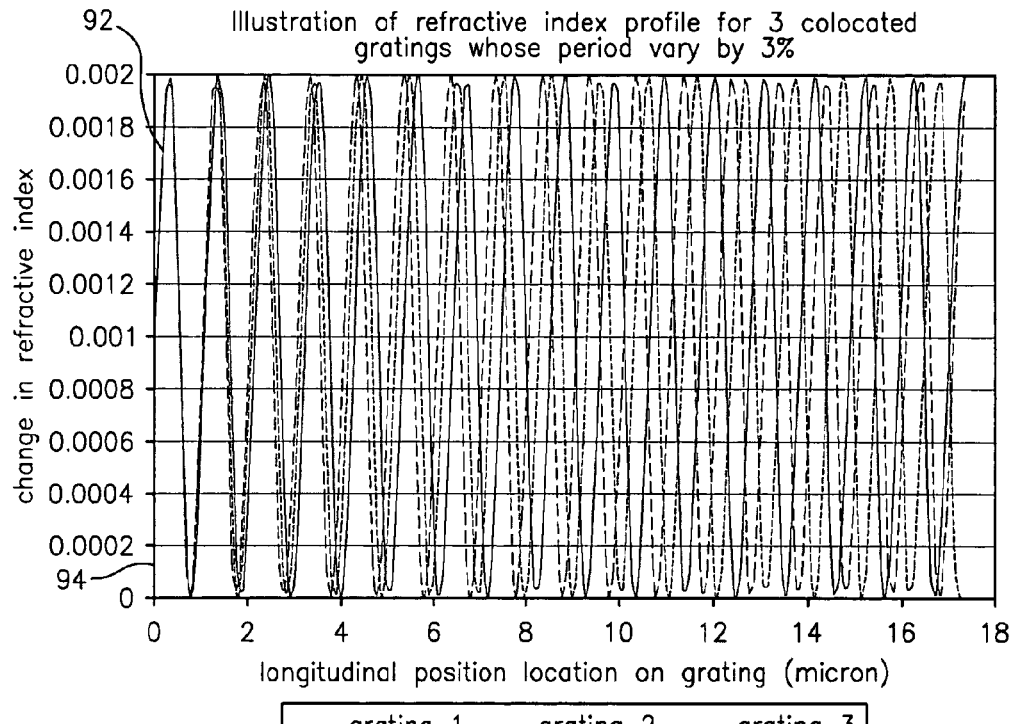
Illustration (b)
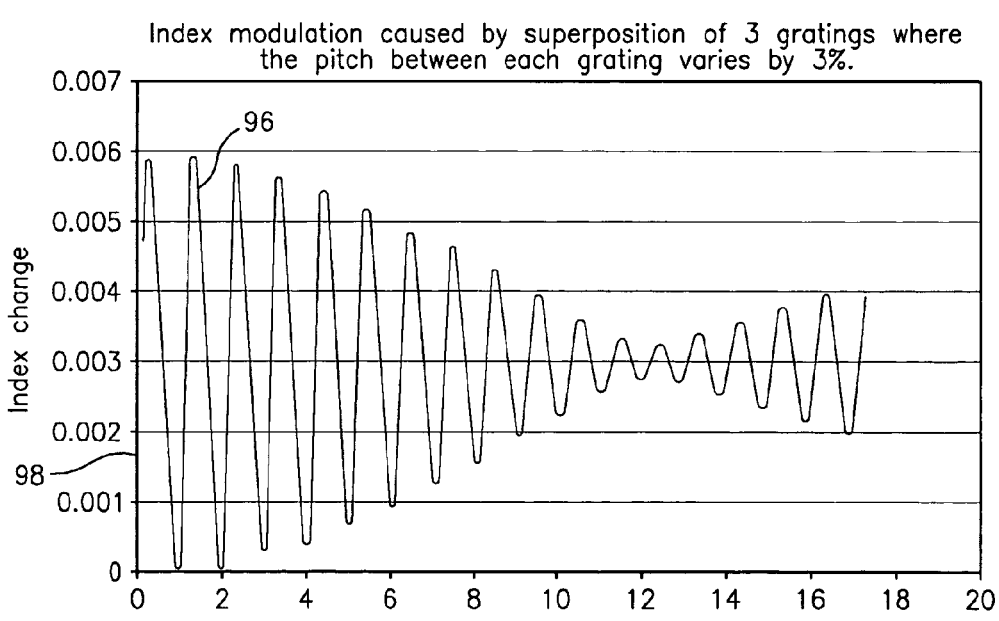
FIG. 14
Illustration (d)

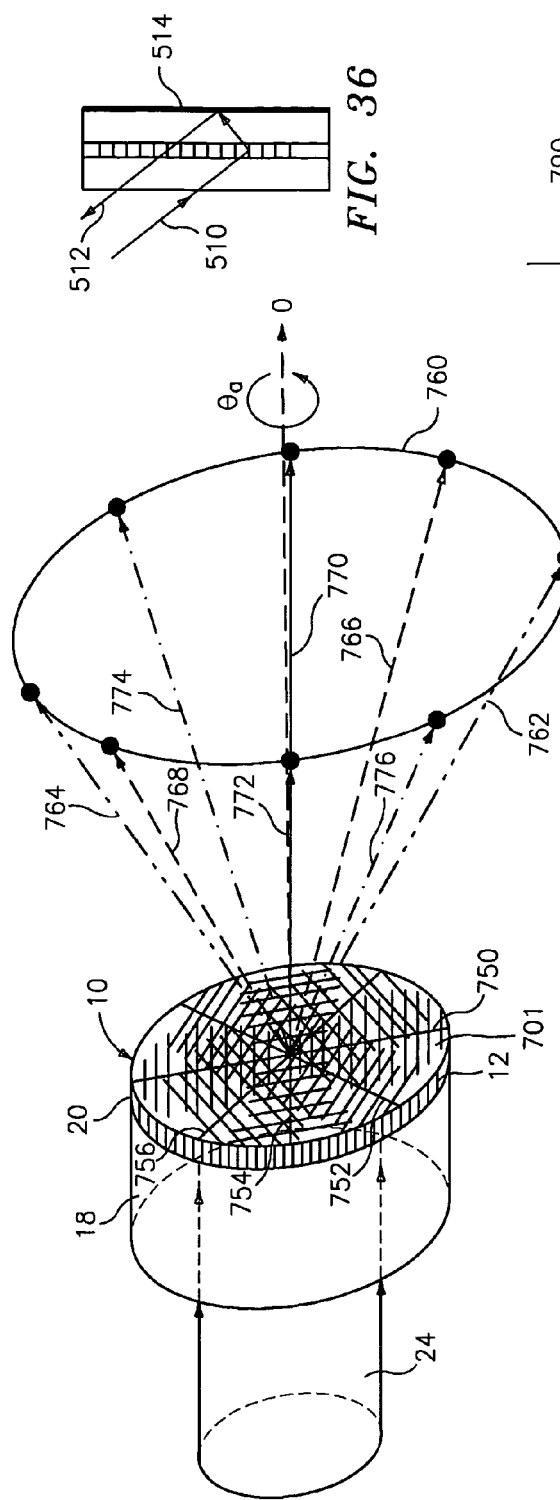
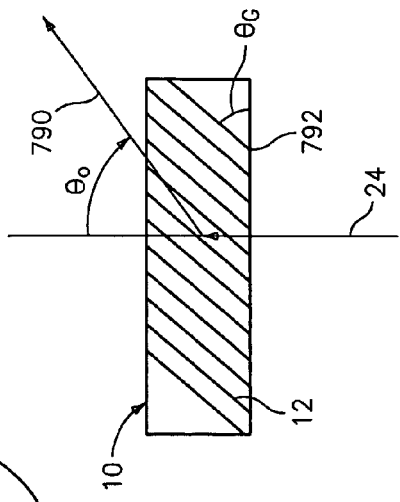
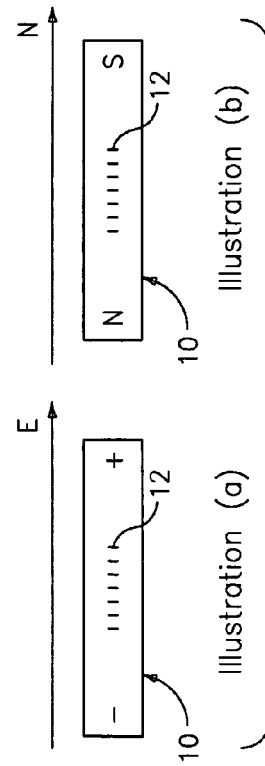
FIG. 36
FIG. 20
FIG. 19
FIG. 37

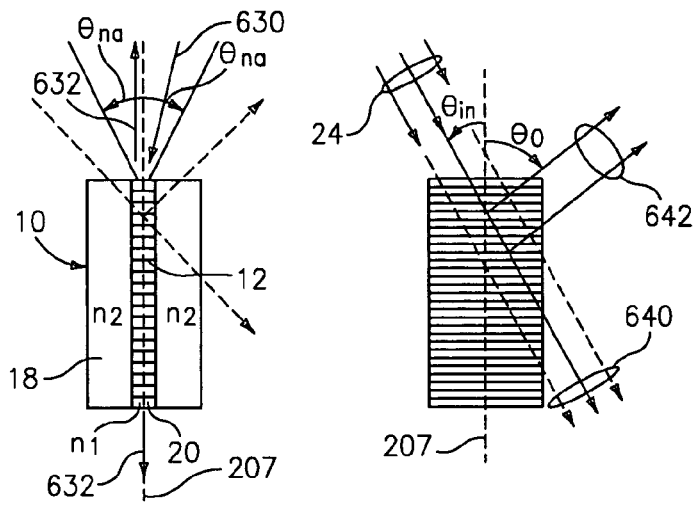
*FIG. 23*  *FIG. 24*
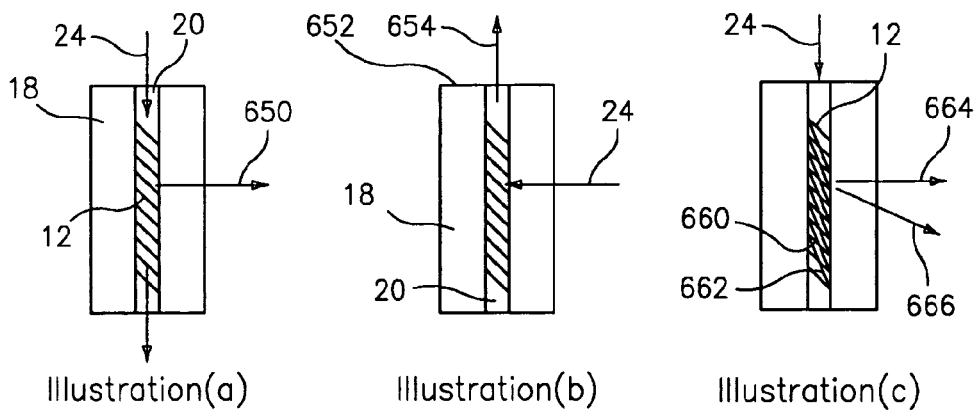
Illustration(a)   Illustration(b)   Illustration(c)
*FIG. 25*
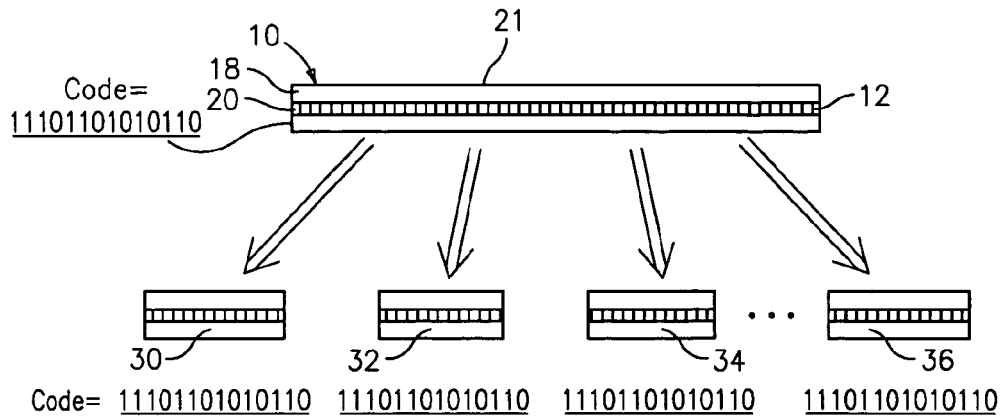
*FIG. 27*

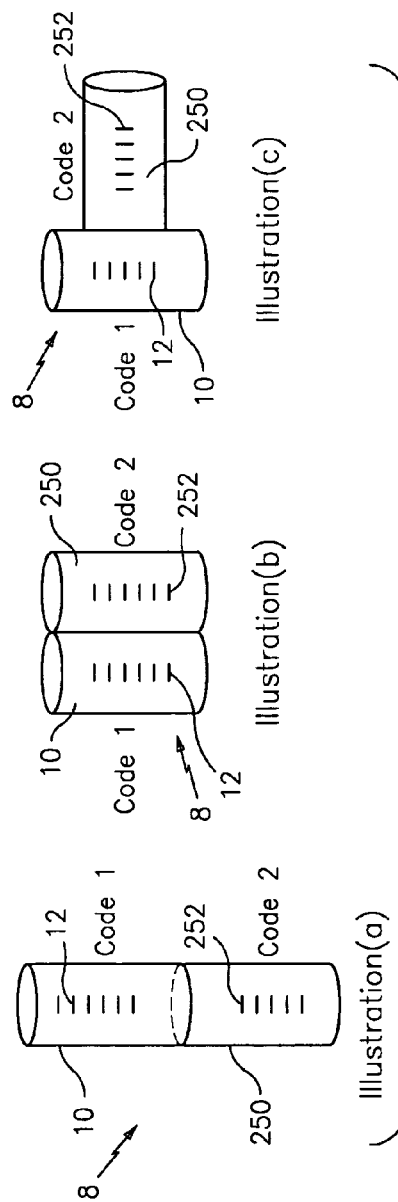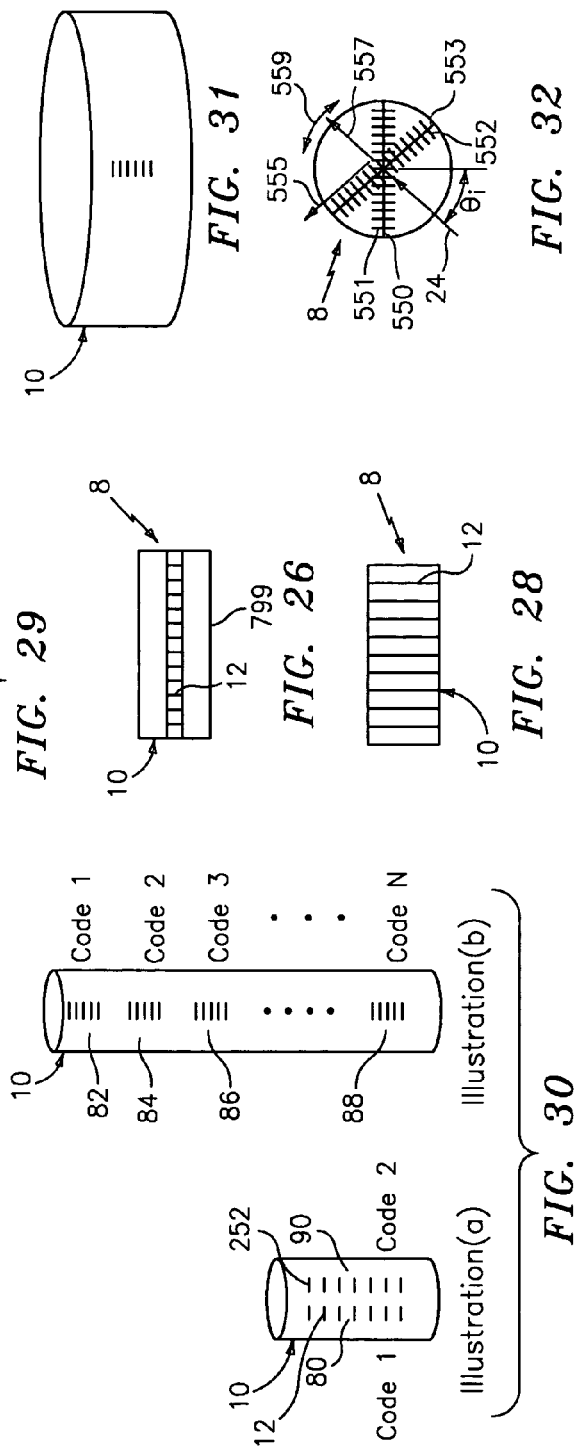

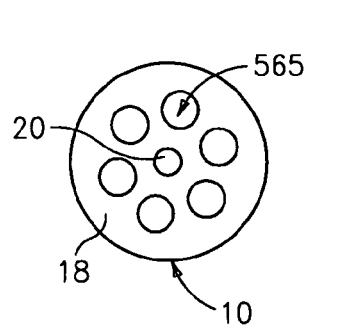
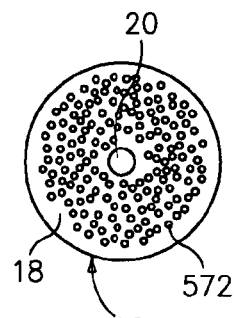
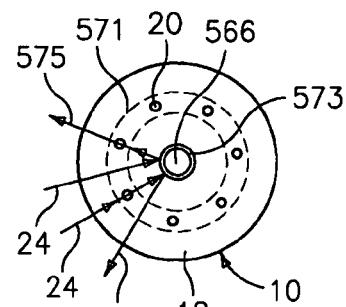
Illustration(a)  Illustration(b)  Illustration(c)
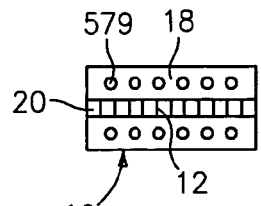
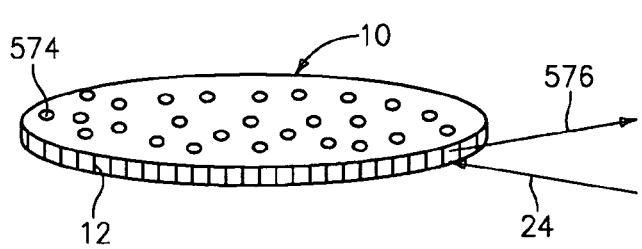
Illustration(d)  Illustration(e)
*FIG. 33*
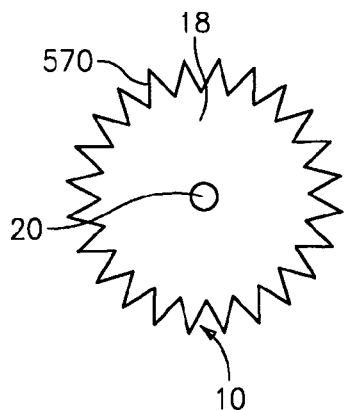
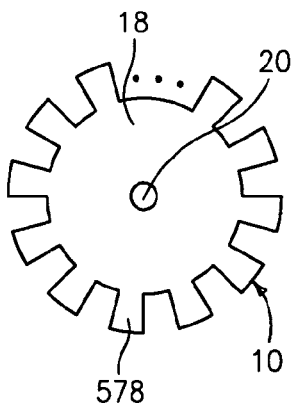
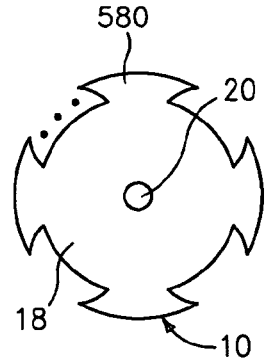
Illustration(a)  Illustration(b)  Illustration(c)
*FIG. 34*
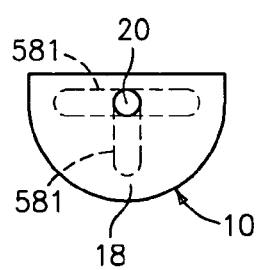
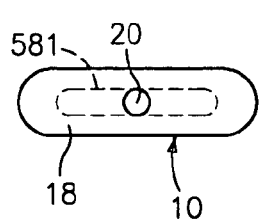
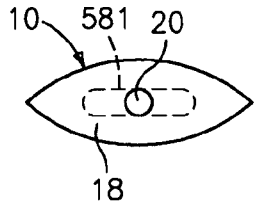
Illustration(a)  Illustration(b)  Illustration(c)
*FIG. 35*

0.5D<T<1.5D 0.8D<T<1.2D

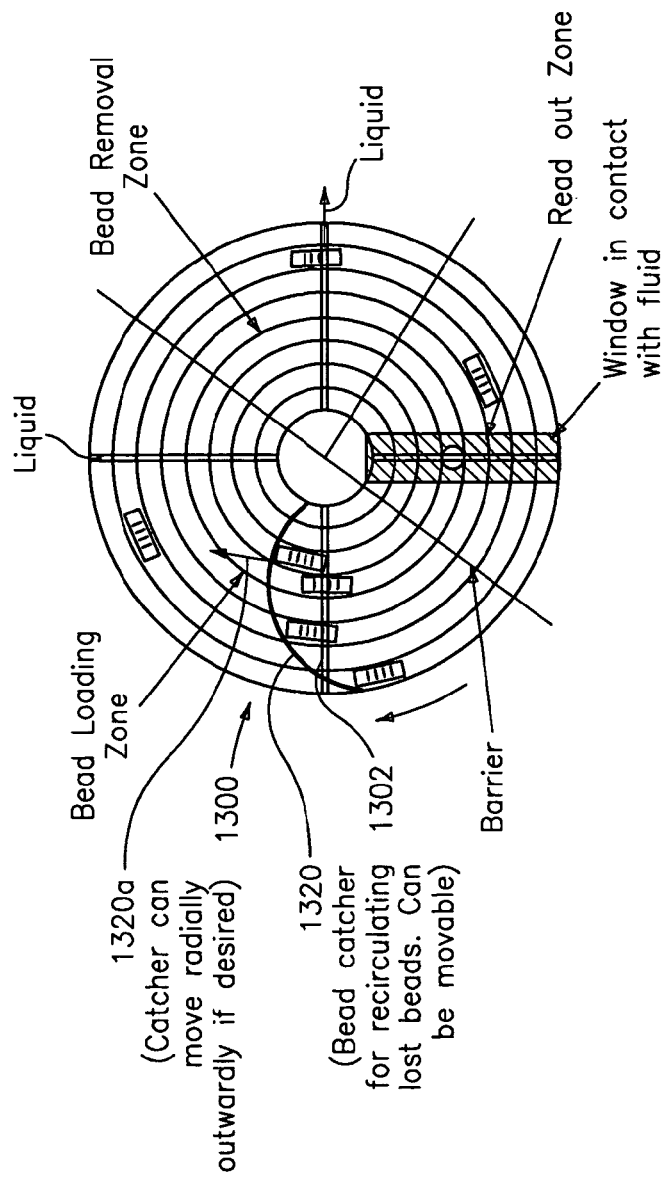

METHODS OF IDENTIFYING AN ANALYTE AND NUCLEIC ACID ANALYSIS

CROSS-REFERENCE TO RELATED APPLICATIONS

This application is a continuation of U.S. application Ser. No. 11/607,837, filed Nov. 30, 2006, entitled "Hybrid Random Bead/Chip Base Microarray," which is a continuation of U.S. application Ser. No. 10/763,995 (the '995 application) (issued as U.S. Pat. No. 7,164,533), filed Jan. 22, 2004, which claims the benefit of U.S. Provisional Patent Applications No. 60/441,678, filed Jan. 22, 2003, entitled "Hybrid Random Bead/Chip Microarray"; and 60/519,932, filed Nov. 14, 2003, entitled, "Diffraction Grating-Based Encoded Microparticles for Multiplexed Experiments." The '995 application also claims priority to and is a continuation-in-part of U.S. patent application Ser. No. 10/661,234, filed Sep. 12, 2003, entitled "Diffraction Grating-Based Optical Identification Element"; Ser. No. 10/661,031, filed Sep. 12, 2003, entitled "Diffraction Grating-Based Encoded Micro-Particles for Multiplexed Experiments"; and Ser. No. 10/661,836, filed Sep. 12, 2003, entitled "Method and Apparatus for Aligning Microbeads in order to Interrogate the Same". All of the foregoing applications are incorporated herein by reference in their entirety.

U.S. patent application Ser. Nos. 10/661,082, 10/661,115, 10/661,254 and 10/661,116, filed Sep. 12, 2003, contain subject matter related to that disclosed herein, all of which are incorporated by reference in their entirety.

TECHNICAL FIELD

This invention relates to optical identification, and more particularly to diffraction grating-based encoded optical elements/micro-particles for performing multiplexed experiments.

BACKGROUND ART

A common class of experiments, known as a multiplexed assay or multiplexed experiment, comprises mixing (or reacting) a labeled target analyte or sample (which may have known or unknown properties or sequences) with a set of "probe" or reference substances (which also may have known or unknown properties or sequences). Multiplexing allows many properties of the target analyte to be probed or evaluated simultaneously (i.e., in parallel). For example, in a gene expression assay, the "target" analyte, usually an unknown sequence of DNA, is labeled with a fluorescent molecule to form the labeled analyte.

In a known DNA/genomic sequencing assay, each probe consists of known DNA sequences of a predetermined length, which are attached to a labeled (or encoded) bead or to a known location or position (or spot) on a substrate.

When the labeled target analyte is mixed with the probes, segments of the DNA sequence of the labeled target analyte will selectively bind to complementary segments of the DNA sequence of the known probe. The known probes are then spatially separated and examined for fluorescence. The probes that fluoresce indicate that the DNA sequence strands of the target analyte have attached or hybridized to the complementary DNA of the probe. The DNA sequences in the target analyte can then be determined by knowing the complementary DNA (or cDNA) sequence of each known probe to which the labeled target is attached. In addition the level of fluorescence is indicative of how many target molecules hybridized to the probe molecules for a given bead or spot on a substrate.

Generally, the probes are identified either by spatial location on a substrate or by attaching the probe to a bead or particle that is labeled (or encoded) to identify the probe, and ultimately the "target" analyte. The first approach separates the probes in a predetermined grid, where the probe's identity is linked to its position on the grid. One example of this is a "chip" format, where DNA is attached to a 2-D substrate or microarray, where oligomer DNA sequences are selectively attached (either by spotting or grown) onto small sections or spots on the surface of the substrate in a predetermined spatial order and location on a substrate (usually a planar substrate, such as a glass microscope slide), such as that sold by Affymetrix and others.

A second or "bead-based" approach, for identifying the probe allows the probes to mix without any specific spatial position, which is often called the "random bead assay" approach. In this approach the probes are attached to a small bead or particle instead of a larger substrate so they are free to move (usually in a liquid medium). This approach has an advantage in that the analyte reaction can be performed in a liquid/solution by conventional wet-chemistry techniques, which gives the probes a better opportunity to interact with the analyte. However, this approach requires that each bead or probe be individually identifiable.

There are many known methods and substrate types that can be used for tagging or otherwise uniquely identifying individual beads with attached probes. Known methods include using polystyrene latex spheres that are colored or fluorescent labeled, such as that sold by Luminex and others. Other methods include using small plastic cans with a conventional bar code applied, or a small container includes a solid support material and a radio-frequency tag, such as that sold by Pharmaseq and others.

The beads have the advantage of using liquid or solution based chemistry and flexibility but current bead technology does have a limited number of identifiable codes and/or are not suitable for harsh environments/chemicals. Whereas chips typically have the advantage of having higher density (or high multiplexing) capability than beads and can be read using standard fluorescence scanners, but are not as flexible or economically customizable as beads.

Therefore, it would be desirable to provide a platform with benefits of both the bead-based platforms and the chip-based platforms.

SUMMARY OF THE INVENTION

Objects of the present invention include provision of a platform that provides benefits of both bead-based platforms and chip-based platforms.

According to the present invention, a method of performing an assay process is provided comprising the steps of: providing microbeads in a solution, each microbead having a particle substrate with a grating with a superposition of different predetermined regular periodic variations of the index of refraction disposed in the particle along a grating axis and indicative of a code; placing the microbeads on an alignment substrate; reading codes of the microbeads and the position thereof on the alignment substrate; reading the fluorescence on each microbead and the position thereof on the alignment substrate; and determining an assay result based on bead position and bead code of the earlier reading steps. The particle substrate may be formed of a transparent dielectric material with the index of refraction at each point in the dielectric material, and the superposition of different regular periodic variations in the index of refraction is disposed along the length of the particle substrate.

The present invention also includes apparatus for reading microbeads that form part of an assay process, comprising: an alignment substrate for receiving the microbeads thereon: and a bead mapper for reading codes of the microbeads and the position thereof on the alignment substrate.

The invention is a significant improvement over chip-based assay platforms and existing bead-based assay platforms. In particular, the bead assay can be performed with solution or wet chemistry, then when the experiment is completed, the beads are placed on a slide, plate, or substrate (e.g., a groove plate) which aligns the beads. The beads are then placed in a "bead mapper", which reads the codes and maps each bead code with a unique position on the slide. Once the beads have been mapped, the slide may be placed in any standard scanner capable of detecting the label used for the analyte and its position on the slide. For example, a standard fluorescence reader/scanner used to read chip-based microarrays may be used to read the fluorescence intensity at each bead location on the slide, similar to reading the fluorescence of each spot on the chip. The intensity/location information is then combined with the code/location information to determine which probes are exhibiting fluorescence, and the intensity thereof.

The invention may be viewed as a "chip" or "microchip" approach where the probes (or beads) are assembled from many individually fabricated parts. The beads may be ordered in one dimension along the grooves, but are randomly distributed (but oriented) along each groove. However, any technique may be used that allows the bead location to be identified.

This self-assembled "chip" approach has many advantages over conventional bead based assays. In particular, since the beads are fixed on a chip substrate (e.g., groove plate), they may be examined and re-examined at any time. Also, beads of interest can be easily removed and sorted from the plate/chip after an experiment is performed. More specifically, after reading the chip, the beads may be removed from the chip for further and/or alternative processing or experiments. If desired, the chip substrate and/or the beads may be reused in other experiments or assays. Further, a fixed plate format is easier to use in experiments that vary the temperature. Still further, a fixed plate format allows convenient use of a standard chip reader to examine the beads. Also, the beads do not need to be examined using a flow cytometer.

Alternatively, instead of performing the analyte reaction or hybridization reaction before placing the beads on the chip, the beads (or probe particles) can be assembled into the chip format before the analyte reaction process. In that case, the analyte can be applied to the chip with the beads disposed thereon, in which case the analyte reaction would occur on the chip.

The microbeads are inexpensive to manufacture and the identification codes are easy and inexpensive to imprint into the microbeads. The codes are digitally readable and easily adapted to optical coding techniques. Thus, the bead mapper optical readout is very simple and inexpensive to implement. Further, the invention allows for the use of a standard scanner to the label used for the analyte, which may avoid the need to purchase an additional scanner.

Further, the beads may be oriented in 1-D in grooves (which may or may not be linear) and are randomly distributed along the grooves. Also, the beads need not be fixed in any way in the grooves other than by capillary force if desired.

The code on the bead is not affected by spot imperfections, scratches, cracks or breaks. In addition, splitting or slicing an element axially produces more elements with the same code; therefore, when a bead is axially split-up, the code is not lost, but instead replicated in each piece. Unlike electronic ID elements, the elements of the present invention are not affected by nuclear or electromagnetic radiation.

The invention may be used in any assay or multiplexed experiment. The present invention may be used with any known combinatorial chemistry or biochemistry assay process, and are especially adaptable to assays having solid phase immobilization. The invention may be used in many areas such as drug discovery, functionalized substrates, biology, proteomics, combinatorial chemistry, and any assays or multiplexed experiments. Examples of common assays are SNP (single nucleotide polymorphism) detection, DNA/genomic sequence analysis, genotyping, gene expression assays, proteomics assay, peptide assays, antigen/antibody assays (immunoassay), ligand/receptor assays, DNA analysis/tracking/sorting/tagging, as well as tagging of molecules, biological particles, cell identification and sorting, matrix support materials, receptor binding assays, scintillation proximity assays, radioactive or non-radioactive proximity assays, and other assays, high throughput drug/genome screening, and/or massively parallel assay applications. The analyte can be labeled, detected or identified with any technique capable of being used in an assay with arrays or beads, including but not limited to fluorescent, luminescent, phosphorescent, quantum dot, light scattering colloidal particles, radioactive isotopes, mass spectroscopy, NMR (nuclear magnetic resonance), EPR (electro paramagnetic resonance), ESR (electron spin resonance), IR (infrared), FTIR (Fourier transform infra red), Raman spectroscopy, or other magnetic, vibrational, electromagnetic, or optical labeling or detection techniques. Accordingly, the scanner may any scanner capable of measuring or sensing any of the foregoing analyte labels.

The invention provides uniquely identifiable beads with reaction supports by active coatings for reaction tracking to perform multiplexed experiments. The invention may also be used in any chemical and/or biochemical purification, isolation, or filtering-type process where bead or bead-like solid supports may be used (e.g., chromatographic techniques, such as affinity column purification). In that case, the above techniques for labeling, detection or identification may be used.

The foregoing and other objects, features and advantages of the present invention will become more apparent in light of the following detailed description of exemplary embodiments thereof.

BRIEF DESCRIPTION OF THE DRAWINGS

FIG. 19 is a perspective view showing azimuthal multiplexing of a thin grating for an optical identification element, in accordance with the present invention.

FIG. 20 is side view of a blazed grating for an optical identification element, in accordance with the present invention.

FIGS. 23-24 are side views of an optical identification element where light is incident on an end face, in accordance with the present invention.

FIG. 25, illustrations (a)-(c) are side views of an optical identification element having a blazed grating, in accordance with the present invention.

FIG. 26 is a side view of an optical identification element having a coating, in accordance with the present invention.

FIG. 27 is a side view of whole and partitioned optical identification element, in accordance with the present invention.

FIG. 28 is a side view of an optical identification element having a grating across an entire dimension, in accordance with the present invention.

FIG. 29, illustrations (a)-(c), are perspective views of alternative embodiments for an optical identification element, in accordance with the present invention.

FIG. 30, illustrations (a)-(b), are perspective views of an optical identification element having multiple grating locations, in accordance with the present invention.

FIG. 31, is a perspective view of an alternative embodiment for an optical identification element, in accordance with the present invention.

FIG. 32 is a view an optical identification element having a plurality of gratings located rotationally around the optical identification element, in accordance with the present invention.

FIG. 33 illustrations (a)-(e) show various geometries of an optical identification element that may have holes therein, in accordance with the present invention.

FIG. 34 illustrations (a)-(c) show various geometries of an optical identification element that may have teeth thereon, in accordance with the present invention.

FIG. 35 illustrations (a)-(c) show various geometries of an optical identification element, in accordance with the present invention.

FIG. 36 is a side view an optical identification element having a reflective coating thereon, in accordance with the present invention.

FIG. 37 illustrations (a)-(b) are side views of an optical identification element polarized along an electric or magnetic field, in accordance with the present invention.

FIG. 51(a) show an embodiment of a disk cytometer having radial channels for spin drying in accordance with the invention.

FIG. 51(b) show an alternative embodiment of a disk cytometer having a mechanical iris for providing a variable aperture for bead access to grooves in accordance with the invention.

BEST MODE FOR CARRYING OUT THE INVENTION

Figure 1:
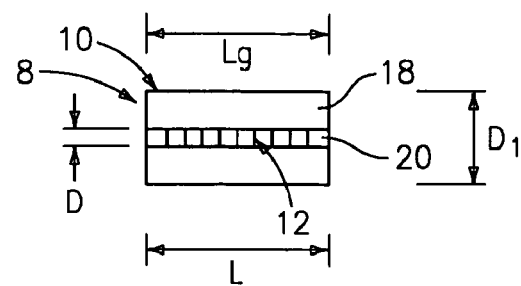
FIG. 1 is a side view of an optical identification element, in accordance with the present invention.

Referring to FIG. 1, a hybrid random bead/chip based microarray includes a diffraction grating-based optical identification element 8 (or encoded element or coded element) which comprises a known optical substrate 10, having an optical diffraction grating 12 disposed (or written, impressed, embedded, imprinted, etched, grown, deposited or otherwise formed) in the volume of or on a surface of a substrate 10. The grating 12 is a periodic or aperiodic variation in the effective refractive index and/or effective optical absorption of at least a portion of the substrate 10.

The optical identification element 8 described herein is similar to that described in Copending U.S. patent application Ser. No. 10/661,234, filed Sep. 12, 2003, entitled "Diffraction Grating-Based Optical Identification Element", which is incorporated herein by reference in its entirety.

In particular, the substrate 10 has an inner region 20 where the grating 12 is located. The inner region 20 may be photosensitive to allow the writing or impressing of the grating 12. The substrate 10 has an outer region 18, which does not have the grating 12 therein.

The grating 12 is a combination of one or more individual spatial periodic sinusoidal variations (or components) in the refractive index that are collocated at substantially the same location on the substrate 10 along the length of the grating region 20, each having a spatial period (or pitch) Λ. The resultant combination of these individual pitches is the grating 12, comprising spatial periods (Λ1-Λn) each representing a bit in the code. Thus, the grating 12 represents a unique optically readable code, made up of bits, where a bit corresponds to a unique pitch Λ within the grating 12. Accordingly, for a digital binary (0-1) code, the code is determined by which spatial periods (Λ1-Λn) exist (or do not exist) in a given composite grating 12. The code or bits may also be determined by additional parameters (or additional degrees of multiplexing), and other numerical bases for the code may be used, as discussed herein and/or in the aforementioned patent application.

The grating 12 may also be referred to herein as a composite or collocated grating. Also, the grating 12 may be referred to as a "hologram", as the grating 12 transforms, translates, or filters an input optical signal to a predetermined desired optical output pattern or signal.

The substrate 10 has an outer diameter D1 and comprises silica glass ($SiO_2$) having the appropriate chemical composition to allow the grating 12 to be disposed therein or thereon. Other materials for the optical substrate 10 may be used if desired. For example, the substrate 10 may be made of any glass, e.g., silica, phosphate glass, borosilicate glass, or other glasses, or made of glass and plastic, or solely plastic. For high temperature or harsh chemical applications, the optical substrate 10 made of a glass material is desirable. If a flexible substrate is needed, plastic, rubber or polymer-based substrate may be used. The optical substrate 10 may be any material capable of having the grating 12 disposed in the grating region 20 and that allows light to pass through it to allow the code to be optically read.

The optical substrate 10 with the grating 12 has a length L and an outer diameter D1, and the inner region 20 diameter D. The length L can range from very small "microbeads" (or microelements, micro-particles, or encoded particles), about 1-1000 microns or smaller, to larger "macroelements" for larger applications (about 1.0-1000 mm or greater). In addition, the outer dimension D1 can range from small (less than 1000 microns) to large (1.0-1000 mm and greater). Other dimensions and lengths for the substrate 10 and the grating 12 may be used.

The grating 12 may have a length Lg of about the length L of the substrate 10. Alternatively, the length Lg of the grating 12 may be shorter than the total length L of the substrate 10.

The outer region 18 is made of pure silica ($SiO_2$) and has a refractive index n2 of about 1.458 (at a wavelength of about 1553 nm), and the inner grating region 20 of the substrate 10 has dopants, such as germanium and/or boron, to provide a refractive index n1 of about 1.453, which is less than that of outer region 18 by about 0.005. Other indices of refraction n1,n2 for the grating region 20 and the outer region 18, respectively, may be used, if desired, provided the grating 12 can be impressed in the desired grating region 20. For example, the grating region 20 may have an index of refraction that is larger than that of the outer region 18 or grating region 20 may have the same index of refraction as the outer region 18 if desired.

Figure 2:
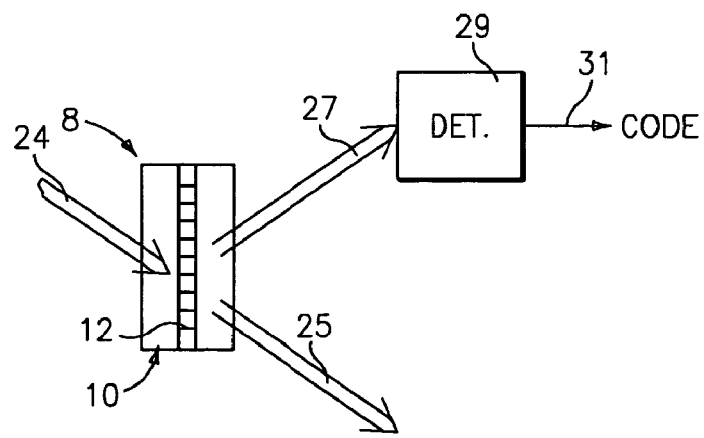
FIG. 2 is a top level optical schematic for reading a code in an optical identification element, in accordance with the present invention.

Referring to FIG. 2, an incident light 24 of a wavelength λ, e.g., 532 nm from a known frequency doubled Nd:YAG laser or 632 nm from a known Helium-Neon laser, is incident on the grating 12 in the substrate 10. Any other input wavelength λ can be used if desired provided λ is within the optical transmission range of the substrate (discussed more herein and/or in the aforementioned patent application). A portion of the input light 24 passes straight through the grating 12, as indicated by a line 25. The remainder of the input light 24 is reflected by the grating 12, as indicated by a line 27 and provided to a detector 29. The output light 27 may be a plurality of beams, each having the same wavelength λ as the input wavelength λ and each having a different output angle indicative of the pitches (Λ1-Λn) existing in the grating 12. Alternatively, the input light 24 may be a plurality of wavelengths and the output light 27 may have a plurality of wavelengths indicative of the pitches (Λ1-Λn) existing in the grating 12. Alternatively, the output light may be a combination of wavelengths and output angles. The above techniques are discussed in more detail herein and/or in the aforementioned patent application.

The detector 29 has the necessary optics, electronics, software and/or firmware to perform the functions described herein. In particular, the detector reads the optical signal 27 diffracted or reflected from the grating 12 and determines the code based on the pitches present or the optical pattern, as discussed more herein or in the aforementioned patent application. An output signal indicative of the code is provided on a line 31.

Figure 6:
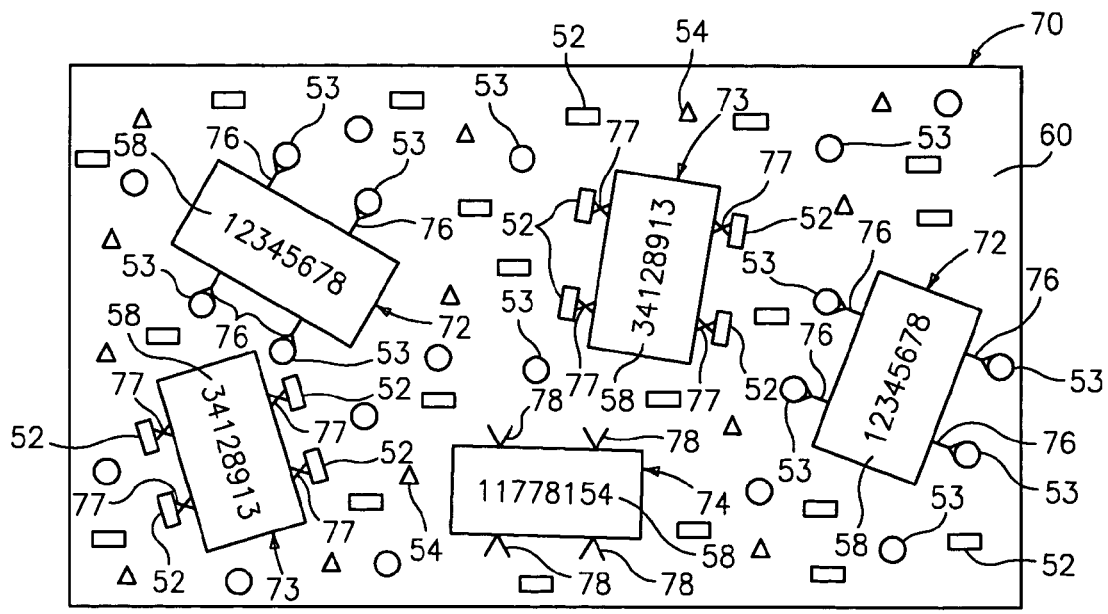
FIG. 6 is a schematic view of a plurality of optical identification elements having different identification or codes and coated with different probe substances disposed in a cell with a plurality of test substances, in accordance with the present invention.

Referring to FIGS. 3-8, and FIG. 3(a), the substrate 10 of the optical identification element (or microbead) 8 may be functionalized by coating or attaching a desired probe 76, such as a compound, chemical or molecule, which is then used in an assay as an attractant for certain complimentary compounds, chemicals or molecules, otherwise known as a "target" analyte 52-54 (see FIG. 6). This capability to uniquely encode a large number of microbeads 8 with a corresponding unique probe 76 attached thereto enables these functionalized microbeads 72 to be mixed with unknown "target" analytes 52-54 to perform a multiplexed experiment.

Figure 3:
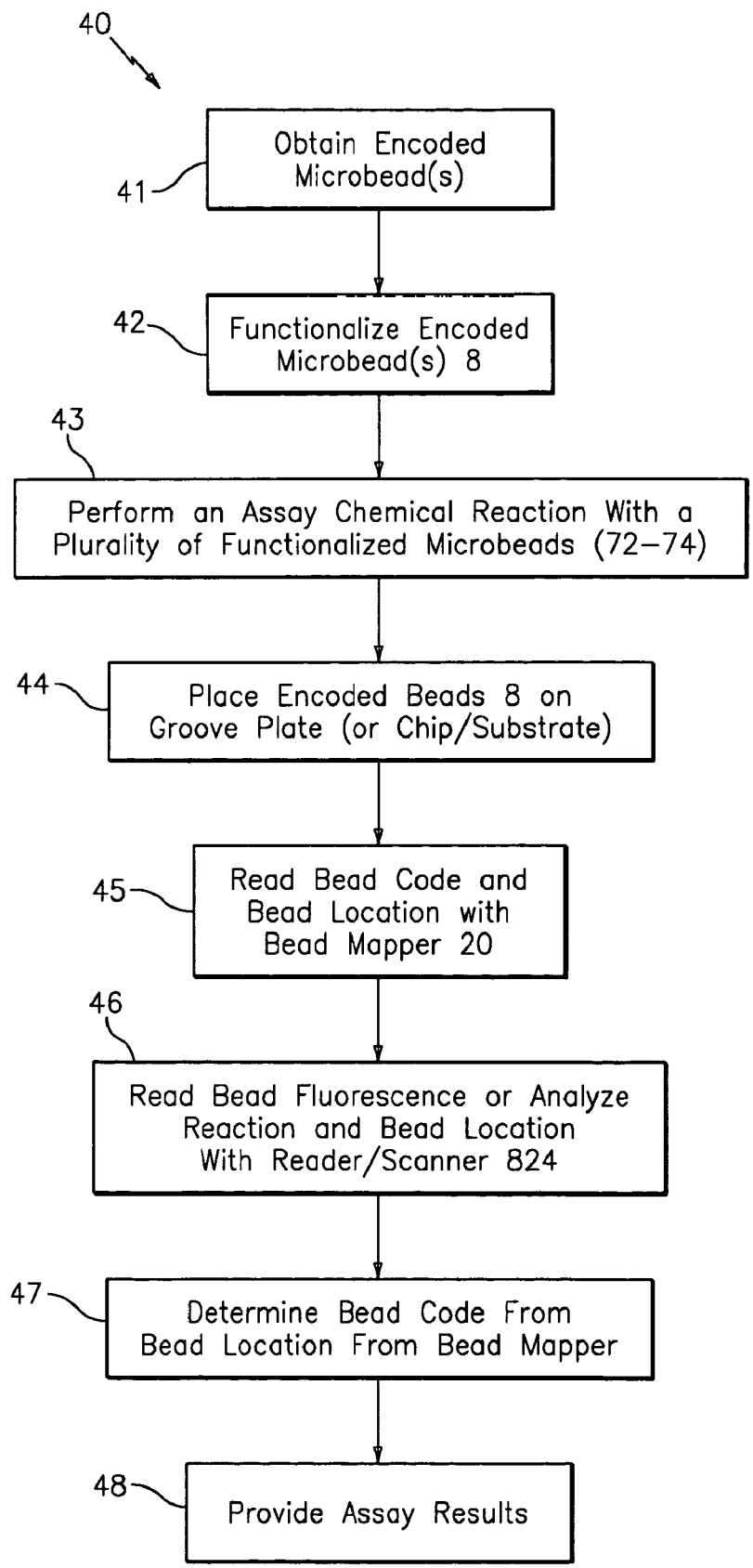
FIG. 3 is a flow chart of a method of using a hybrid random bead/ship based microarray, in accordance with the present invention.
Figure 3A:
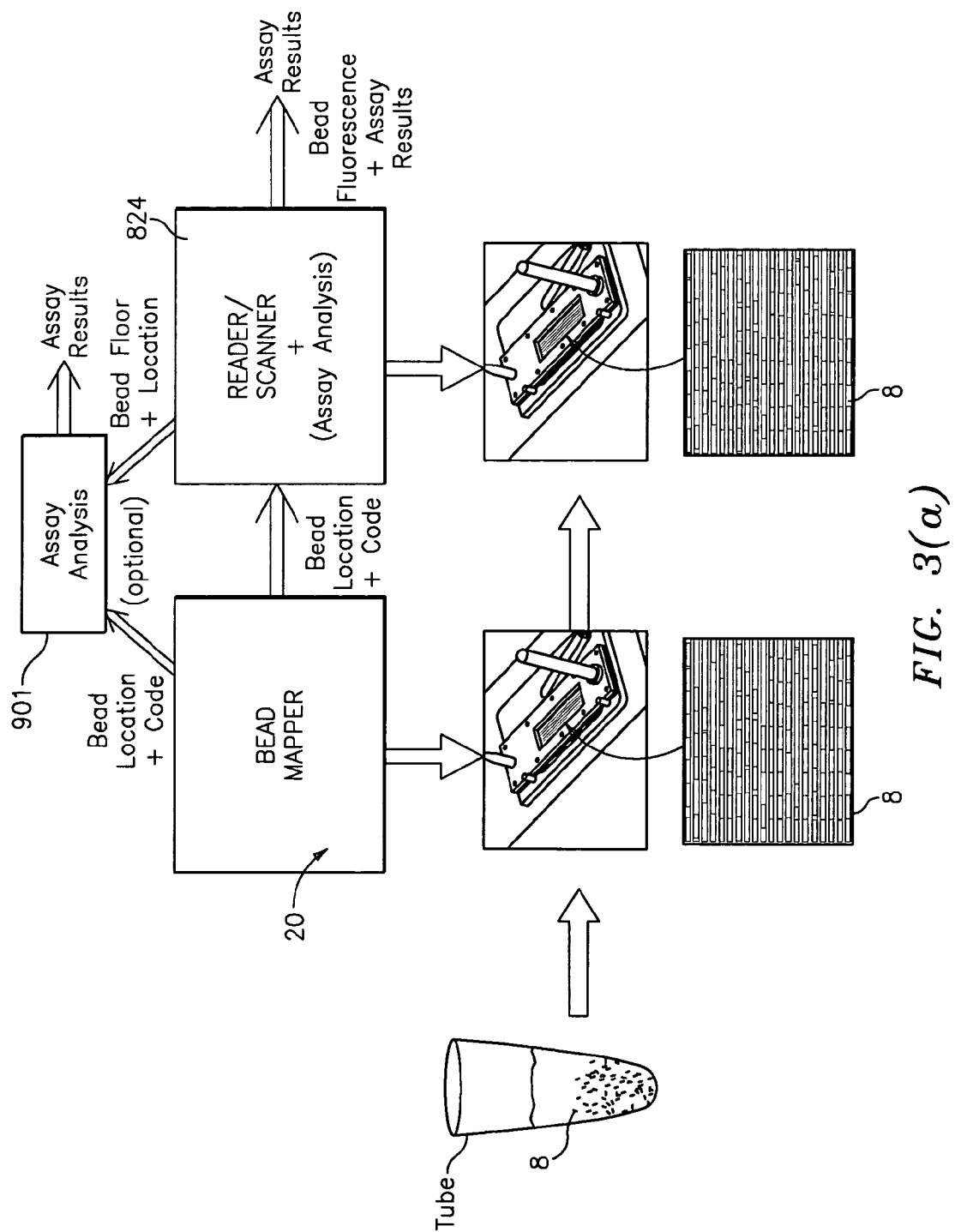
FIG. 3(a) is a schematic pictorial representation showing a way to use a hybrid random bead/ship based microarray, in accordance with the present invention.

Referring to FIGS. 3 and 3(a), a procedure 40 for performing such a multiplexed assay or experiment using the hybrid random bead/chip based microarray includes the steps of obtaining (step 41) the microbead 8, as described herein, and functionalizing (step 42) the substrate 10 of the microbead 8 by coating or depositing or growing it with a probe 76 that will react in a predetermined way with "target" analytes 52-54. An assay is then performed (step 43) with a plurality of functionalized microbeads 72 with different identification codes 58 at the same time, e.g., analyte reaction or hybridization, or other multiplexed chemical reaction or experiment. In step 44, the microbeads 8 are then placed on a plate, chip or other 2D substrate (as discussed herein), which may be contained within a housing, chamber or the like (as discussed herein). In step 45, the chip is provided to a Bead Mapper (as discussed herein) which reads the bead codes and bead locations on the chip.

Next, in step 46, the chip is provided to a Reader/Scanner 824 (FIG. 3(a)) where the fluorescence of each of the functionalized/hybridized/reacted microbeads 72 is analyzed to determine information about the analyte reaction or hybridization for each bead and location. Next a step 47 determines the code 58 of each of the beads 72 from the information from the Bead Mapper, thereby determine which "target" analytes 52-54 are present in the solution 60. The assay results are provided in step 48.

Accordingly, as discussed hereinabove, the assay utilizes the fact that each probe particle (or microbead) is individually identifiable. Once the bead identification code or tag is read, and the spatial position (or location) is known, the self-assembled "chip" can be inserted into a conventional known chip reader or scanner 824 (FIG. 3(a)). The chip reader 824 reads the fluorescent tags on the target molecules and determines the spatial location of these tags. The fluorescent tag location is then used to identify the bead code (and thus probe identification) at that location from the bead mapping information to complete the assay or chemical experiment.

Examples of known chip readers include the following: Axon Gene Pix Pro 4100 A, GSI/Lumonics/Perkin Elmer Scanner, Alpha Inatech, and others. Other commercial readers or scanners now known or later developed may be used provided it can detect the desired analyte reaction parameter, e.g., fluorescence, etc., and the it can provide the location of same on the substrate.

Alternatively, the reader/scanner 824 may be similar to the analyte reaction reading and analysis portions of the microbead reader device described in Copending Provisional Patent Applications, Ser. No. 60/512,302, entitled "Optical Reader for Diffraction Grating Based Encoded Microbeads", filed Oct. 17, 2003; Ser. No. 60/513,053, filed Oct. 21, 2003, "Optical Reader for Diffraction Grating Based Encoded Microbeads"; Ser. No. 60/508,038, "Optical Reader for Diffraction Grating Based Encoded Microbeads", filed Oct. 1, 2003, all of which are incorporated herein by reference in their entirety.

Similarly, the Bead Mapper 20 may be similar to the bead reading/mapping portions of the microbead reader described in Copending Provisional Patent Applications, Ser. No. 60/512,302, entitled "Optical Reader for Diffraction Grating Based Encoded Microbeads", filed Oct. 17, 2003; Ser. No. 60/513,053, filed Oct. 21, 2003, "Optical Reader for Diffraction Grating Based Encoded Microbeads"; Ser. No. 60/508,038, "Optical Reader for Diffraction Grating Based Encoded Microbeads", filed Oct. 1, 2003, all of which are incorporated herein by reference in their entirety.

Figures 4, 5:
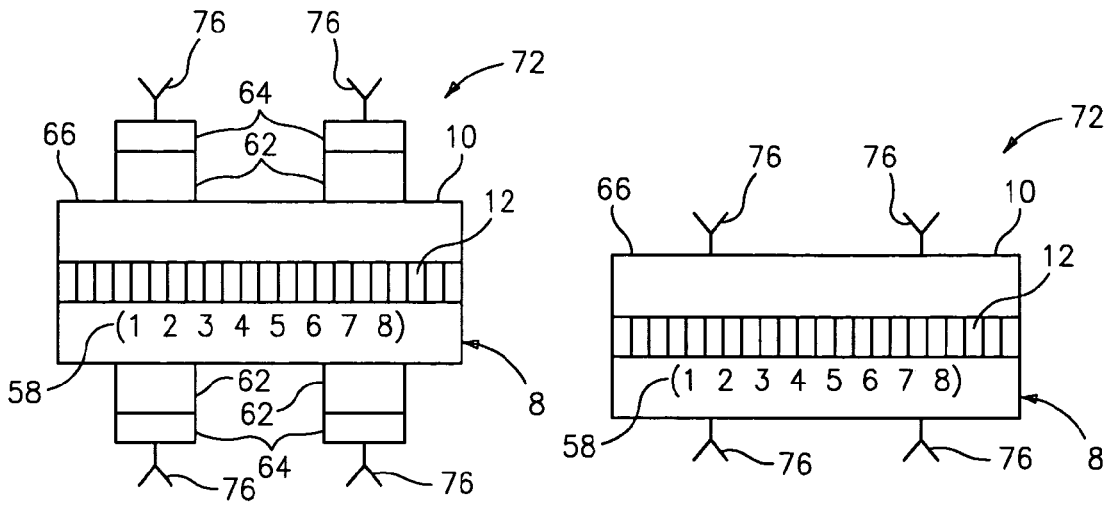
FIG. 4 is a side view of an optical identification element having a substance attached to the outer surface thereof, in accordance with the present invention.
FIG. 5 is a side view of an optical identification element having a substance attached to the outer surface thereof, in accordance with the present invention.

In FIGS. 4 and 5, a functionalized microbead 72 is shown, wherein the substrate 10 of the microbead 8 is coated with a probe 76 and used in an assay or as an attractant for certain "target" analytes 52-54 (see FIG. 6). In one embodiment shown in FIG. 4, the microbead 8 is coated with a linker molecule or complex 62 as is known in the art. A molecular group 64 is attached to the probe 76 to enable the probe to be bonded to the linker molecule or complex 62, and thus to the microbead 8 to form the functionalized microbead 72. The probe 76 may include one of an Oligonucleitides (oligos), antibodies, peptides, amino acid strings, cDNA, RNA, chemicals, nucleic acid oligomers, polymers, biological cells, or proteins. For example, the probe 76 may comprise a single strand of DNA (or portion thereof) and the "target" analyte 52-54 comprises at least one unknown single strand of DNA, wherein each different "target" analyte has a different DNA sequence.

Referring to FIG. 5, in some instances, the probe 76 may be attached directly to the substrate 10 of the microbead 8, or directly synthesized (or grown) thereon, such as via phosphoramidite chemistry. Examples of surface chemistry for the functionalized microbeads 72 include Streptavidin/biotinylated oligos and Aldehyde/amine modified oligos. Other chemistry may be used if desired. Some examples of chemistry are described in Copending Provisional U.S. Patent Application Ser. No. 60/519,932, filed Nov. 14, 2003, entitled, "Diffraction Grating-Based Encoded Microparticles for Multiplexed Experiments", which is incorporated herein by reference in its entirety. Further, the microbead may be coated with a blocker of non-specific binding (e.g., salmon sperm DNA) to prevent bonding of analytes 52-54 (e.g. DNA) to the non-functionalized surface 66 of the functionalized microbeads 72.

For example, DNA probe molecules may be directly synthesized on the beads using standard phosphoramidite chemistry with no post synthetic purification, and the beads used as the solid support. The attachment to the bead may be done by preparing the beads using standard linker chemistry coated on the beads that allows the probe to attach to the bead. Then, the oligo probe may be grown base-by-base to create the oligo sequence. Alternatively, the entire desired oligo sequence may be pre-fabricated and then attached to the bead after fabrication. In that case, the linker chemistry used on the bead would likely be different and possibly more complex than the linker chemistry used in direct synthesis. Also, the beads may be functionalized as discussed hereinbefore and then placed in a blocker solution of BSA Bovine Serum Albumin (or any other suitable blocker to prevent non-specific binding of the target molecule). The beads may then be hybridized by placing the beads in a hybridization solution. Any desirable hybridization solution may be used. One example is: 5× concentration of SSC (Standard Saline Citrate), 25% formamide, 0.1% SDS (Sodium Dodecyl Sulfate-soap—used to help the beads not stick to the walls of tube), a predetermined amount of complementary DNA (cDNA) to the sequence of a given Probe tagged with Cy3 fluorescent molecules, and a predetermined amount of complementary DNA (cDNA) to the sequence of that Probe tagged with Cy5 fluorescent molecules. Any other hybridization or analyte reaction technique may be used if desired.

Referring to FIG. 6, an assay is performed by adding a solution 60 of different types of "target" analytes 52-54 into a cell or container 70 having a plurality of functionalized microbeads 72-74 disposed therein. As discussed in step 46 of FIG. 3, the functionalized microbeads 72-74 placed in the cell 70 have different identification codes 58 that correspond to unique probes 76-78 bonded thereto. For example, all functionalized microbeads 72 disposed within the cell 70 having an identification code of 12345678 is coated with a unique probe 76. All functionalized microbeads 73 disposed within the cell 72 having an identification code of 34128913 is coated with a unique probe 77. All functionalized microbeads 77 disposed within the cell 70 having an identification code of 11778154 is coated with a unique probe 78.

The "target" analytes 52-54 within the solution 60 are then mixed with the functionalized microbeads 72-74. During the mixing of the "target" analytes 52-54 and the functionalized microbeads 72-74, the "target" analytes attach to the complementary probes 76-78, as shown for functionalized microbeads 72,73 having codes 12345678 and 34128913. Specifically, as shown in FIG. 6, "target" analytes 53 bonded with probes 76 of the functionalized microbeads 72 having the code 12345678, and "target" analytes 52 bonded with probes 77 of the functionalized microbeads 73 having the code 34128913. On the other hand, "target" analytes 54 did not bond with any probes, and no "target" analytes 52-54 in the solution 60 bonded with probes 78 of the functionalized microbeads 74 having the code 11778154. Consequently, knowing which "target" analytes attach to which probes along with the capability of identifying each probe by the encoded microbead, the results of the assay would show that the unknown "target" analytes in the solution 60 includes "target" analytes 53, 54, as will be described in further detail.

For example as discussed hereinbefore, each coded functionalized microbead 72-74 has a unique probe 76-78, respectively bonded thereto, such as a portion of a single strand of DNA. Similarly, the "target" analytes 52-54 comprise a plurality of unknown and unique single strands of DNA. These "target" analytes 52-54 are also processed with a fluorescent, such as dyeing, such that the test molecules illuminate. As will be discussed hereinafter, the fluorescence of the "target" analytes provide the means to identify, which functionalized microbeads 72-74 have a "target" analyte attached thereto.

Once the reaction or combining or hybridization is complete, the functionalized (or reacted or hybridized) microbeads 72-74 are rinsed off with a saline solution to clean off the uncombined "target" analytes 52-54.

Figure 7:
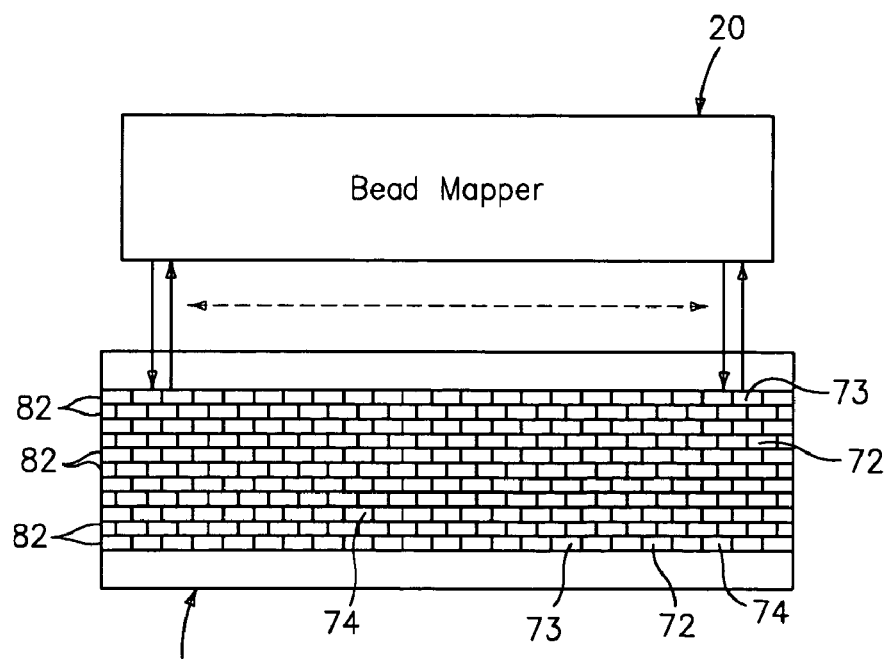
FIG. 7 is a schematic view of plurality of optical identification elements, aligned in a plurality of grooves, disposed on a substrate, and a Bead Mapper that scans each optical identification element for determining the code and location of each optical identification element, in accordance with the present invention.

Referring to FIG. 7, as discussed herein, the functionalized microbeads 72-74 may be placed on a tray, plate, or substrate (or "chip") 84 with grooves 82 to allow the microbeads to be aligned in a predetermined direction, such as that described in U.S. patent application Ser. No. 10/661,234, filed Sep. 12, 2003, and U.S. patent application Ser. No. 10/661,836, filed Sep. 12, 2003, which are both incorporated herein by reference. The grooves 82 may have holes (not shown) that provide suction to keep the functionalized microbeads in position. Once aligned in the tray 84, the functionalized microbeads 52-54 are individually scanned and analyzed by the bead detector 20.

Figure 8:
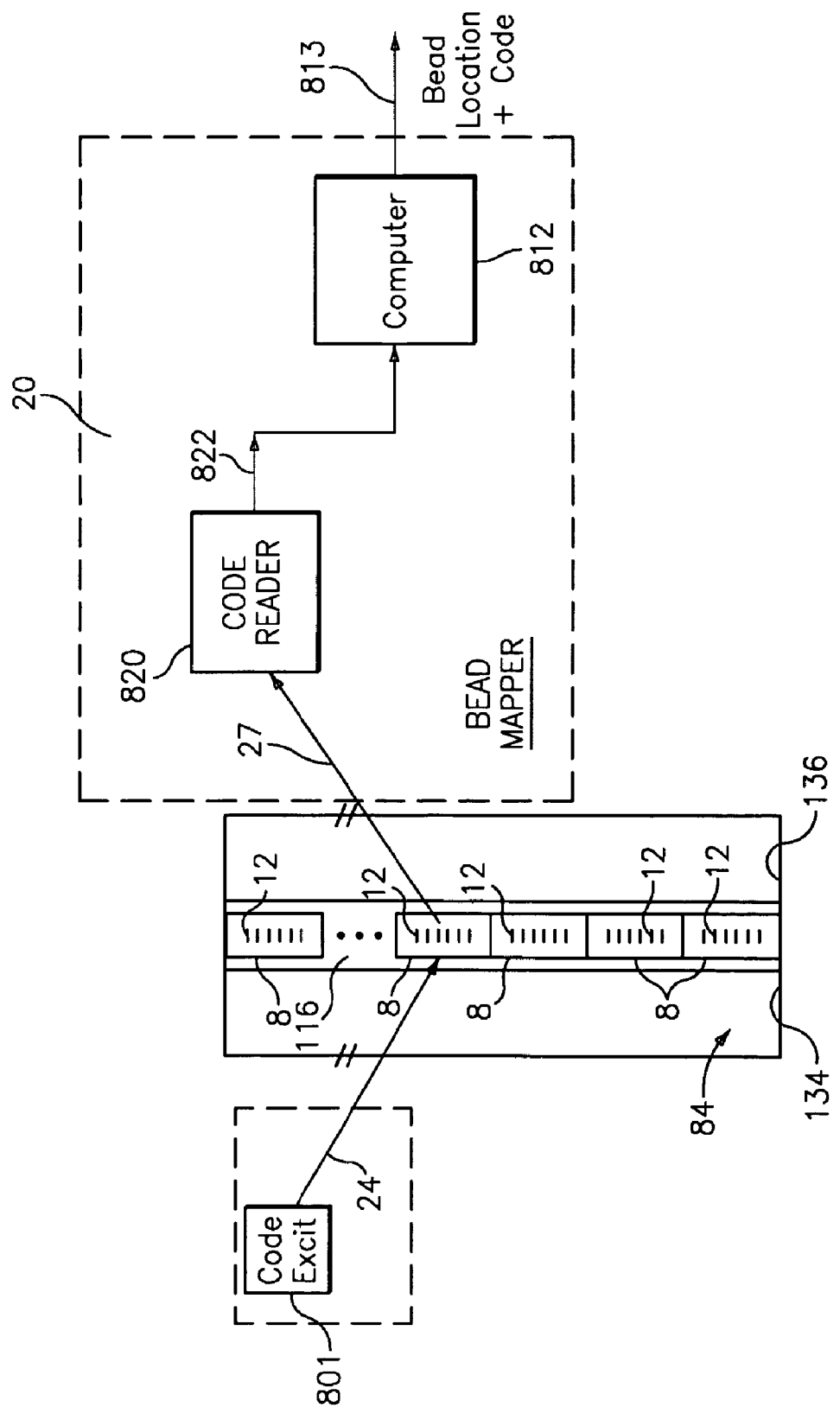
FIG. 8 is a side view of an optical identification element, and a more detailed view of a Bead Mapper that determines the code and location of the optical identification element, in accordance with the present invention.

Referring to FIGS. 7 and 8, then, each functionalized microbead 72-74 is read by a Bead Mapper 201 to determine the identification code 58 of each of the functionalized microbeads and the location of each bead.

Referring to FIG. 8, more specifically, as discussed herein and in the aforementioned patent applications, the codes in the microbeads 8 are detected when illuminated by incident light 24 from a code excite optical signal device 801 which produces a diffracted or output light signal 27 to a reader 820, which includes the optics and electronics necessary to read the codes in each bead 8, as described herein and/or in the aforementioned copending patent application. The reader 820 provides a signal on a line 822 indicative of the code in each of the bead 8 to a known computer 812. The incident light 24 may be directed transversely from the side of the tray 84 (or from an end or any other angle) with a narrow band (single wavelength) and/or multiple wavelength source, in which case the code is represented by a spatial distribution of light and/or a wavelength spectrum, respectively, as described hereinafter and in the aforementioned copending patent application. Other illumination, readout techniques, types of gratings, geometries, materials, etc. may be used for the microbeads 8, as discussed hereinafter and in the aforementioned patent application. The computer 812 provides an output signal on a line 813 indicative of the bead location and code.

Figure 9:
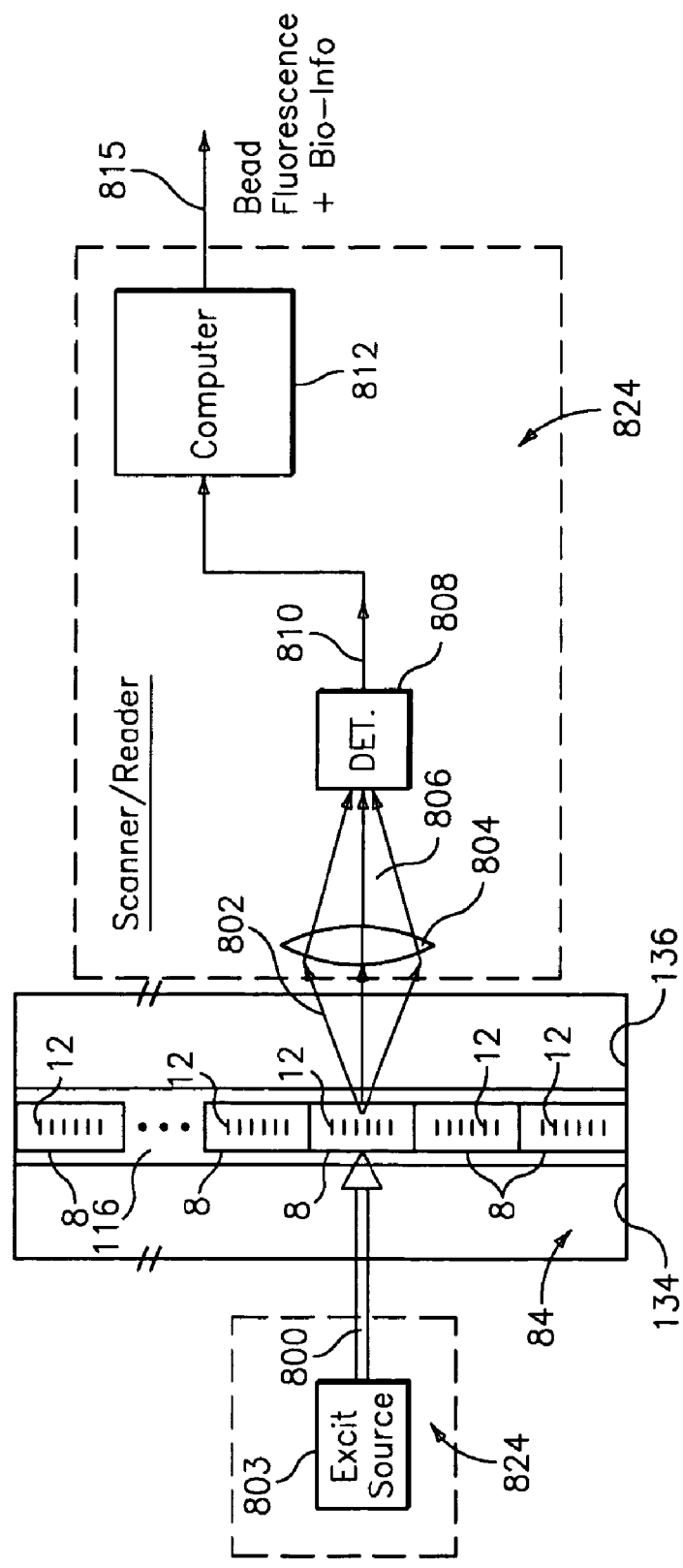
FIG. 9 is a side view of an optical identification element after the performance of an assay, and a more detailed view of a Reader/Scanner that reads the fluorescence and location of the optical identification element, in accordance with the present invention.
Figure 10:
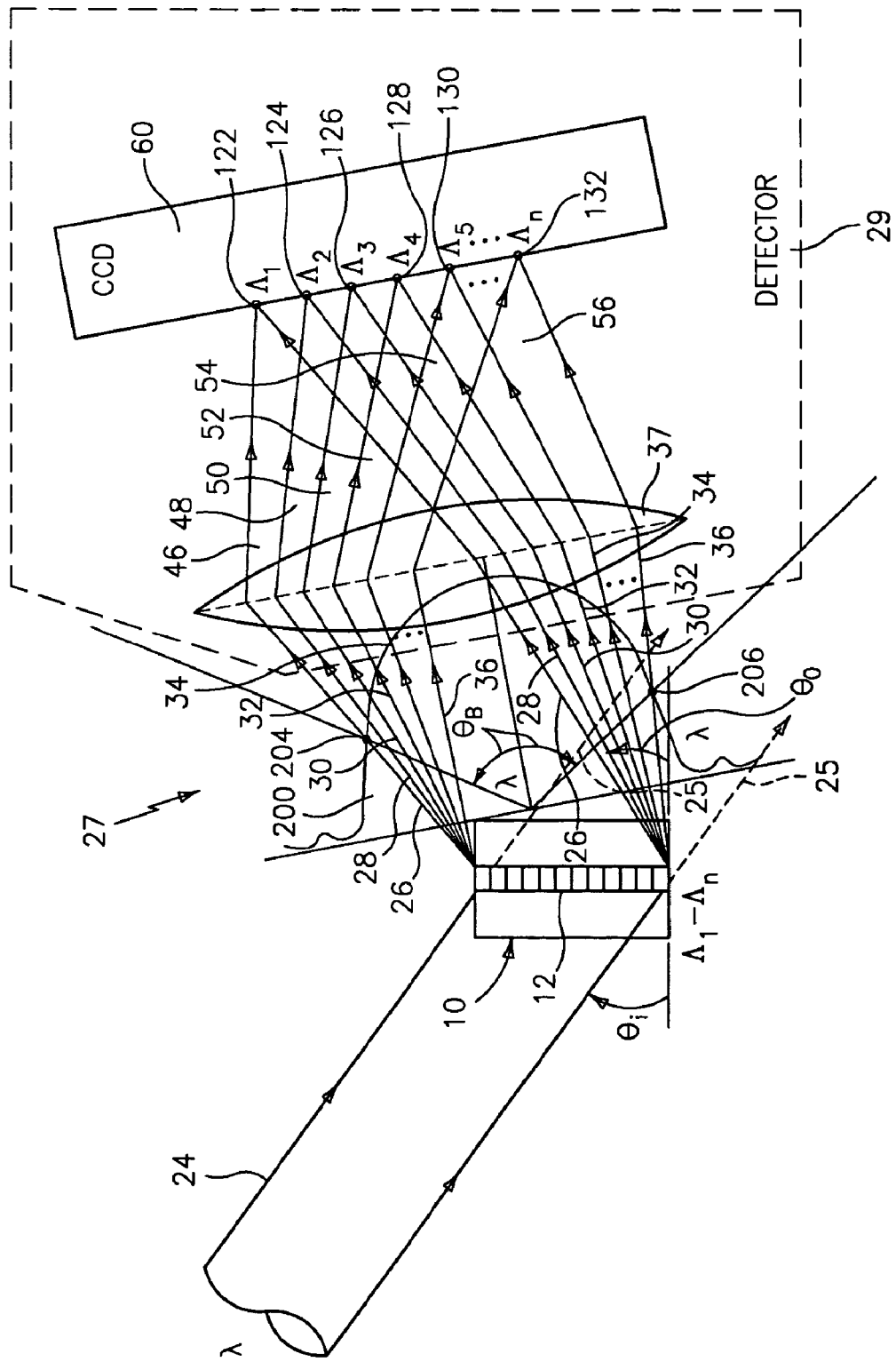
FIG. 10 is an optical schematic for reading a code in an optical identification element, in accordance with the present invention.

Referring to FIGS. 8-10, the slide, tray or chip 84 is then placed in a reader or scanner 824 (also see FIG. 3(a)). The reader 824 reads each functionalized microbead 72-74 (FIGS. 4-7) for fluorescence or other indicator of the analyte reaction.

In FIG. 7-10, a light source 803 may be provided to luminate the microbeads 72-74, also shown as element 8 in FIGS. 8-9. Once the fluorescent microbeads 72-74 are identified and knowing which probe 76-78 (or single strand of DNA) was attached to each coded, functionalized microbead 72-74, the bead detector 808 determines which "target" analytes 52-54 were present in the solution 60 (see FIG. 6). As described hereinbefore, the bead detector 808 illuminates the functionalized microbeads 72-74 and focuses light 26 (FIG. 10) reflected by the diffraction grating 12 onto a CCD array or camera 61, whereby the code 58 of the functionalized microbead 72-74 is determined. Secondly, the reader 824 includes a fluorescence detector 86 for measuring the fluorescence emanating from "target" analytes 52-54 attached to the probes 76-78. The scanner/reader 824 includes a lens 804 and optical fiber (not shown) for receiving and providing the fluorescence from the "target" analyte 52-54 to the fluorescence meter or detector 808.

Referring to FIGS. 8-10, for assays that use fluorescent molecule markers to label or tag chemicals, an optical excitation signal 800 is incident on the microbeads 8 through the tray 84 and a fluorescent optical output signal 806 emanates from the beads 8 that have the fluorescent molecule attached. The fluorescent optical output signal 806 passes through a lens 804, which provides focused light 802 to a known optical fluorescence detector 808. Instead of or in addition to the lens 804, other imaging optics may be used to provide the desired characteristics of the optical image/signal onto the fluorescence detector 808. The detector 808 provides an output signal on a line 810 indicative of the amount of fluorescence on a given bead 8, which can then be interpreted to determine what type of chemical is attached to the bead 8.

The tray 84 is made of glass or plastic or any material that is transparent to the code reading incident beam 24 and code reading output light beams 27 as well as the fluorescent excitation beam 800 and the output fluorescent optical signal 802, and is properly suited for the desired application or experiment, e.g., temperature range, harsh chemicals, or other application specific requirements.

The code signal 822 from the bead code reader 820 and the fluorescent signal 810 from the fluorescence detector are provided to a known computer 812. The computer reads the code associated with each bead and determines the chemical probe that was attached thereto from a predetermined table that correlates a predetermined relationship between the bead code and the attached probes. In addition, the computer 812 reads the fluorescence associated with each bead and determines the sample or analyte that is attached to the bead from a predetermined data that correlates a predetermined relationship between the fluorescence tag and the analyte attached thereto. The computer 812 then determines information about the analyte and/or the probe as well as about the bonding of the analyte to the probe, and provides such information on a display, printout, storage medium or other interface to an operator, scientist or database for review and/or analysis, as indicated by a line 815.

Generally, the assay of the present invention may be used to carry out any binding assay or screen involving immobilization of one of the binding agents. Such solid-phase assays or screens are well known in the chemical and biochemical arts. For example, such screening may involve specific binding of cells to a molecule (e.g. an antibody or antigen) immobilized on a microbead in the assay followed by analysis to detect whether or to what extent binding occurs. Alternatively, the beads may subsequently removed from the groove plate for sorting and analysis via flow cytometry (see e.g. by Needels et al, Proc. Natl. Acad. Sci. USA, Vol. 90, pp. 10700-10704, November 1993). Examples of biological compounds that may be assayed or screened using the assay of the present invention include, e.g. agonists and antagonists for cell membrane receptors, toxins, venoms, viral epitopes, hormones, sugars, cofactors, peptides, enzyme substrates, drugs inclusive of opiates and steroids, proteins including antibodies, monoclonal antibodies, antisera reactive with specific antigenic determinants, nucleic acids, lectins, polysaccharides, cellular membranes and organelles. In addition, the present invention may be used in any of a large number of well-known hybridization assays where nucleic acids are immobilized on a surface of a substrate, e.g. genotyping, polymorphism detection, gene expression analysis, fingerprinting, and other methods of DNA- or RNA-based sample analysis or diagnosis.

Any of the great number of isotopic and non-isotopic labeling and detection methods well-known in the chemical and biochemical assay art may be used to detect binding with the present invention. Alternatively, spectroscopic methods well-known in the art may be used to determine directly whether a molecule is bound to a surface coating in a desired configuration. Spectroscopic methods include e.g., UV-VIS, NMR, EPR, IR, Raman, mass spectrometry and other methods well-known in the art. For example, mass spectrometry also is now widely employed for the analysis of biological macromolecules. The method typically involves immobilization of a protein on a surface of substrate where it is then exposed to a ligand binding interaction. Following ligand binding (or non-binding) the molecule is desorbed from the surface and into a spectrometer using a laser (see, e.g. Merchant and Weinberger, "Recent advancements in surface-enhanced laser desorption/ionization-time of flight-mass spectrometry," Electrophoresis 21:1164-1177 (2000)). The microbeads in the assay of the present invention may be used as substrates in the mass spectrometry detection methods described above.

Various aspects of the present invention may be conducted in an automated or semi-automated manner, generally with the assistance of well-known data processing methods. Computer programs and other data processing methods well known in the art may be used to store information including e.g. microbead identifiers, probe sequence information, sample information, and binding signal intensities. Data processing methods well known in the art may be used to read input data covering the desired characteristics.

The invention may be used in many areas such as drug discovery, functionalized substrates, biology, proteomics, combinatorial chemistry, DNA analysis/tracking/sorting/tagging, as well as tagging of molecules, biological particles, matrix support materials, immunoassays, receptor binding assays, scintillation proximity assays, radioactive or non-radioactive proximity assays, and other assays, (including fluorescent, mass spectroscopy), high throughput drug/genome screening, and/or massively parallel assay applications. The invention provides uniquely identifiable beads with reaction supports by active coatings for reaction tracking to perform multiplexed experiments.

Some current techniques used in combinatorial chemistry or biochemistry are described in U.S. Pat. No. 6,294,327, entitled "Apparatus and Method for Detecting Samples Labeled With Material Having Strong Light Scattering Properties, Using Reflection Mode Light and Diffuse Scattering", issued Sep. 23, 2001 to Walton et al.; U.S. Pat. No. 6,242,180, entitled "Computer Aided Visualization and Analysis System for Sequence Evaluation", issued Jun. 5, 2001, to Chee; U.S. Pat. No. 6,309,823 entitled "Arrays of Nucleic Acid Probes for Analyzing Biotransformation of Genes and Methods of Using the Same", Oct. 30, 2001, to Cronin et al.; U.S. Pat. No. 6,440,667, entitled "Analysis of Target Molecules Using an Encoding System"; U.S. Pat. No. 6,355,432, entitled "Products for Detecting Nucleic Acids"; U.S. Pat. No. 6,197,506, entitled "Method of Detecting Nucleic Acids"; U.S. Pat. No. 6,309,822, entitled "Method for comparing copy number of nucleic acid sequences"; U.S. Pat. No. 5,547,839, entitled "Sequencing of surface immobilized polymers utilizing micro-fluorescence detection", U.S. Pat. No. 6,383,754, entitled "Binary Encoded Sequence Tags", and U.S. Pat. Nos. 6,261,782 and 6,667,121, entitled "Fixed Address Analysis of Sequence Tags", which are all incorporated herein by reference to the extent needed to understand the present invention.

The invention can be used in combinatorial chemistry, active coating and functionalized polymers, as well as immunoassays, and hybridization reactions. The invention enables millions of parallel chemical reactions, enable large-scale repeated chemical reactions, increase productivity and reduce time-to-market for drug and other material development industries.

As discussed hereinbefore, although a fluorescent label is probably most convenient, other sorts of labels, e.g., radioactive, enzyme linked, optically detectable, or spectroscopic labels may be used. An appropriate detection method applicable to the selected labeling method can be selected. Suitable labels include radionucleotides, enzymes, substrates, cofactors, inhibitors, magnetic particles, heavy metal atoms, and particularly fluorescers, chemiluminescers, and spectroscopic labels. Patents teaching the use of such labels include U.S. Pat. Nos. 3,817,837; 3,850,752; 3,939,350; 3,996,345; 4,277,437; 4,275,149; and 4,366,241.

With an appropriate label selected, the detection system best adapted for high resolution and high sensitivity detection may be selected. As indicated above, an optically detectable system, e.g., fluorescence or chemilumnescence would be preferred but is not required. Other detection systems may be adapted to the purpose, e.g., electron microscopy, scanning electron microscopy (SEM), scanning tunneling electron microscopy (STEM), infrared microscopy, atomic force microscopy (AFM), electrical conductance, and image plate transfer.

Referring to FIG. 10, the reflected light 27, comprises a plurality of beams 26-36 that pass through a lens 37, which provides focused light beams 46-56, respectively, which are imaged onto a CCD camera 61. The lens 37 and the camera 61, and any other necessary electronics or optics for performing the functions described herein, make up the reader/detector 808. Instead of or in addition to the lens 37, other imaging optics may be used to provide the desired characteristics of the optical image/signal onto the camera 61 (e.g., spots, lines, circles, ovals, etc.), depending on the shape of the substrate 10 and input optical signals. Also, instead of a CCD camera other devices may be used to read/capture the output light.

Figure 11:
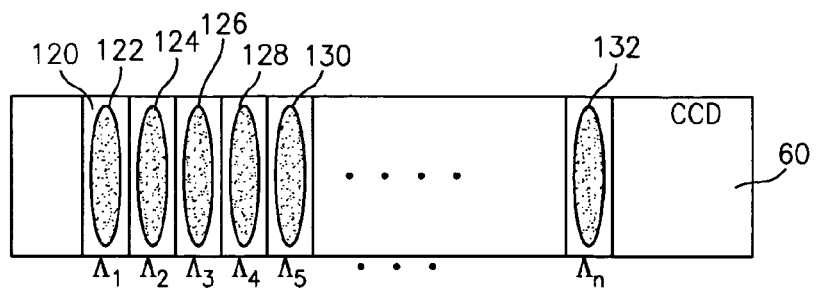
FIG. 11 is an image of a code on a CCD camera from an optical identification element, in accordance with the present invention.
Figure 12:
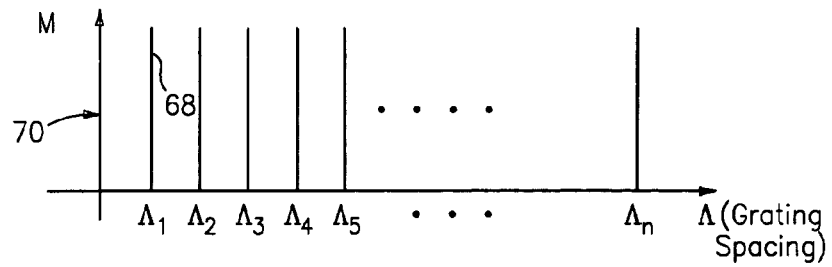
FIG. 12 is a graph showing an digital representation of bits in a code in an optical identification element, in accordance with the present invention.

Referring to FIG. 11, the image on the CCD camera 60 is a series of illuminated stripes indicating ones and zeros of a digital pattern or code of the grating 12 in the element 8. Referring to FIG. 12, lines 68 on a graph 70 are indicative of a digitized version of the image of FIG. 11 as indicated in spatial periods ($\Lambda 1$-$\Lambda n$).

Each of the individual spatial periods ($\Lambda 1$-$\Lambda n$) in the grating 12 is slightly different, thus producing an array of N unique diffraction conditions (or diffraction angles) discussed more hereinafter. When the element 8 is illuminated from the side, in the region of the grating 12, at an appropriate input angle, e.g., about 30 degrees, with a single input wavelength $\lambda$ (monochromatic) source, the diffracted (or reflected) beams 26-36 are generated. Other input angles $\theta i$ may be used if desired, depending on various design parameters as discussed herein and/or in the aforementioned patent application, and provided that a known diffraction equation (Eq. 1 below) is satisfied:

$$\sin(\theta_i)+\sin(\theta_o)=m\lambda/n\Lambda \qquad \text{Eq. 1}$$

where Eq. 1 is diffraction (or reflection or scatter) relationship between input wavelength $\lambda$, input incident angle $\theta i$, output incident angle $\theta o$, and the spatial period $\Lambda$ of the grating 12. Further, m is the "order" of the reflection being observed, and n is the refractive index of the substrate 10. The value of m=1 or first order reflection is acceptable for illustrative purposes. Eq. 1 applies to light incident on outer surfaces of the substrate 10 which are parallel to the longitudinal axis of the grating (or the $k_B$ vector). Because the angles $\theta i, \theta o$ are defined outside the substrate 10 and because the effective refractive index of the substrate 10 is substantially a common value, the value of n in Eq. 1 cancels out of this equation.

Thus, for a given input wavelength $\lambda$, grating spacing $\Lambda$, and incident angle of the input light $\theta i$, the angle $\theta o$ of the reflected output light may be determined. Solving Eq. 1 for $\theta o$ and plugging in m=1, gives:

$$\theta o = \sin^{-1}(\lambda/\Lambda - \sin(\theta i)) \qquad \text{Eq. 2}$$

For example, for an input wavelength $\lambda$=532 nm, a grating spacing $\Lambda$=0.532 microns (or 532 nm), and an input angle of incidence $\theta i$=30 degrees, the output angle of reflection will be $\theta o$=30 degrees. Alternatively, for an input wavelength $\lambda$=632 nm, a grating spacing $\Lambda$=0.532 microns (or 532 nm), and an input angle $\theta i$ of 30 degrees, the output angle of reflection $\theta o$ will be at 43.47 degrees, or for an input angle $\theta i$=37 degrees, the output angle of reflection will be $\theta o$=37 degrees. Any input angle that satisfies the design requirements discussed herein and/or in the aforementioned patent application may be used.

In addition, to have sufficient optical output power and signal to noise ratio, the output light 27 should fall within an acceptable portion of the Bragg envelope (or normalized reflection efficiency envelope) curve 200, as indicated by points 204,206, also defined as a Bragg envelope angle $\theta B$, as also discussed herein and/or in the aforementioned patent application. The curve 200 may be defined as:

$$I(ki, ko) \approx [KD]^2 \text{sinc}^2\left[\frac{(ki-ko)D}{2}\right] \qquad \text{Eq. 3}$$

where $K=2\pi\delta n/\lambda$, where, $\delta n$ is the local refractive index modulation amplitude of the grating and $\lambda$ is the input wavelength, $\text{sinc}(x)=\sin(x)/x$, and the vectors $k_i=2\pi \cos(\theta_i)/\lambda$ and $k_o=2\pi \cos(\theta_o)/\lambda$ are the projections of the incident light and the output (or reflected) light, respectively, onto the line 203 normal to the axial direction of the grating 12 (or the grating vector $k_B$), D is the thickness or depth of the grating 12 as measured along the line 203 (normal to the axial direction of the grating 12). Other substrate shapes than a cylinder may be used and will exhibit a similar peaked characteristic of the Bragg envelope. We have found that a value for $\delta n$ of about $10^{-4}$ in the grating region of the substrate is acceptable; however, other values may be used if desired.

Rewriting Eq. 3 gives the reflection efficiency profile of the Bragg envelope as:

$$I(ki, io) \approx \left[\frac{2\pi \cdot \delta n \cdot D}{\lambda}\right]^2 \left[\frac{\text{Sin}(x)}{x}\right]^2 \qquad \text{Eq. 4}$$

where: $x=(ki-ko)D/2=(\pi D/\lambda)*(\cos \theta i - \cos \theta o)$

Thus, when the input angle $\theta i$ is equal to the output (or reflected) angle $\theta_o$ (i.e., $\theta i = \theta_o$, the reflection efficiency I (Eqs. 3 & 4) is maximized, which is at the center or peak of the Bragg envelope. When $\theta i = \theta o$, the input light angle is referred to as the Bragg angle as is known. The efficiency decreases for other input and output angles (i.e., $\theta i \neq \theta_o$, as defined by Eqs. 3 & 4. Thus, for maximum reflection efficiency and thus output light power, for a given grating pitch $\Lambda$ and input wavelength, the angle $\theta i$ of the input light 24 should be set so that the angle $\theta o$ of the reflected output light equals the input angle $\theta i$.

Also, as the thickness or diameter D of the grating decreases, the width of the $\sin(x)/x$ function (and thus the width of the Bragg envelope) increases and, the coefficient to or amplitude of the $\text{sinc}^2$ (or $(\sin(x)/x)^2$ function (and thus the efficiency level across the Bragg envelope) also increases, and vice versa. Further, as the wavelength $\lambda$ increases, the half-width of the Bragg envelope as well as the efficiency level across the Bragg envelope both decrease. Thus, there is a trade-off between the brightness of an individual bit and the number of bits available under the Bragg envelope. Ideally, $\delta n$ should be made as large as possible to maximize the brightness, which allows D to be made smaller.

From Eq. 3 and 4, the half-angle of the Bragg envelope $\theta_B$ is defined as:

$$\theta_B = \frac{\eta \lambda}{\pi D \sin(\theta_i)} \qquad \text{Eq. 5}$$

where $\eta$ is a reflection efficiency factor which is the value for x in the $\text{sinc}^2(x)$ function where the value of $\text{sinc}^2(x)$ has decreased to a predetermined value from the maximum amplitude as indicated by points 204,206 on the curve 200.

We have found that the reflection efficiency is acceptable when $\eta \leq 1.39$. This value for $\eta$ corresponds to when the amplitude of the reflected beam (i.e., from the $\text{sinc}^2(x)$ function of Eqs. 3 & 4) has decayed to about 50% of its peak value. In particular, when $x=1.39=\eta$, $\text{sinc}^2(x)=0.5$. However, other values for efficiency thresholds or factor in the Bragg envelope may be used if desired.

The beams 26-36 are imaged onto the CCD camera 60 to produce the pattern of light and dark regions 120-132 representing a digital (or binary) code, where light=1 and dark=0 (or vice versa). The digital code may be generated by selectively creating individual index variations (or individual gratings) with the desired spatial periods $\Lambda 1$-$\Lambda n$. Other illumination, readout techniques, types of gratings, geometries, materials, etc. may be used as discussed in the aforementioned patent application.

Figure 13:
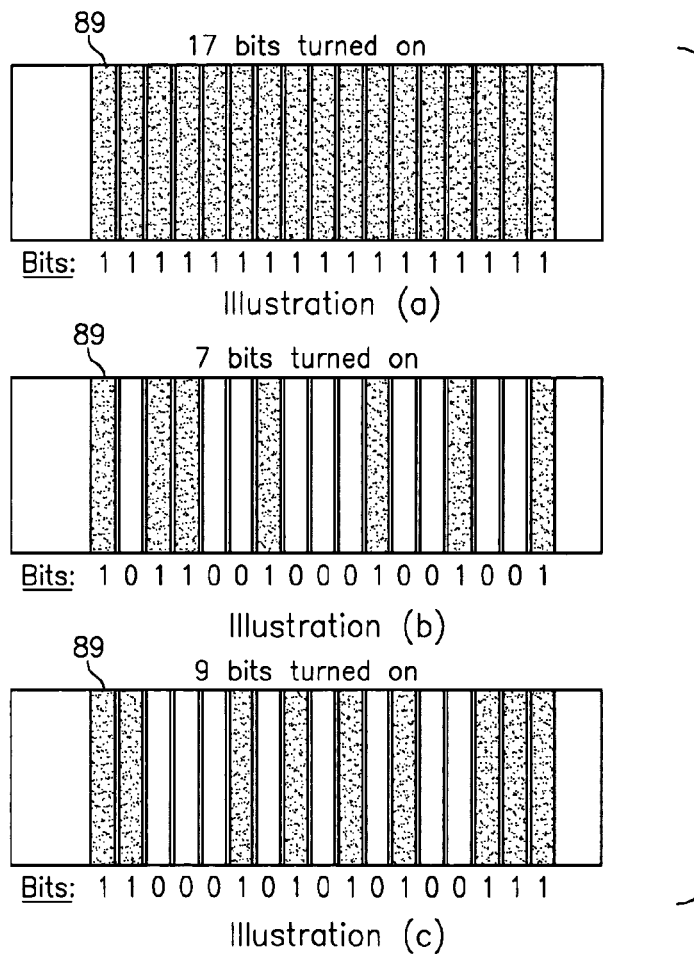
FIG. 13 illustrations (a)-(c) show images of digital codes on a CCD camera, in accordance with the present invention.

Referring to FIG. 13, illustrations (a)-(c), for the grating 12 in a cylindrical substrate 10 having a sample spectral 17 bit code (i.e., 17 different pitches Λ1-Λ17), the corresponding image on the CCD (Charge Coupled Device) camera 60 is shown for a digital pattern 89 of 7 bits turned on (10110010001001001); 9 bits turned on of (11000101010100111); and all 17 bits turned on of (11111111111111111).

For the images in FIG. 13, the length of the substrate 10 was 450 microns, the outer diameter D1 was 65 microns, the inner diameter D was 14 microns, δn for the grating 12 was about $10^{-4}$, n1 in portion 20 was about 1.458 (at a wavelength of about 1550 nm), n2 in portion 18 was about 1.453, the average pitch spacing Λ for the grating 12 was about 0.542 microns, and the spacing between pitches ΔΛ was about 0.36% of the adjacent pitches Λ.

Figure 14:
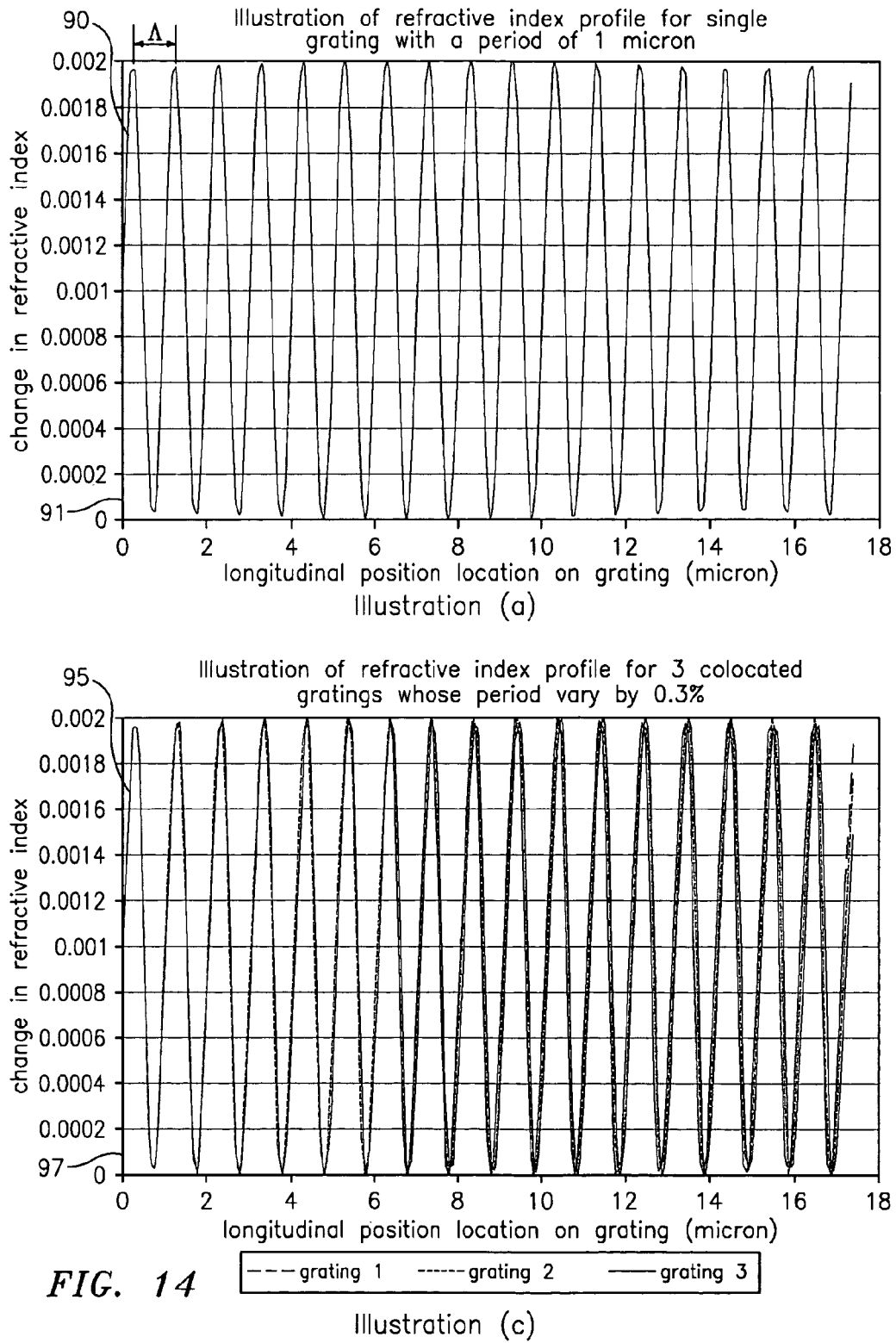
FIG. 14 illustrations (a)-(d) show graphs of different refractive index pitches and a summation graph, in accordance with the present invention.

Referring to FIG. 14, illustration (a), the pitch Λ of an individual grating is the axial spatial period of the sinusoidal variation in the refractive index n1 in the region 20 of the substrate 10 along the axial length of the grating 12 as indicated by a curve 90 on a graph 91. Referring to FIG. 14, illustration (b), a sample composite grating 12 comprises three individual gratings that are co-located on the substrate 10, each individual grating having slightly different pitches, Λ1, Λ2, Λ3, respectively, and the difference (or spacing) ΔΛ between each pitch Λ being about 3.0% of the period of an adjacent pitch Λ as indicated by a series of curves 92 on a graph 94. Referring to FIG. 14, illustration (c), three individual gratings, each having slightly different pitches, Λ1, Λ2, Λ3, respectively, are shown, the difference ΔΛ between each pitch Λ being about 0.3% of the pitch Λ of the adjacent pitch as shown by a series of curves 95 on a graph 97. The individual gratings in FIG. 14, illustrations (b) and (c) are shown to all start at 0 for illustration purposes; however, it should be understood that, the separate gratings need not all start in phase with each other. Referring to FIG. 14, illustration (d), the overlapping of the individual sinusoidal refractive index variation pitches Λ1-Λn in the grating region 20 of the substrate 10, produces a combined resultant refractive index variation in the composite grating 12 shown as a curve 96 on a graph 98 representing the combination of the three pitches shown in FIG. 14, illustration (b). Accordingly, the resultant refractive index variation in the grating region 20 of the substrate 10 may not be sinusoidal and is a combination of the individual pitches Λ (or index variation).

The maximum number of resolvable bits N, which is equal to the number of different grating pitches Λ (and hence the number of codes), that can be accurately read (or resolved) using side-illumination and side-reading of the grating 12 in the substrate 10, is determined by numerous factors, including: the beam width w incident on the substrate (and the corresponding substrate length L and grating length Lg), the thickness or diameter D of the grating 12, the wavelength λ of incident light, the beam divergence angle $\theta_R$, and the width of the Bragg envelope $\theta_B$ (discussed more in the aforementioned patent application), and may be determined by the equation:

$$N \cong \frac{\eta \beta L}{2D\sin(\theta_i)} \qquad \text{Eq. 6}$$

Figure 15:
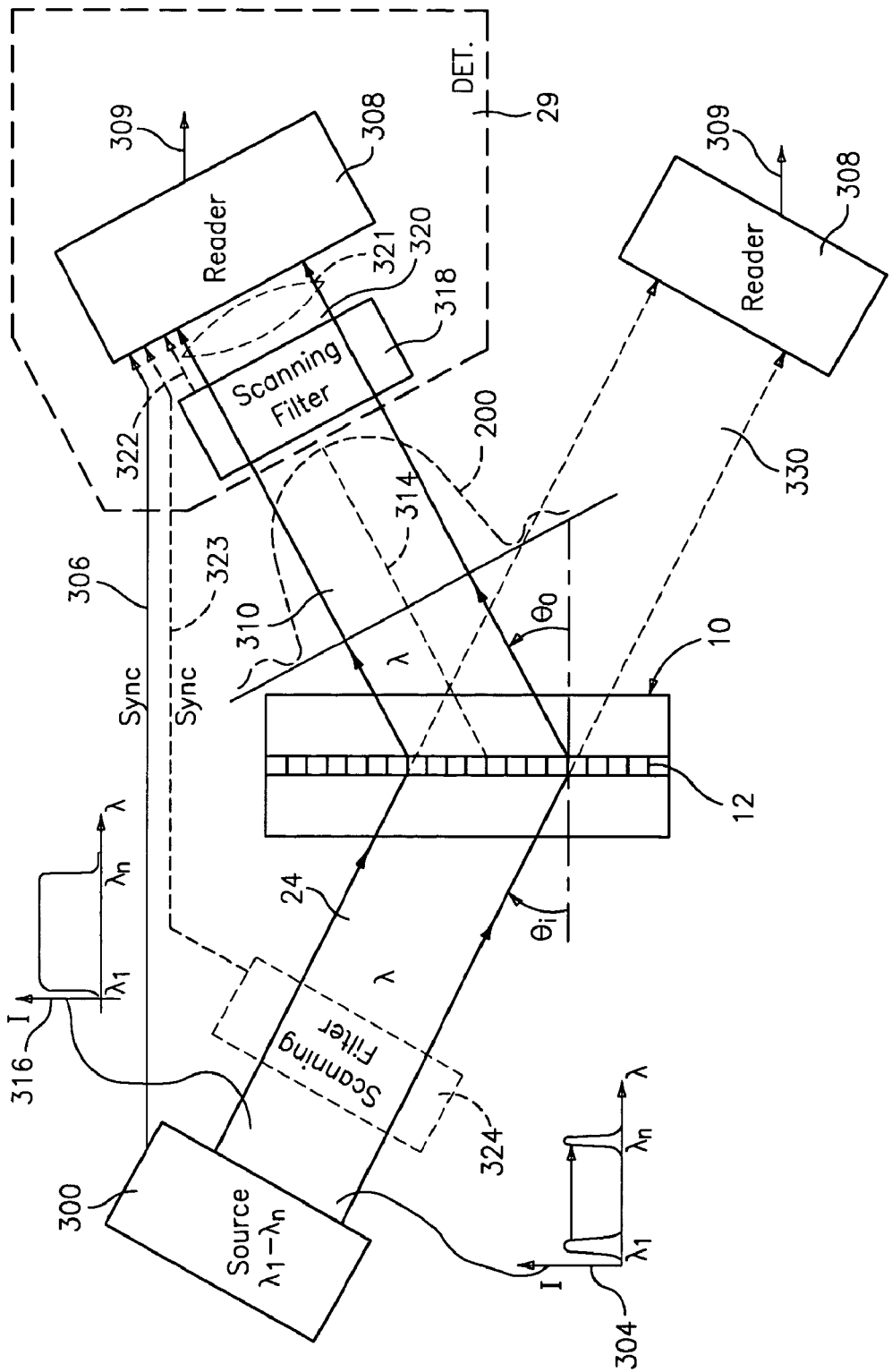
FIG. 15 is an alternative optical schematic for reading a code in an optical identification element, in accordance with the present invention.

Referring to FIG. 15, instead of having the input light 24 at a single wavelength λ (monochromatic) and reading the bits by the angle θo of the output light, the bits (or grating pitches Λ) may be read/detected by providing a plurality of wavelengths and reading the wavelength spectrum of the reflected output light signal. In this case, there would be one bit per wavelength, and thus, the code is contained in the wavelength information of the reflected output signal.

In this case, each bit (or Λ) is defined by whether its corresponding wavelength falls within the Bragg envelope, not by its angular position within the Bragg envelope 200. As a result, it is not limited by the number of angles that can fit in the Bragg envelope 200 for a given composite grating 12, as in the embodiment discussed hereinbefore. Thus, using multiple wavelengths, the only limitation in the number of bits N is the maximum number of grating pitches Λ that can be superimposed and optically distinguished in wavelength space for the output beam.

Figure 16:
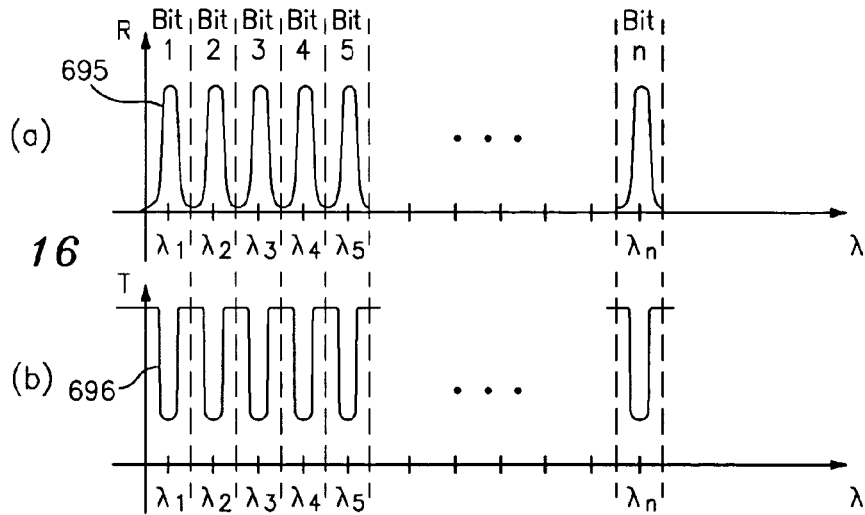
FIG. 16 illustrations (a)-(b) are graphs of reflection and transmission wavelength spectrum for an optical identification element, in accordance with the present invention.

Referring to FIGS. 15 and 16, illustration (a), the reflection wavelength spectrum (λ1-λn) of the reflected output beam 310 will exhibit a series of reflection peaks 695, each appearing at the same output Bragg angle θo. Each wavelength peak 695 (λ1-λn) corresponds to an associated spatial period (Λ1-Λn), which make up the grating 12.

One way to measure the bits in wavelength space is to have the input light angle θi equal to the output light angle θo, which is kept at a constant value, and to provide an input wavelength λ that satisfies the diffraction condition (Eq. 1) for each grating pitch Λ. This will maximize the optical power of the output signal for each pitch Λ detected in the grating 12.

Referring to FIG. 16, illustration (b), the transmission wavelength spectrum of the transmitted output beam 330 (which is transmitted straight through the grating 12) will exhibit a series of notches (or dark spots) 696. Alternatively, instead of detecting the reflected output light 310, the transmitted light 330 may be detected at the detector/reader 308. It should be understood that the optical signal levels for the reflection peaks 695 and transmission notches 696 will depend on the "strength" of the grating 12, i.e., the magnitude of the index variation n in the grating 12.

In FIG. 15, the bits may be detected by continuously scanning the input wavelength. A known optical source 300 provides the input light signal 24 of a coherent scanned wavelength input light shown as a graph 304. The source 300 provides a sync signal on a line 306 to a known reader 308. The sync signal may be a timed pulse or a voltage ramped signal, which is indicative of the wavelength being provided as the input light 24 to the substrate 10 at any given time. The reader 308 may be a photodiode, CCD camera, or other optical detection device that detects when an optical signal is present and provides an output signal on a line 309 indicative of the code in the substrate 10 or of the wavelengths present in the output light, which is directly related to the code, as discussed herein. The grating 12 reflects the input light 24 and provides an output light signal 310 to the reader 308. The wavelength of the input signal is set such that the reflected output light 310 will be substantially in the center 314 of the Bragg envelope 200 for the individual grating pitch (or bit) being read.

Alternatively, the source 300 may provide a continuous broadband wavelength input signal such as that shown as a graph 316. In that case, the reflected output beam 310 signal is provided to a narrow band scanning filter 318 through a lens 321 which scans across the desired range of wavelengths and provides a filtered output optical signal 320 to the reader 308. The filter 318 provides a sync signal on a line 322 to the reader, which is indicative of which wavelengths are being provided on the output signal 320 to the reader and may be similar to the sync signal discussed hereinbefore on the line 306 from the source 300. In this case, the source 300 does not need to provide a sync signal because the input optical signal 24 is continuous. Alternatively, instead of having the scanning filter being located in the path of the output beam 310, the scanning filter may be located in the path of the input beam 24 as indicated by the dashed box 324, which provides the sync signal on a line 323.

Alternatively, instead of the scanning filters 318,324, the reader 308 may be a known optical spectrometer (such as a known spectrum analyzer), capable of measuring the wavelength of the output light.

The desired values for the input wavelengths λ (or wavelength range) for the input signal 24 from the source 300 may be determined from the Bragg condition of Eq. 1, for a given grating spacing Λ and equal angles for the input light θi and the angle light θo. Solving Eq. 1 for λ and plugging in m=1, gives:

$$\lambda = \Lambda[\sin(\theta o) + \sin(\theta i)] \qquad \text{Eq. 7}$$

It is also possible to combine the angular-based code detection with the wavelength-based code detection, both discussed hereinbefore. In this case, each readout wavelength is associated with a predetermined number of bits within the Bragg envelope. Bits (or grating pitches Λ) written for different wavelengths do not show up unless the correct wavelength is used.

Accordingly, the bits (or grating pitches Λ) can be read using one wavelength and many angles, many wavelengths and one angle, or many wavelengths and many angles.

Figure 17:
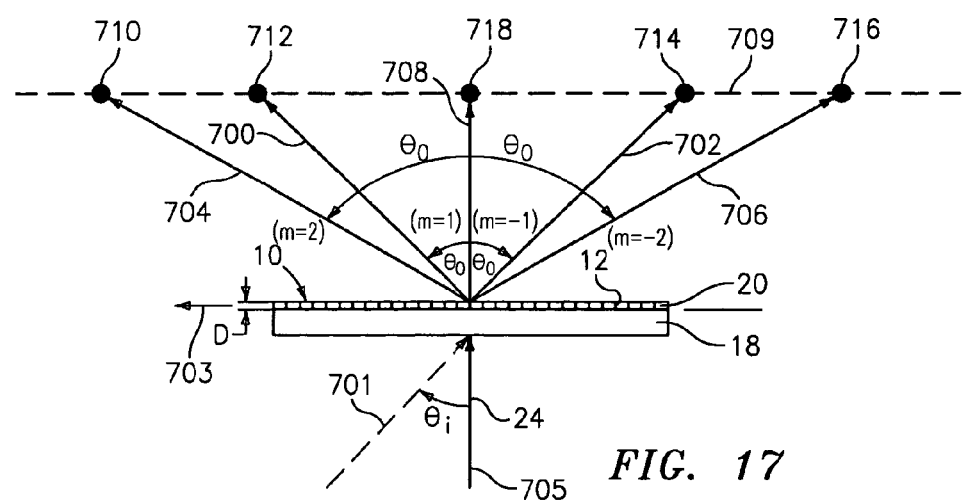
FIGS. 17-18 are side views of a thin grating for an optical identification element, in accordance with the present invention.

Referring to FIG. 17, the grating 12 may have a thickness or depth D which is comparable or smaller than the incident beam wavelength λ. This is known as a "thin" diffraction grating (or the full angle Bragg envelope is 180 degrees). In that case, the half-angle Bragg envelope θB is substantially 90 degrees; however, δn must be made large enough to provide sufficient reflection efficiency, per Eqs. 3 and 4. In particular, for a "thin" grating, $D*\delta n \approx \lambda/2$, which corresponds to a π phase shift between adjacent minimum and maximum refractive index values of the grating 12.

It should be understood that there is still a trade-off discussed hereinbefore with beam divergence angle $\theta_R$ and the incident beam width (or length L of the substrate), but the accessible angular space is theoretically now 90 degrees. Also, for maximum efficiency, the phase shift between adjacent minimum and maximum refractive index values of the grating 12 should approach a π phase shift; however, other phase shifts may be used.

In this case, rather than having the input light 24 coming in at the conventional Bragg input angle θi, as discussed hereinbefore and indicated by a dashed line 701, the grating 12 is illuminated with the input light 24 oriented on a line 705 orthogonal to the longitudinal grating vector 704. The input beam 24 will split into two (or more) beams of equal amplitude, where the exit angle $\theta_o$ can be determined from Eq. 1 with the input angle $\theta_i=0$ (normal to the longitudinal axis of the grating 12).

In particular, from Eq. 1, for a given grating pitch Λ1, the +/−1$^{st}$ order beams (m=+1 and m=−1), corresponds to output beams 700,702, respectively. The +/−2$^{nd}$ order beams (m=+2 and m=−2), corresponds to output beams 704,706, respectively. The 0$^{th}$ order (undiffracted) beam (m=0) corresponds to beam 708 and passes straight through the substrate. The output beams 700-708 project spectral spots or peaks 710-718, respectively, along a common plane, shown from the side by a line 709, which is parallel to the upper surface of the substrate 10.

For example, for a grating pitch Λ=1.0 um, and an input wavelength λ=400 nm, the exit angles $\theta_o$ are ~+/−23.6 degrees (for m=+/−1), and +/−53.1 degrees (from m=+/−2), from Eq. 1. It should be understood that for certain wavelengths, certain orders (e.g., m=+/−2) may be reflected back toward the input side or otherwise not detectable at the output side of the grating 12.

Alternatively, one can use only the +/−1$^{st}$ order (m=+/−1) output beams for the code, in which case there would be only 2 peaks to detect, 712, 714. Alternatively, one can also use any one or more pairs from any order output beam that is capable of being detected. Alternatively, instead of using a pair of output peaks for a given order, an individual peak may be used.

Figure 18:
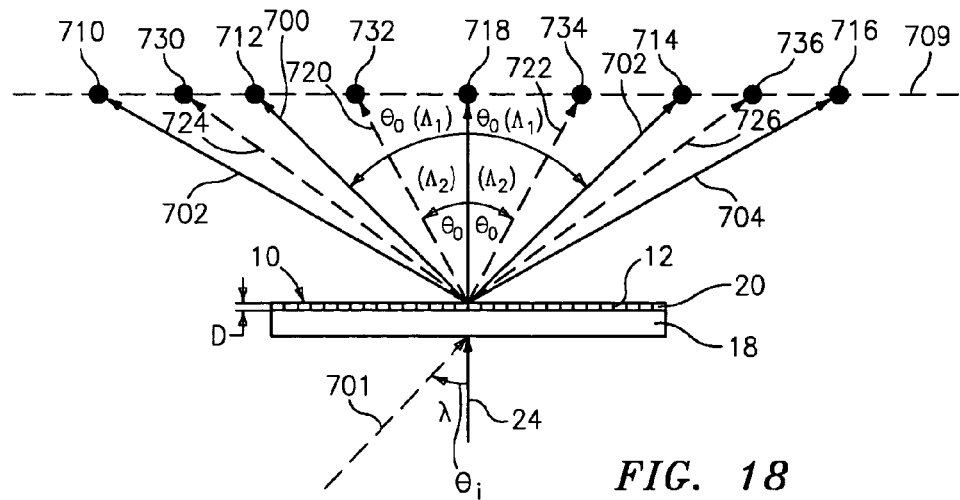

Referring to FIG. 18, if two pitches Λ1,Λ2 exist in the grating 12, two sets of peaks will exist. In particular, for a second grating pitch Λ2, the +/−1$^{st}$ order beams (m=+1 and m=−1), corresponds to output beams 720,722, respectively. For the +/−2$^{nd}$ order beams (m=+2 and m=−2), corresponds to output beams 724,726, respectively. The 0$^{th}$ order (un-defracted) beam (m=0), corresponds to beam 718 and passes straight through the substrate. The output beams 720-726 corresponding to the second pitch Λ2 project spectral spots or peaks 730-736, respectively, which are at a different location than the point 710-716, but along the same common plane, shown from the side by the line 709.

Thus, for a given pitch Λ (or bit) in a grating, a set of spectral peaks will appear at a specific location in space. Thus, each different pitch corresponds to a different elevation or output angle which corresponds to a predetermined set of spectral peaks. Accordingly, the presence or absence of a particular peak or set of spectral peaks defines the code.

In general, if the angle of the grating 12 is not properly aligned with respect to the mechanical longitudinal axis of the substrate 10, the readout angles may no longer be symmetric, leading to possible difficulties in readout. With a thin grating, the angular sensitivity to the alignment of the longitudinal axis of the substrate 10 to the input angle θi of incident radiation is reduced or eliminated. In particular, the input light can be oriented along substantially any angle θi with respect to the grating 12 without causing output signal degradation, due the large Bragg angle envelope. Also, if the incident beam 24 is normal to the substrate 10, the grating 12 can be oriented at any rotational (or azimuthal) angle without causing output signal degradation. However, in each of these cases, changing the incident angle θi will affect the output angle θo of the reflected light in a predetermined predictable way, thereby allowing for accurate output code signal detection or compensation.

Referring to FIG. 19, for a thin grating, in addition to multiplexing in the elevation or output angle based on grating pitch Λ, the bits can also be multiplexed in an azimuthal (or rotational) angle θa of the substrate. In particular, a plurality of gratings 750,752,754,756 each having the same pitch Λ are disposed in a surface 701 of the substrate 10 and located in the plane of the substrate surface 701. The input light 24 is incident on all the gratings 750,752,754,756 simultaneously. Each of the gratings provides output beams oriented based on the grating orientation. For example, the grating 750 provides the output beams 764,762, the grating 752 provides the output beams 766,768, the grating 754 provides the output beams 770,772, and the grating 756 provides the output beams 774, 776. Each of the output beams provides spectral peaks or spots (similar to that discussed hereinbefore), which are located in a plane 760 that is parallel to the substrate surface plane 701. In this case, a single grating pitch Λ can produce many bits depending on the number of gratings that can be placed at different azimuthal (rotational) angles on the surface of the substrate 10 and the number of output beam spectral peaks that can be spatially and optically resolved/detected. Each bit may be viewed as the presence or absence of a pair of peaks located at a predetermined location in space in the plane 760. Note that this example uses only the m=+/−1$^{st}$ order for each reflected output beam. Alternatively, the detection may also use the m=+/−2$^{nd}$ order. In that case, there would be two additional output beams and peaks (not shown) for each grating (as discussed hereinbefore) that may lie in the same plane as the plane 760 and may be on a concentric circle outside the circle 760.

In addition, the azimuthal multiplexing can be combined with the elevation or output angle multiplexing discussed hereinbefore to provide two levels of multiplexing. Accordingly, for a thin grating, the number of bits can be multiplexed based on the number of grating pitches Λ and/or geometrically by the orientation of the grating pitches.

Furthermore, if the input light angle θi is normal to the substrate 10, the edges of the substrate 10 no longer scatter light from the incident angle into the "code angular space", as discussed herein and/or in the aforementioned patent application.

Also, in the thin grating geometry, a continuous broadband wavelength source may be used as the optical source if desired.

Referring to FIG. 20, instead of or in addition to the pitches Λ in the grating 12 being oriented normal to the longitudinal axis, the pitches may be created at a angle θg. In that case, when the input light 24 is incident normal to the surface 792, will produce a reflected output beam 790 having an angle θo determined by Eq. 1 as adjusted for the blaze angle θg. This can provide another level of multiplexing bits in the code.

Figure 21:
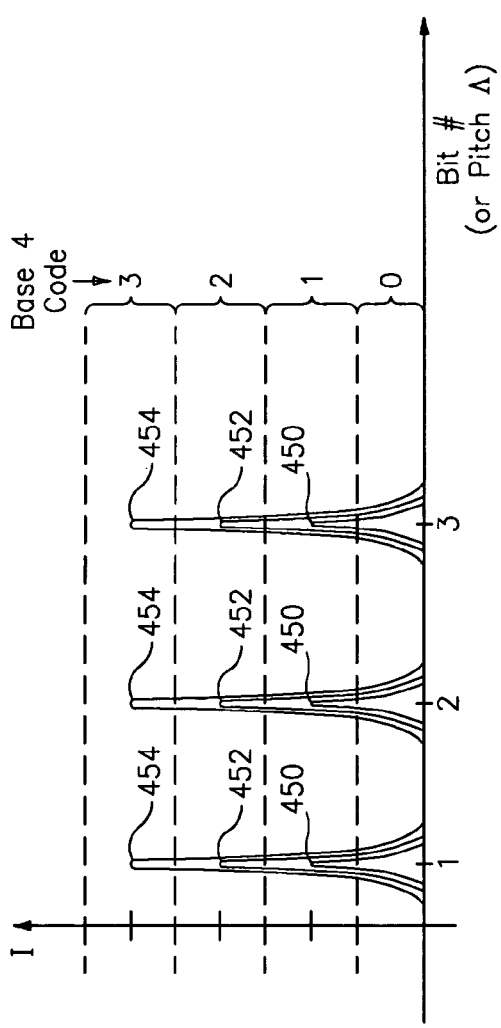
FIG. 21 is a graph of a plurality of states for each bit in a code for an optical identification element, in accordance with the present invention.

Referring to FIG. 21, instead of using an optical binary (0-1) code, an additional level of multiplexing may be provided by having the optical code use other numerical bases, if intensity levels of each bit are used to indicate code information. This could be achieved by having a corresponding magnitude (or strength) of the refractive index change (δn) for each grating pitch Λ. Four intensity ranges are shown for each bit number or pitch Λ, providing for a Base-4 code (where each bit corresponds to 0, 1, 2, or 3). The lowest intensity level, corresponding to a 0, would exist when this pitch Λ is not present in the grating 12. The next intensity level 450 would occur when a first low level δn1 exists in the grating that provides an output signal within the intensity range corresponding to a 1. The next intensity level 452 would occur when a second higher level δn2 exists in the grating 12 that provides an output signal within the intensity range corresponding to a 2. The next intensity level 454, would occur when a third higher level δn3 exists in the grating 12 that provides an output signal within the intensity range corresponding to a 3.

Figure 22:
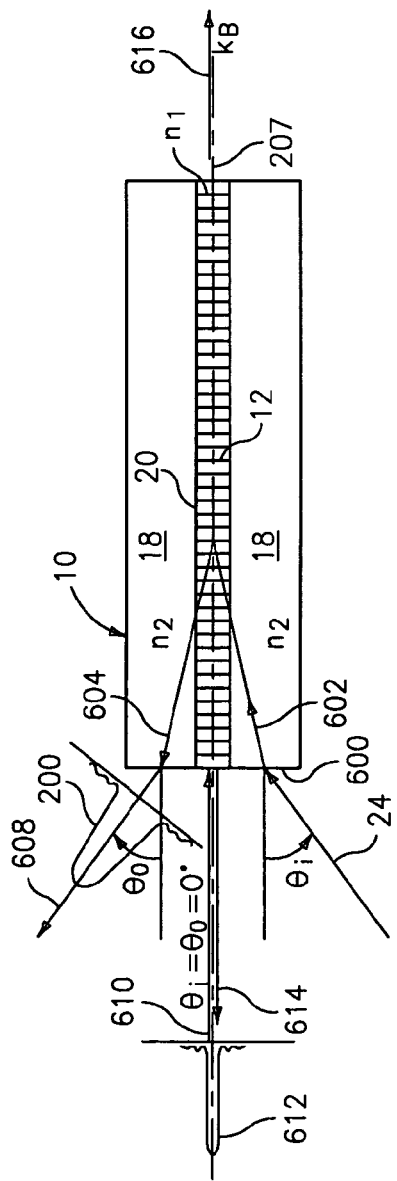
FIG. 22 is a side view of an optical identification element where light is incident on an end face, in accordance with the present invention.

Referring to FIG. 22, the input light 24 may be incident on the substrate 10 on an end face 600 of the substrate 10. In that case, the input light 24 will be incident on the grating 12 having a more significant component of the light (as compared to side illumination discussed hereinbefore) along the longitudinal grating axis 207 of the grating (along the grating vector $k_B$), as shown by a line 602. The light 602 reflects off the grating 12 as indicated by a line 604 and exits the substrate as output light 608. Accordingly, it should be understood by one skilled in the art that the diffraction equations discussed hereinbefore regarding output diffraction angle θo also apply in this case except that the reference axis would now be the grating axis 207. Thus, in this case, the input and output light angles θi,θo, would be measured from the grating axis 207 and length Lg of the grating 12 would become the thickness or depth D of the grating 12. As a result, a grating 12 that is 400 microns long, would result in the Bragg envelope 200 being narrow. It should be understood that because the values of n1 and n2 are close to the same value, the slight angle changes of the light between the regions 18,20 are not shown herein.

In the case where incident light 610 is incident along the same direction as the grating vector (Kb) 207, i.e., θi=0 degrees, the incident light sees the whole length Lg of the grating 12 and the grating provides a reflected output light angle θo=0 degrees, and the Bragg envelope 612 becomes extremely narrow, as the narrowing effect discussed above reaches a limit. In that case, the relationship between a given pitch Λ in the grating 12 and the wavelength of reflection λ is governed by a known "Bragg grating" relation:

$$\lambda = 2n_{eff}\Lambda \qquad \text{Eq. 8}$$

where $n_{eff}$ is the effective index of refraction of the substrate, λ is the input (and output wavelength) and Λ is the pitch. This relation, as is known, may be derived from Eq. 1 where θi=θo=90 degrees.

In that case, the code information is readable only in the spectral wavelength of the reflected beam, similar to that discussed hereinbefore for wavelength based code reading. Accordingly, the input signal in this case may be a scanned wavelength source or a broadband wavelength source. In addition, as discussed hereinbefore for wavelength based code reading, the code information may be obtained in reflection from the reflected beam 614 or in transmission by the transmitted beam 616 that passes through the grating 12.

It should be understood that for shapes of the substrate 10 or element 8 other than a cylinder, the effect of various different shapes on the propagation of input light through the element 8, substrate 10, and/or grating 12, and the associated reflection angles, can be determined using known optical physics including Snell's Law, shown below:

$$n_{in}\sin\theta\text{in} = n_{out}\sin\theta\text{out} \qquad \text{Eq. 9}$$

where $n_{in}$ is the refractive index of the first (input) medium, and $n_{out}$ is the refractive index of the second (output) medium, and θin and θout are measured from a line 620 normal to an incident surface 622.

Referring to FIG. 23, if the value of n1 in the grating region 20 is greater than the value of n2 in the non-grating region 18, the grating region 20 of the substrate 10 will act as a known optical waveguide for certain wavelengths. In that case, the grating region 20 acts as a "core" along which light 630 is guided and the outer region 18 acts as a "cladding" which helps confine or guide the light. Also, such a waveguide will have a known "numerical aperture" (θna) that will allow light that is within the aperture θna to be directed or guided along the grating axis 207 and reflected axially off the grating 12 and returned and guided along the waveguide. In that case, the grating 12 will reflect light 631 having the appropriate wavelengths equal to the pitches Λ present in the grating 12 back along the region 20 (or core) of the waveguide, and pass the remaining wavelengths of light as the light 632. Thus, having the grating region 20 act as an optical waveguide for wavelengths reflected by the grating 12 allows incident light that is not aligned exactly with the grating axis 207 to be guided along and aligned with the grating 12 axis 207 for optimal grating reflection.

If an optical waveguide is used any standard waveguide may be used, e.g., a standard telecommunication single mode optical fiber (125 micron diameter or 80 micron diameter fiber with about a 8-10 micron diameter), or a larger diameter waveguide (greater than 0.5 mm diameter), such as is describe in U.S. patent application Ser. No. 09/455,868, filed Dec. 6, 1999, entitled "Large Diameter Waveguide, Grating". Further, any type of optical waveguide may be used for the optical substrate 10, such as, a multi-mode, birefringent, polarization maintaining, polarizing, multi-core, multi-cladding, or microsturctured optical waveguide, or a flat or planar waveguide (where the waveguide is rectangular shaped), or other waveguides.

Figure 45:
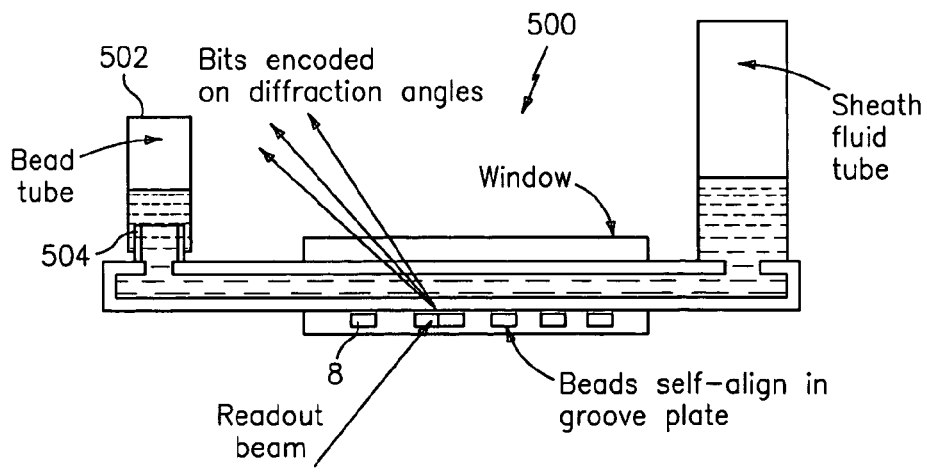
FIG. 45 is a diagram of a code readout step for the Bead Mapper, in accordance with the invention.

Referring to FIG. 24, if the grating 12 extends across the entire dimension D of the substrate, the substrate 10 does not behave as a waveguide for the incident or reflected light and the incident light 24 will be diffracted (or reflected) as indicated by lines 642, and the codes detected as discussed hereinbefore for the end-incidence condition discussed hereinbefore with FIG. 45, and the remaining light 640 passes straight through.

Referring to FIG. 25, illustrations (a)-(c), in illustration (a), for the end illumination condition, if a blazed or angled grating is used, as discussed hereinbefore, the input light 24 is coupled out of the substrate 10 at a known angle as shown by a line 650. Referring to FIG. 25, illustration (b), alternatively, the input light 24 may be incident from the side and, if the grating 12 has the appropriate blaze angle, the reflected light will exit from the end face 652 as indicated by a line 654. Referring to FIG. 25, illustration (c), the grating 12 may have a plurality of different pitch angles 660,662, which reflect the input light 24 to different output angles as indicated by lines 664, 666. This provides another level of multiplexing (spatially) additional codes, if desired.

The grating 12 may be impressed in the substrate 10 by any technique for writing, impressed, embedded, imprinted, or otherwise forming a diffraction grating in the volume of or on a surface of a substrate 10. Examples of some known techniques are described in U.S. Pat. Nos. 4,725,110 and 4,807,950, entitled "Method for Impressing Gratings Within Fiber Optics", to Glenn et al; and U.S. Pat. No. 5,388,173, entitled "Method and Apparatus for Forming Aperiodic Gratings in Optical Fibers", to Glenn, respectively, and U.S. Pat. No. 5,367,588, entitled "Method of Fabricating Bragg Gratings Using a Silica Glass Phase Grating Mask and Mask Used by Same", to Hill, and U.S. Pat. No. 3,916,182, entitled "Periodic Dielectric Waveguide Filter", Dabby et al, and U.S. Pat. No. 3,891,302, entitled "Method of Filtering Modes in Optical Waveguides", to Dabby et al, which are all incorporated herein by reference to the extent necessary to understand the present invention.

Alternatively, instead of the grating 12 being impressed within the substrate material, the grating 12 may be partially or totally created by etching or otherwise altering the outer surface geometry of the substrate to create a corrugated or varying surface geometry of the substrate, such as is described in U.S. Pat. No. 3,891,302, entitled "Method of Filtering Modes in Optical Waveguides", to Dabby et al, which is incorporated herein by reference to the extent necessary to understand the present invention, provided the resultant optical refractive profile for the desired code is created.

Further, alternatively, the grating 12 may be made by depositing dielectric layers onto the substrate, similar to the way a known thin film filter is created, so as to create the desired resultant optical refractive profile for the desired code.

The substrate 10 (and/or the element 8) may have end-view cross-sectional shapes other than circular, such as square, rectangular, elliptical, clam-shell, D-shaped, or other shapes, and may have side-view sectional shapes other than rectangular, such as circular, square, elliptical, clam-shell, D-shaped, or other shapes. Also, 3D geometries other than a cylinder may be used, such as a sphere, a cube, a pyramid or any other 3D shape. Alternatively, the substrate 10 may have a geometry that is a combination of one or more of the foregoing shapes.

The shape of the element 8 and the size of the incident beam may be made to minimize any end scatter off the end face(s) of the element 8, as is discussed herein and/or in the aforementioned patent application. Accordingly, to minimize such scatter, the incident beam 24 may be oval shaped where the narrow portion of the oval is smaller than the diameter D1, and the long portion of the oval is smaller than the length L of the element 8. Alternatively, the shape of the end faces may be rounded or other shapes or may be coated with an antireflective coating.

It should be understood that the size of any given dimension for the region 20 of the grating 12 may be less than any corresponding dimension of the substrate 10. For example, if the grating 12 has dimensions of length Lg, depth Dg, and width Wg, and the substrate 12 has different dimensions of length L, depth D, and width W, the dimensions of the grating 12 may be less than that of the substrate 12. Thus, the grating 12, may be embedded within or part of a much larger substrate 12. Also, the element 8 may be embedded or formed in or on a larger object for identification of the object.

The dimensions, geometries, materials, and material properties of the substrate 10 are selected such that the desired optical and material properties are met for a given application. The resolution and range for the optical codes are scalable by controlling these parameters as discussed herein and/or in the aforementioned patent application.

Referring to FIG. 26, the substrate 10 may have an outer coating 799, such as a polymer or other material that may be dissimilar to the material of the substrate 10, provided that the coating 799 on at least a portion of the substrate, allows sufficient light to pass through the substrate for adequate optical detection of the code. The coating 799 may be on any one or more sides of the substrate 10. Also, the coating 799 may be a material that causes the element 8 to float or sink in certain fluids (liquid and/or gas) solutions.

Also, the substrate 10 may be made of a material that is less dense than certain fluid (liquids and/or gas) solutions, thereby allowing the elements 8 to float or be buoyant or partially buoyant. Also, the substrate may be made of a porous material, such as controlled pore glass (CPG) or other porous material, which may also reduce the density of the element 8 and may make the element 8 buoyant or partially-buoyant in certain fluids.

Referring to FIG. 27, the grating 12 is axially spatially invariant. As a result, the substrate 10 with the grating 12 (shown as a long substrate 21) may be axially subdivided or cut into many separate smaller substrates 30-36 and each substrate 30-36 will contain the same code as the longer substrate 21 had before it was cut. The limit on the size of the smaller substrates 30-36 is based on design and performance factors discussed herein and/or in the aforementioned patent application.

Referring to FIG. 28, one purpose of the outer region 18 (or region without the grating 12) of the substrate 10 is to provide mechanical or structural support for the inner grating region 20. Accordingly, the entire substrate 10 may comprise the grating 12, if desired. Alternatively, the support portion may be completely or partially beneath, above, or along one or more sides of the grating region 20, such as in a planar geometry, or a D-shaped geometry, or other geometries, as described herein and/or in the aforementioned patent application. The non-grating portion 18 of the substrate 10 may be used for other purposes as well, such as optical lensing effects or other effects (discussed herein or in the aforementioned patent application). Also, the end faces of the substrate 10 need not be perpendicular to the sides or parallel to each other. However, for applications where the elements 8 are stacked end-to-end, the packing density may be optimized if the end faces are perpendicular to the sides.

Referring to FIG. 29, illustrations (a)-(c), two or more substrates 10,250, each having at least one grating therein, may be attached together to form the element 8, e.g., by an adhesive, fusing or other attachment techniques. In that case, the gratings 12,252 may have the same or different codes.

Referring to FIG. 30, illustrations (a) and (b), the substrate 10 may have multiple regions 80,90 and one or more of these regions may have gratings in them. For example, there may be gratings 12,252 side-by-side (illustration (a)), or there may be gratings 82-88, spaced end-to-end (illustration (b)) in the substrate 10.

Referring to FIG. 31, the length L of the element 8 may be shorter than its diameter D, thus, having a geometry such as a plug, puck, wafer, disc or plate.

Referring to FIG. 32, to facilitate proper alignment of the grating axis with the angle θi of the input beam 24, the substrate 10 may have a plurality of the gratings 12 having the same codes written therein at numerous different angular or rotational (or azimuthal) positions of the substrate 10. In particular, two gratings 550, 552, having axial grating axes 551, 553, respectively may have a common central (or pivot or rotational) point where the two axes 551,553 intersect. The angle θi of the incident light 24 is aligned properly with the grating 550 and is not aligned with the grating 552, such that output light 555 is reflected off the grating 550 and light 557 passes through the grating 550 as discussed herein. If the element 8 is rotated as shown by the arrows 559, the angle θi of incident light 24 will become aligned properly with the grating 552 and not aligned with the grating 550 such that output light 555 is reflected off the grating 552 and light 557 passes through the grating 552. When multiple gratings are located in this rotational orientation, the bead may be rotated as indicated by a line 559 and there may be many angular positions that will provide correct (or optimal) incident input angles θi to the grating. While this example shows a circular cross-section, this technique may be used with any shape cross-section.

Referring to FIG. 33, illustrations (a), (b), (c), (d), and (e) the substrate 10 may have one or more holes located within the substrate 10. In illustration (a), holes 560 may be located at various points along all or a portion of the length of the substrate 10. The holes need not pass all the way through the substrate 10. Any number, size and spacing for the holes 560 may be used if desired. In illustration (b), holes 572 may be located very close together to form a honeycomb-like area of all or a portion of the cross-section. In illustration (c), one (or more) inner hole 566 may be located in the center of the substrate 10 or anywhere inside of where the grating region(s) 20 are located. The inner hole 566 may be coated with a reflective coating 573 to reflect light to facilitate reading of one or more of the gratings 12 and/or to reflect light diffracted off one or more of the gratings 12. The incident light 24 may reflect off the grating 12 in the region 20 and then reflect off the surface 573 to provide output light 577. Alternatively, the incident light 24 may reflect off the surface 573, then reflect off the grating 12 and provide the output light 575. In that case the grating region 20 may run axially or circumferentially 571 around the substrate 10. In illustration (d), the holes 579 may be located circumferentially around the grating region 20 or transversely across the substrate 10. In illustration (e), the grating 12 may be located circumferentially around the outside of the substrate 10, and there may be holes 574 inside the substrate 10. In operation, the incident light 24 may reflect off the surface, then reflect off the grating 12 and provide the output light 576.

Referring to FIG. 34, illustrations (a), (b), and (c), the substrate 10 may have one or more protruding portions or teeth 570, 578,580 extending radially and/or circumferentially from the substrate 10. Alternatively, the teeth 570, 578, 580 may have any other desired shape.

Referring to FIG. 35, illustrations (a), (b), (c) a D-shaped substrate, a flat-sided substrate and an eye-shaped (or clamshell or teardrop shaped) substrate 10, respectively, are shown. Also, the grating region 20 may have end cross-sectional shapes other than circular and may have side cross-sectional shapes other than rectangular, such as any of the geometries described herein for the substrate 10. For example, the grating region 20 may have a oval cross-sectional shape as shown by dashed lines 581, which may be oriented in a desired direction, consistent with the teachings herein. Any other geometries for the substrate 10 or the grating region 20 may be used if desired, as described herein.

Referring to FIG. 36, at least a portion of a side of the substrate 10 may be coated with a reflective coating 514 to allow incident light 510 to be reflected back to the same side from which the incident light came, as indicated by reflected light 512.

Referring to FIG. 37, illustrations (a) and (b), alternatively, the substrate 10 can be electrically and/or magnetically polarized, by a dopant or coating, which may be used to ease handling and/or alignment or orientation of the substrate 10 and/or the grating 12, or used for other purposes. Alternatively, the bead may be coated with conductive material, e.g., metal coating on the inside of a holey substrate, or metallic dopant inside the substrate. In these cases, such materials can cause the substrate 10 to align in an electric or magnetic field. Alternatively, the substrate can be doped with an element or compound that fluoresces or glows under appropriate illumination, e.g., a rare earth dopant, such as Erbium, or other rare earth dopant or fluorescent or luminescent molecule. In that case, such fluorescence or luminescence may aid in locating and/or aligning substrates.

Referring to FIG. 3(a), instead of the Bead Mapper providing the code and position information directly to the Reader/scanner 824, it may provide this data to an Assay Analysis device 901, which may also received the bead fluorescence or analyte reaction information and position from the reader/scanner 824. The assay analyzer can then provide the assay results as discussed hereinbefore for the reader/scanner.

Figure 42:
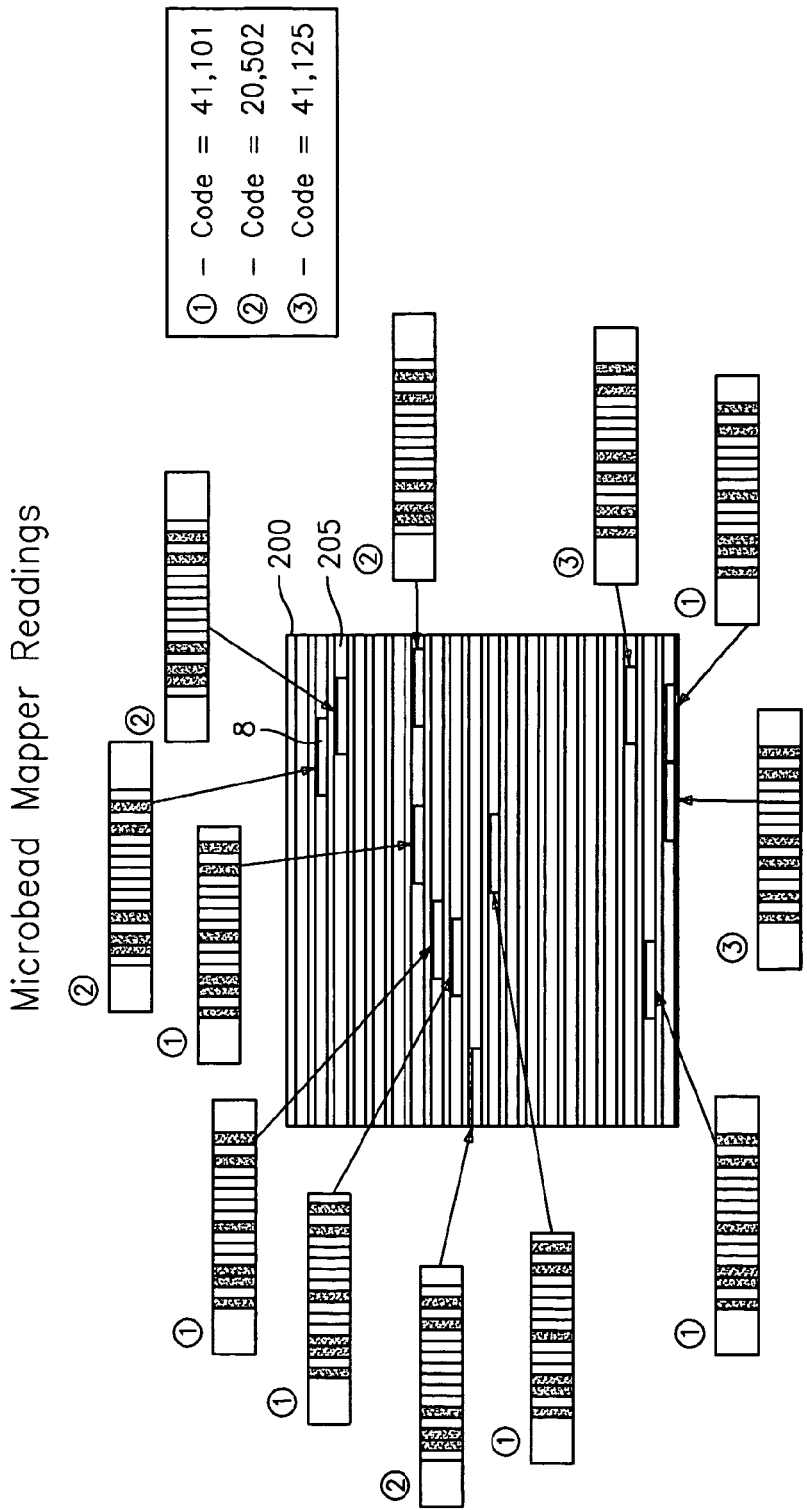
FIG. 42 is a diagram of a microbead mapper reading, in accordance with the present invention.

The slide or chip may be a slide within a housing, discussed herein, or merely a slide having grooves, such as shown in FIG. 42, with little or no additional mechanical hardware attached thereto or used thereby, also referred to as an open format.

Referring to FIG. 42, for an open plate format, meaning there is no top to cover the microbeads 8 and the grooves 205. In this mode, the microbeads 8 are dispensed onto the plate 200 using, for example, a pipette tip or syringe tip, although the scope of the invention is not intended to be limited to the manner of depositing the microbeads on the plate. The microbeads 8 may be then agitated by a sonic transducer (not shown), or manipulated with a mechanical wiper (not shown) or some form of spray nozzle (not shown) to encourage all the microbeads 8 to line up in the grooves 205. It has been observed that substantially all the microbeads naturally line up in the grooves 205 without the need for encouragement. However, there are always some microbeads, that do not fall naturally into the grooves, and these must either be removed from the plate 200 or forced to fall into a groove 205. The open format approach has the advantages that grooves plate consists just of the plate and no other complicated features such as walls and a top, and possibly other chambers or channels to allow fluid flow and bubble removal. It also has the advantage that it can easily be made with a standard microscope slide, which is designed to fit all conventional micro array readers. However, the open format approach may require the microbeads to be dried out prior to reading, to avoid the possibility of non-uniform or unpredictable optical aberrations caused by the uneven evaporation of the buffer solution.

Referring to FIGS. 38,39,40,41,52-53,54-57, regarding the grooved slide, plate or chip that the beads may be placed in.

Figure 38:
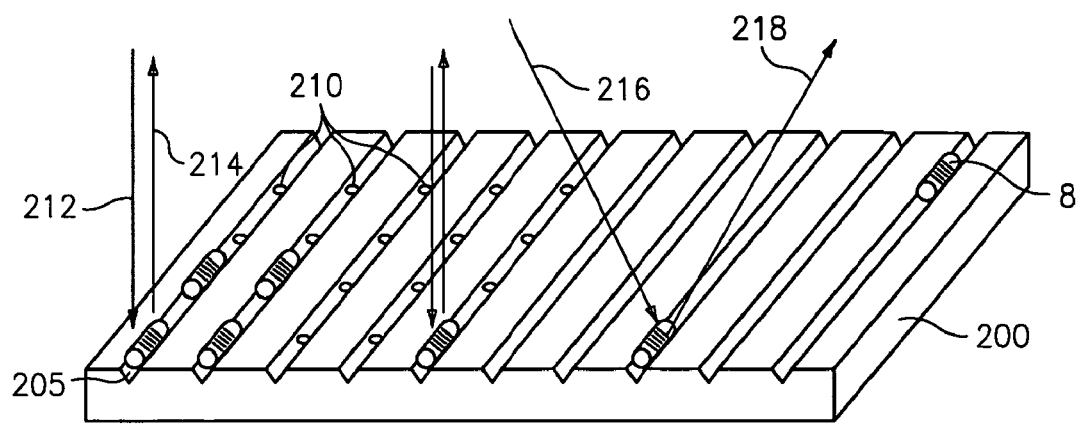
FIG. 38 is a perspective view of a grooved plate for use with an optical identification element, in accordance with the present invention.

Referring to FIG. 38, one embodiment of a positioning device 200 for aligning the microbeads 8 so the longitudinal axis of the microbeads is in a fixed orientation relative to the code reading or other detection device. The positioning device 200 is shown in the form of a tray or plate 200 having grooves 205 for align the microbeads 8 and is used in the process as discussed herein. The geometry grooves may be v-shaped, square or rectangular shaped or any other shape based on the design requirements.

As shown, the microbead elements 8 are placed in the tray 200 with grooves 205 to allow the elements 8 to be aligned in a predetermined direction for illumination and reading/detection as discussed herein. Alternatively, the grooves 205 may have holes 210 that provide suction to keep the elements 8 in position. In operation, in response to incident light 212 provided perpendicular to the plane of the tray 200, the element 8 reflects light 214; while in response to incident light 216 provided oblique to the plane of the tray 200, the element 8 reflects light 218.

Regarding the formation of the grooves, the grooves in the groove plate may be made in many different ways, including being formed by SU8 photoresistant material, mechanically machining; deep reactive ion etching; or injection molding. One advantage of the injection molding approach is that the plate can be manufactured in volume at relatively low cost, and disposed of after the information about the beads is gathered in the assay process. The groove plate may be made of glass, including fused silica, low fluorescence glass, borosilicate glass. Silicon is used because it is reflective so a reflective coating is typically not needed. Alternative, a mirror coating can be applied to the plate material to achieve the desired reflectivity.

Figure 52:
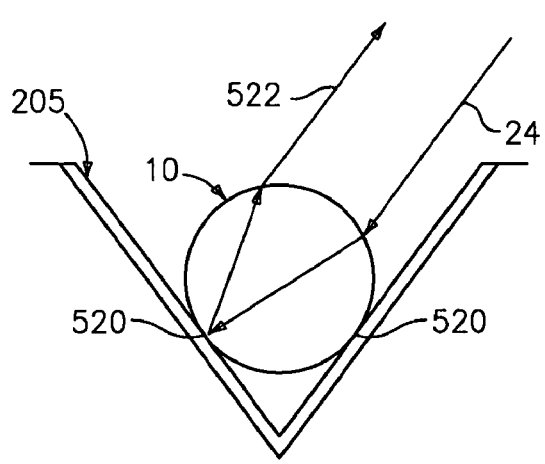
FIGS. 52 and 53 are diagrams of bead reads from retro-reflector trays, in accordance with the present invention.
Figure 53:
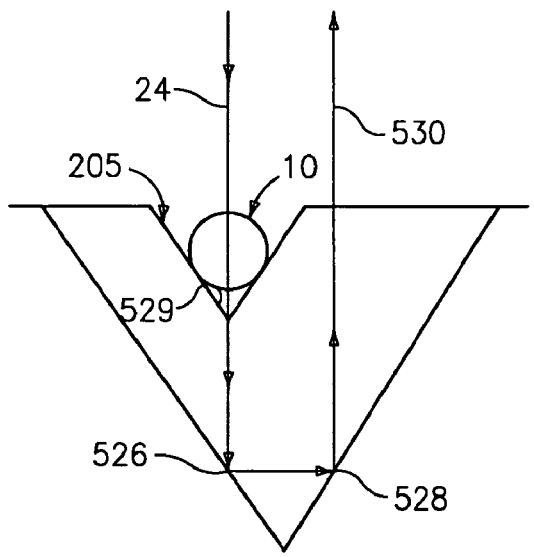
Figure 54:
FIGS. 54 and 55 are diagrams of bead reads from flat retro-reflector trays, in accordance with the present invention.
Figure 55:
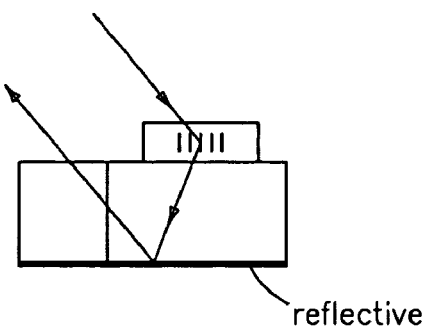
Figure 56:
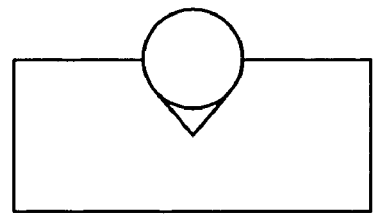
FIGS. 56 and 57 are diagrams of beads read thru V-grooves, in accordance with the present invention.
Figure 57:
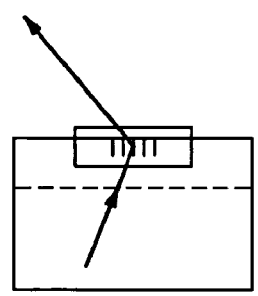

Referring to FIGS. 38 and 52, alternatively, the surfaces inside the grooves 205 may be made of or coated with a reflective material that reflects the incident light. A light beam is incident onto the substrate and diffracted by the grating 12. In particular, the diffracted beam may be reflected by a surface 520 of the groove 205 and read from the same direction as the incident beam 24. Alternatively, referring to FIGS. 38 and 53, the incident light beam 24 may be diffracted by the grating 12 and pass through the upper surface 529 of the groove and reflected off two surfaces 526, 528 which are made or coated with a reflective coating to redirect the output beam upward as a output light beam 530 which may be detected as discussed hereinbefore. Also see FIGS. 54-57 for possible retroreflection and pass-through illumination options.

Figure 39:
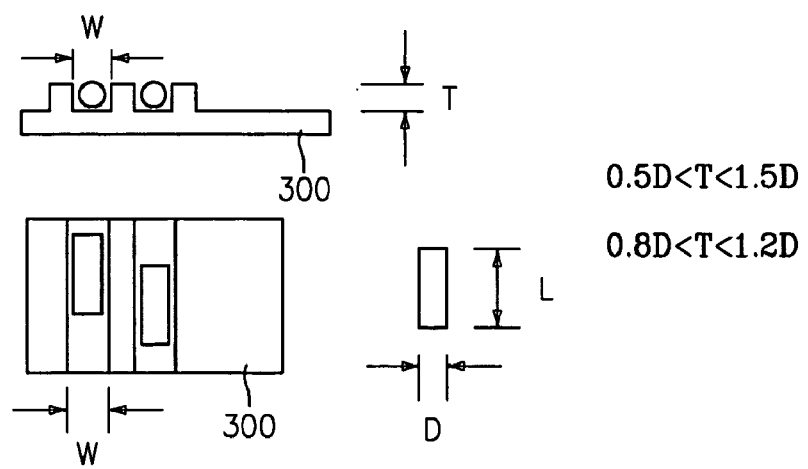
FIG. 39 is a diagram of the flat grooves and an example of the dimensionality thereof in accordance with the present invention.

Referring to FIG. 39, the scope of the invention is not intended to be limited to any particular groove shape. For example, FIG. 39 shows a diagram a plate 300 having flat grooves 302 instead of V-shaped grooves shown in FIG. 38. Some characteristics of the grooves according to the present invention are as follows:

The groove width (w) should be at least as wide as the diameter of the bead (D) but not larger than D+15 μm.

The thickness of the depth of the groove (T) should be at least 0.5 times the diameter of the bead so that it sufficiently traps a bead once it falls into the groove even when it is subjected to mechanical agitation. The depth should not exceed 1.5 times the diameter of the bead so as to prevent more than one bead from falling into the same groove location.

Groove plates have been made using a thick photoresist called SU8 and is available from Microchem. The resist is both chemically inert and mechanically robust once fully cured. The groove walls are formed by the resist material, which is deposited onto a glass or substrate. Advantages of this process include the ability to tailor the depth of groove by controlling the thickness of the resist material, and virtually every other geometric attribute through the design of the photo mask. Because it is photolithographic process, essentially any shape profile can be made. For example grooves can be made in simple rows, concentric circles, or spirals. Other features such as discrete wells, spots and cross hatches can be made as fiducial marks for tracking and positional registration purposes.

The scope of the invention is also intended to include the grooves having a flat bottom as shown in FIG. 39 with outwardly tapered walls.

Figure 40:
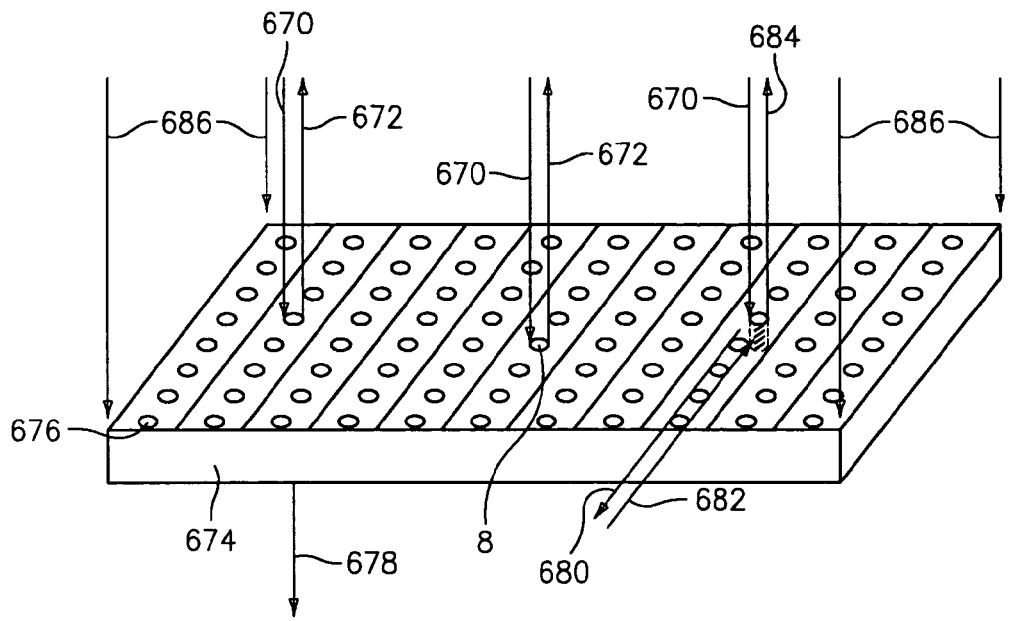
FIG. 40 is a perspective view of a plate with holes for use with an optical identification element, in accordance with the present invention.

Referring to FIG. 40, an alternative embodiment, wherein alignment may be achieved by using a plate 674 having holes 676 slightly larger than the elements 8 if the light 24 (FIGS. 2 and 4) is incident along the grating axis 207. The incident light indicated as 670 is reflected off the grating and exits through the end as a light 672 and the remaining light passes through the grating and the plate 674 as a line 678. Alternatively, if a blazed grating is used, incident light 670 may be reflected out the side of the plate (or any other desired angle), as indicated by a line 680. Alternatively, input light may be incident from the side of the plate 674 and reflected out the top of the plate 474 as indicated by a line 684. The light 672 may be a plurality of separate light beams or a single light beam that illuminates the entire tray 674 if desired.

Figure 41:
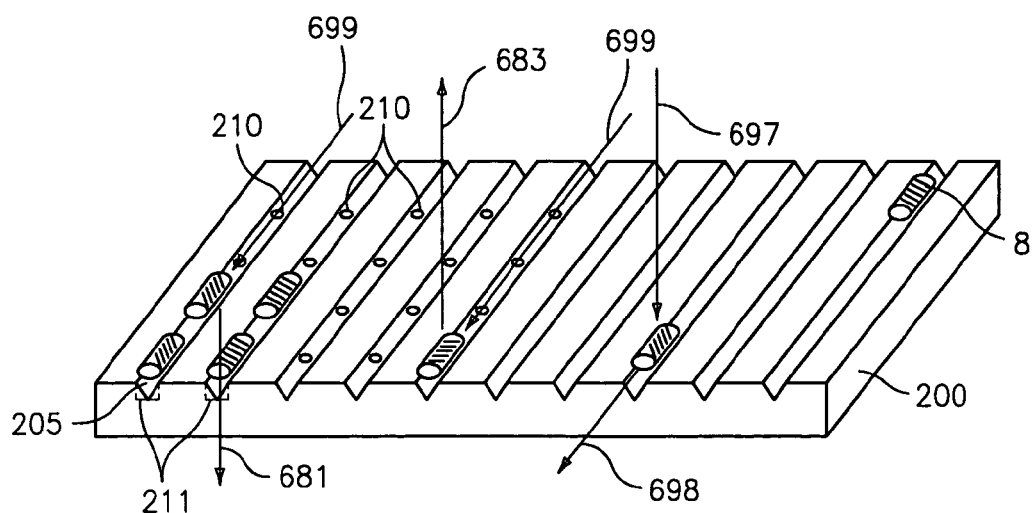
FIG. 41 is a perspective view of a grooved plate for use with an optical identification element, in accordance with the present invention.

Referring to FIG. 41, an alternative embodiment, wherein the groove plate discussed hereinbefore with FIG. 38 may be used for the end illumination/readout condition. As shown, the beads 8 are arranged in V-grooves 205, while may also take the form of square grooves generally indicated as dashed lines 211. In this case, the grating 12 may have a blaze angle such that light incident 699 along the axial grating axis will be reflected upward as reflected light 683, downward as reflected light 681, or at a predetermined angle for code detection. Similarly, the input light 697 may be incident on the grating in a downward, upward, or at a predetermined angle and the grating 12 may reflect light along the axial grating axis for code detection.

Referring to FIG. 42, regarding microbead mapper 20 readings, microbeads 8 arranged on a plate 200 having grooves 205. As shown, the microbeads 8 have different codes (e.g. "41101", "20502", "41125") using 16-bit, binary symbology), which may be read or detected using the reader or detector configuration described hereinbefore. The codes in the beads are used to provide a cross reference to determine which probe is attached to which bead, thus allowing the researcher to correlate the chemical content on each bead with the measured fluorescence signal in the process discussed herein.

Consistent with that discussed herein, the grooved plate 200 may be made of glass or plastic or any material that is transparent to the code reading incident beam 24 and code reading output light beams 27 as well as the fluorescent excitation beam 800 and the output fluorescent optical signal 802, and is properly suited for the desired application or experiment, e.g., temperature range, harsh chemicals, or other application specific requirements.

The code signal 822 from the bead code reader 820 and the fluorescent signal 810 from the fluorescence detector are provided to a known computer 812. The computer 812 reads the code associated with each bead and determines the chemical probe that was attached thereto from a predetermined table that correlates a predetermined relationship between the bead code and the attached probed. In addition, the computer 812 and reads the fluorescence associated with each bead and determines the sample or analyte that is attached to the bead from a predetermined table that correlates a predetermined relationship between the fluorescence tag and the analyte attached thereto. The computer 812 then determines information about the analyte and/or the probe as well as about the bonding of the analyte to the probe, and provides such information on a display, printout, storage medium or other interface to an operator, scientist or database for review and/or analysis, consistent with shown in step 4 of FIG. 1. The sources 801, 803 the code reader 820, the fluorescence optics 804 and detector 808 and the computer 812 may all be part of an assay stick reader 824.

Alternatively, instead of having the code excitation source 801 and the fluorescence excitation source 803, the reader 24 may have only one source beam which provides both the reflected optical signal 27 for determining the code and the fluorescence signal 802 for reading the tagged analyte attached to the beads 8. In that case the input optical signal is a common wavelength that performs both functions simultaneously, or sequentially, if desired.

The microbeads 8 may be coated with the desired probe compound, chemical, or molecule prior to being placed in the grooved plate 200. Alternatively, the beads 8 may be coated with the probe after being placed in the grooved plate 200. As discussed hereinbefore, the probe material may be an Oligo, cDNA, polymer, or any other desired probe compound, chemical, cell, or molecule for performing an assay.

The scope of the invention is not intended to be limited to using or detecting fluorescent molecule markers during the assay process. For example, embodiments of the invention are envisioned using and detection other types of molecular markers in other types of processes.

Figure 43:
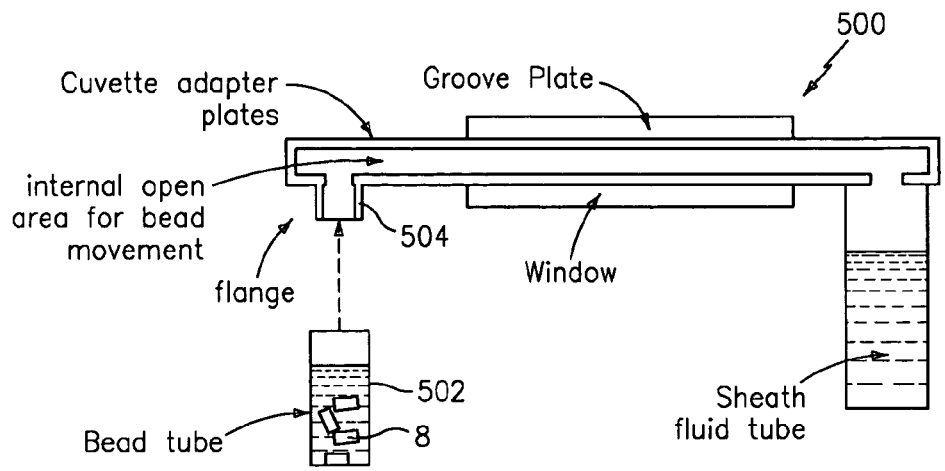
FIG. 43 is a diagram of a starting point for handling microbeads for readout in a cuvette process in accordance with the invention.

Referring to FIGS. 43-49 show the second mode which is called a closed format, that consists of not only of a groove plate but also a top and at least three walls to hold the solution and the microbeads in a cuvette-like device generally indicated as 500 shown, for example, in FIG. 43.

In summary, the closed format approach provides a method for effectively distributing and aligning microbeads during the readout process, as described below:

The basic process for handling microbeads with a curvette for readout consists of the following steps:

(1) FIG. 43 shows a starting point for handling microbeads for a readout. The microbeads start in a test tube. Typical test-tube volumes are 1.5 ml. The microbeads will generally be in a liquid (usually water with a small amount of other buffer chemicals to adjust pH and possibly a small amount [~0.01%] of detergent.) As shown, a bead tube 502 contains the microbeads in a solution, which forms part of the assay process described herein.

Figure 44:
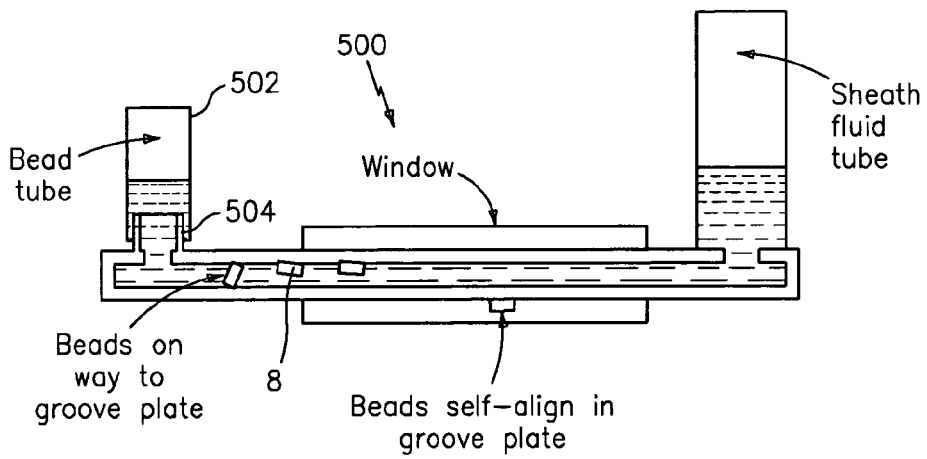
FIG. 44 is a diagram of showing beads falling into a groove plate or slide, in accordance with the invention.
Figure 47:
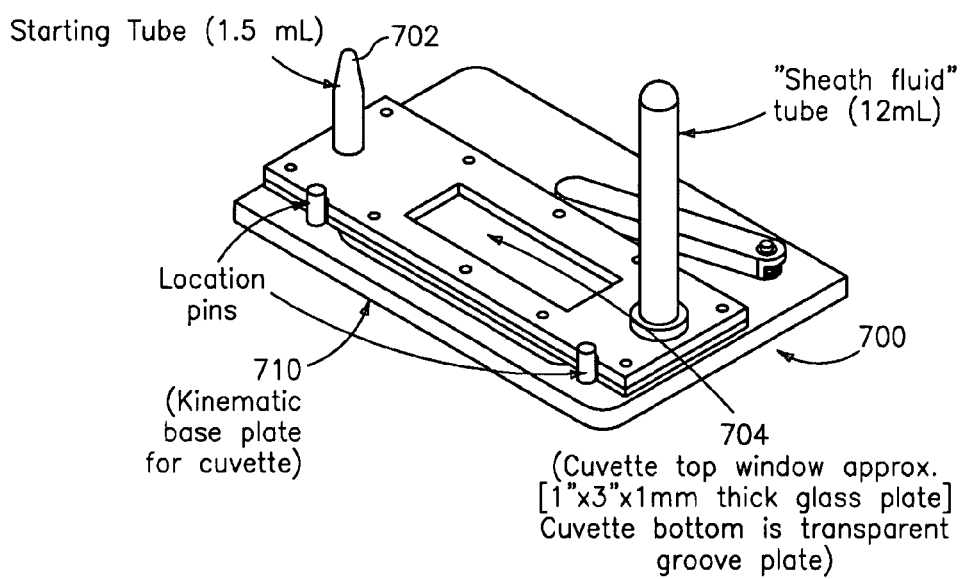
FIG. 47 is a diagram of an example of the cuvette or slide showing its mount on a kinematic plate, in accordance with the invention.

(2) FIG. 44 shows the bead tube 502 is coupled to a flange 504 of the cuvette 500 is inverted and the beads flow onto the groove plate. The cuvette consists of two round flanges that accept test-tubes, a transparent window, and an opposing groove plate. FIG. 47 shows a drawing of a prototype cuvette. The groove plate outer dimensions can be any size, but typical microscope slide dimensions are convenient (1"×3"). The grooves are mechanically or laser cut lengthwise, and have dimensions that are chosen for the exact size of cylindrical microbead. For instance, for a 125 μm diameter bead, grooves of approximately 150 μm wide by 150 μm deep are used. One tube carries the microbeads and a small amount of carrier fluid. The second tube may be larger and hold more fluid. The purpose of the second tube is to guarantee a certain fluid level in the next step.

(3) After the cuvette is inverted and the microbeads flow out onto the groove plate side of the cuvette, the microbeads naturally align in the grooves via a small amount of rocking or agitation, which forms part the assay process described herein.

(4) FIG. 45 shows the readout step, in which, after the beads are all (or nearly all) aligned in the groove plate, the entire plate is moved (or the readout laser beam is scanned) in order to read the codes of each beam, which forms part of step 3 of the assay process herein. In effect, once the microbeads are in the grooves, the entire cuvette is moved back and forth across a readout beam. The readout beam is transmitted through the cuvette and contains the code bits encoded on the scattering angles.

Figure 46:
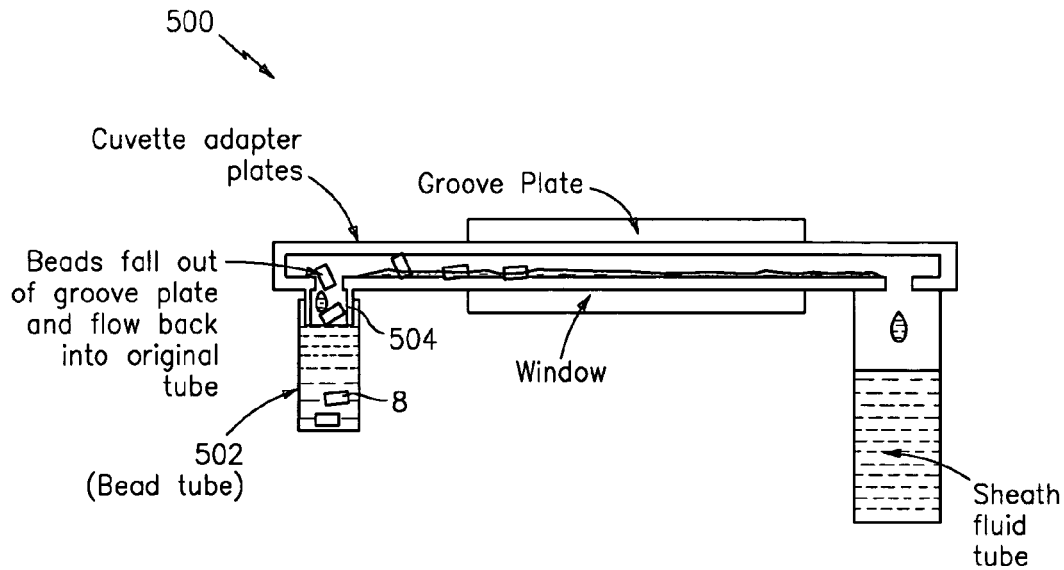
FIG. 46 is a diagram of a step of getting beads from a groove plate back into a tube after being read, in accordance with the invention.

(5) FIG. 46 shows a final step, in which the cuvette is inverted to its original position and the beads flow back into the original tube 502, which forms part of the assay process herein. In other words, after the readout process, the cuvette is re-inverted and the microbeads flow back into the original test tube.

FIG. 47 shows an example of a cuvette generally indicated as 700 that is mounted on a kinematic base plate 710. As shown, the cuvette 700 has a tube 702 for holding the solution with the beads and a top window 704 that is a 1 mm thick glass plate having dimensions of about 1" by 3". The cuvette also has a bottom plate that is a transparent groove plate. The location pins 712 and lever arm 714 hold the cuvette 700 in place on the kinematic plate 710.

One of the key advantages of using the cuvette device is that the potential to nearly index match the glass microbeads with a buffer solution thereby reducing the divergence of the laser beam caused by the lensing effect of the microbeads, and minimizing scatter form the groove plate itself.

Another advantage involves the potential to prevent microbeads from ever stacking up on top of each other, by limiting the space between the bottom and the top plate to be less than twice the diameter of the microbeads.

Another advantage is that the cover keeps the fluid from evaporating.

Figure 48:
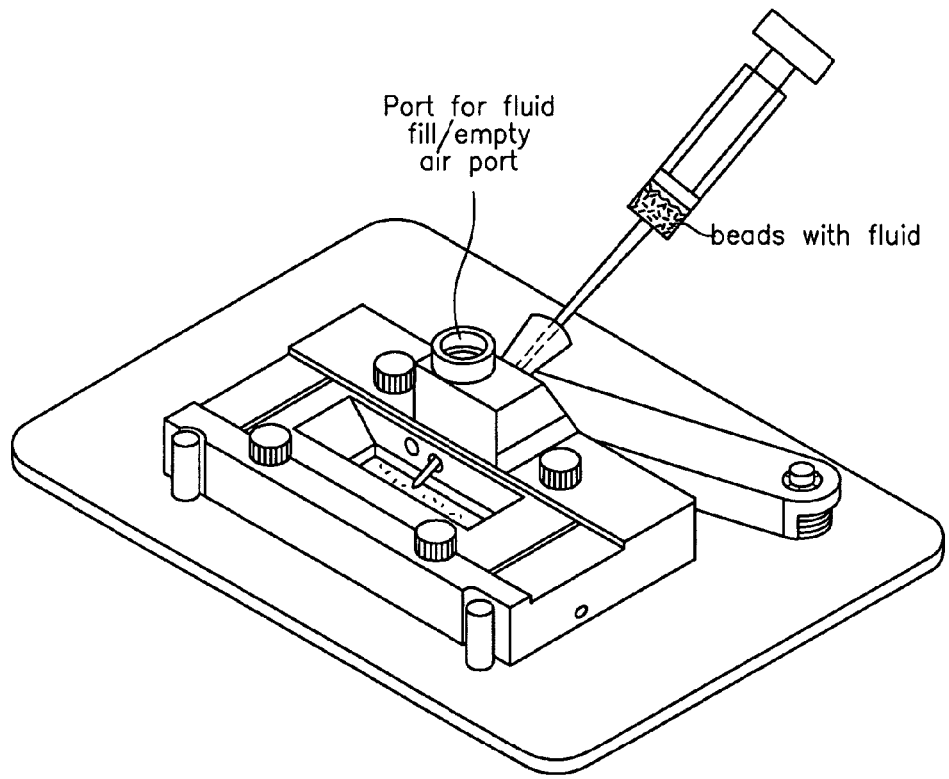
FIG. 48 is a diagram of an alternative embodiment of a cuvette showing a port for fluid filling/emptying using a pipette in accordance with the invention.
Figure 49:
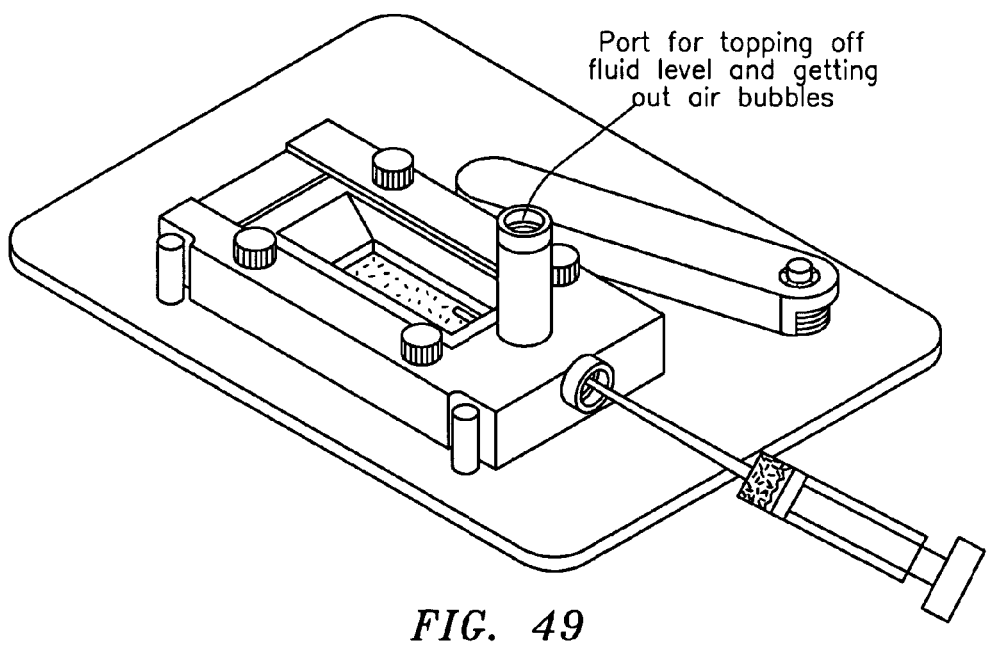
FIG. 49 is a diagram of an alternative embodiment of a cuvette showing an alternative port for fluid filling/emptying using a pipette in accordance with the invention.

FIGS. 48-49 show alternative embodiments of the cuvette shown in FIGS. 43-47. As shown, the microbeads are injected into the cuvette by placing them near the edge of the opening and allowing the surface tension, or an induced fluid flow, to pull the microbeads into the cuvette, where, because of the limited height between the floor and the ceiling of the cuvette, they are confined to move around in a plane, albeit with all the rotational degrees of freedom unconstrained. Once in the cuvette the microbeads are quickly and sufficiently constrained by the grooves as the microbeads fall into them. As in the case of the open format there is still the finite probability that some number of microbeads will not fall into the grooves and must be coaxed in by some form of agitation (ultrasonic, shaking, rocking, etc.).

An alternative embodiment of the closed approach, which involves sectioning the closed region into two regions, one where the microbeads are free to move about in a plane, either in a groove or not, and a second region where the microbeads are trapped in a groove and can only move along the axes of a groove. Trapping the microbeads in a groove is accomplished by further reducing the height of the chamber to the extent that the microbeads can no longer hop out of a groove. In this embodiment, the free region is used to pre-align the microbeads into a groove, facilitating the introduction of microbeads into the trapped section. By tilting this type of cuvette up gravity can be used to pull the microbeads along a groove from the free region to the trapped region. Once in the trapped region the microbeads move to the end of the groove where they stop. Subsequent microbeads will begin to stack up until the groove is completely full of microbeads, which are stacked head to tail. This has the advantage of packing a large number of microbeads into a small area and prevents the microbeads from ever jumping out of the grooves. This approach could also be used to align the microbeads prior to injection into some form of flow cytometer, or a dispensing apparatus.

Figures 50A, 50B, 50C:
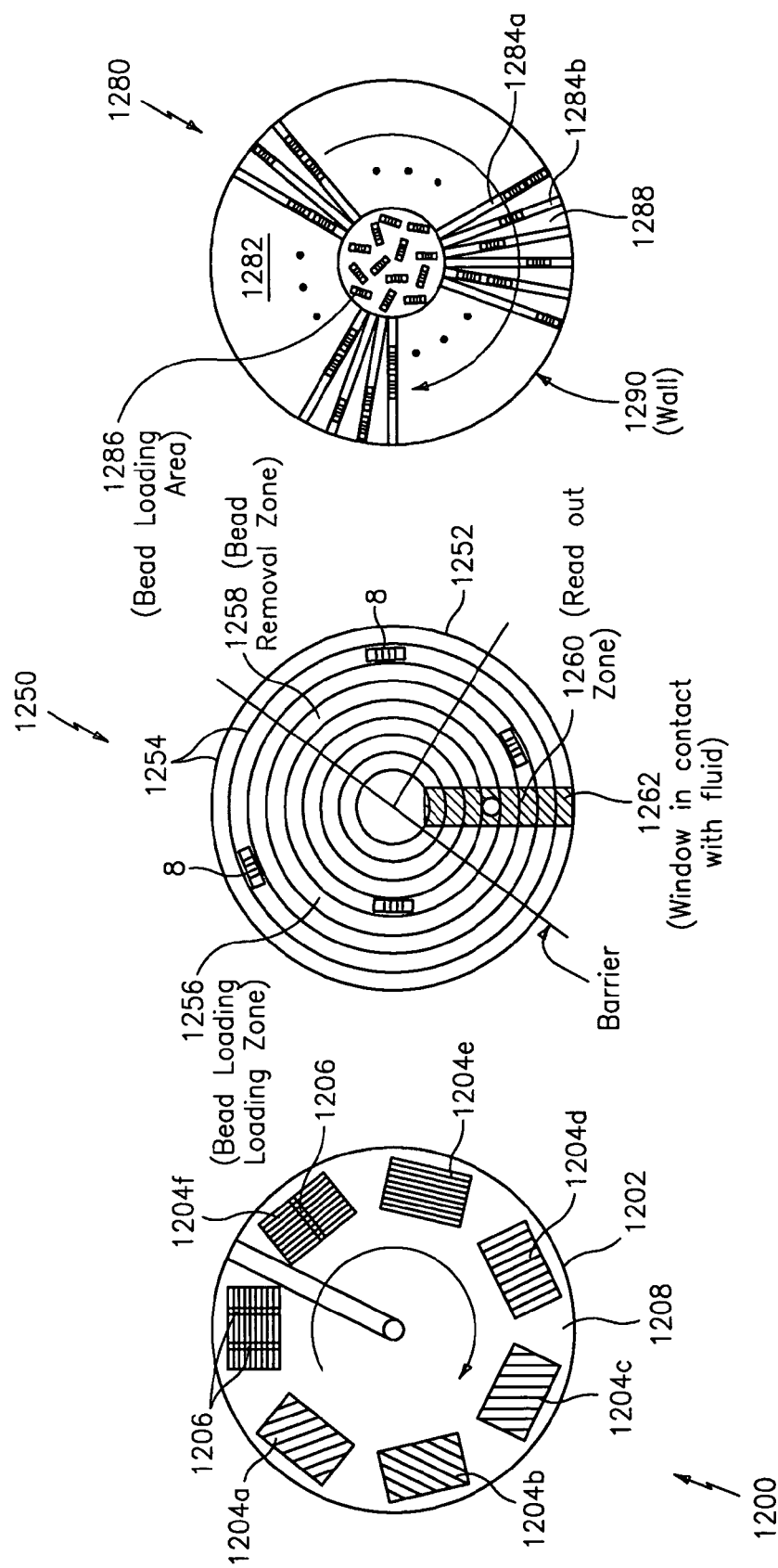
FIGS. 50(a), (b) and (c) show embodiments of a disk cytometer in accordance with the invention.

FIG. 50(a) shows an embodiment of a cytometer bead reader having a disk, which may be rotating, generally indicated as 1250, having a disk platform 1252 with circumferential, concentric, grooves 1254 for aligning microbeads 8. As shown, the rotating disk 1250 has various sectors for processing the microbeads, including a bead loading zone 1256, a bead removal zone 1258 and a readout zone 1260.

FIG. 50(b) shows an alternative embodiment of a rotating disk generally indicated as 1200, having a disk platform 1202 with planar groove plates 1204a, b, c, d, e, f that are shown with grooves oriented in any one or more different ways. One or more of the planar groove plates 1204a, b, c, d, e, f may have an optional channel 1206, 1208 for fluid run-off, as shown, and a barrier for preventing the microbeads from flying off the plate. As shown, the window 1262 for reading the beads is in contact with the fluid containing the beads.

FIG. 50(c) shows an alternative embodiment of a rotating disk generally indicated as 1280, having a disk platform 1282 with radial grooves 1284a, 1284b. The disk platform 1282 has a bead loading zone 1286 in the center of the disk. One advantage of this embodiment is that the opening of the bead loading zone 1286 will also serve to allow the release of air bubbles that will naturally collect in the center of the disk due the reduced density of the fluid, which results from the centrifugal force pushing the fluid radially outwardly. The rotating disk 1280 has tight bead packing due to the centrifugal forces due to the spinning action of the disk. The rotating disk 1280 has a wedge shape spacer 1288 that keeps the channel at a constant gap width and a wall 1290.

FIG. 51(a) shows an alternative embodiment of a rotating disk generally indicated as 1300 having narrow radial channels 1302 for spin drying so liquid is forced out of the circumferential grooves through the radial channels. The plate 1300 may have a mechanical catcher 1320 coupled thereto for moving radially outwardly in direction 1320a if desired, for recirculating loose beads.

FIG. 51(b) show an alternative embodiment of a disk cytometer 1400 having a mechanical iris 1402 for providing a variable aperture for bead access to grooves in accordance with the invention.

The dimensions and geometries for any of the embodiments described herein are merely for illustrative purposes and, as such, any other dimensions may be used if desired, depending on the application, size, performance, manufacturing requirements, or other factors, in view of the teachings herein.

It should be understood that, unless stated otherwise herein, any of the features, characteristics, alternatives or modifications described regarding a particular embodiment herein may also be applied, used, or incorporated with any other embodiment described herein. Also, the drawings herein are not drawn to scale.

Although the invention has been described and illustrated with respect to exemplary embodiments thereof, the foregoing and various other additions and omissions may be made therein and thereto without departing from the spirit and scope of the present invention.

What is claimed is:

1. A method of identifying an analyte, the method comprising:
providing a plurality of microparticles, the microparticles having elongated bodies with optically detectable codes extending along the bodies of the corresponding microparticles, the microparticles having chemical probes attached thereto, each of the chemical probes being associated with a corresponding one of the codes;
selectively binding target analytes to the chemical probes on the microparticles to produce labeled microparticles;
distributing the labeled microparticles to random locations of a substrate, thereby providing a random array of labeled microparticles;
determining the codes for the labeled microparticles in the random array and code positions of the codes in the random array;
detecting labels on the labeled microparticles in the random array and label positions of the labels in the random array; and
using the code positions and the label positions to analyze the target analytes.

2. The method of claim 1, wherein the chemical probes and the target analytes comprise nucleic acids.

3. The method of claim 2, wherein the method comprises determining a genotype.

4. The method of claim 2, wherein the method comprises gene expression analysis.

5. The method of claim 1, wherein the code determining and label detecting operations are conducted in an automated manner.

6. The method of claim 1, wherein the labels are fluorescent labels and the label detecting operation includes capturing at least one image of fluorescent optical output emanating from the microparticles on the substrate.

7. The method of claim 1, wherein the code determining operation includes capturing at least one image of an optical output indicative of the codes for the microparticles.

8. The method of claim 7, wherein the optical output includes one of light reflected by the codes and light transmitted through the codes.

9. The method of claim 1, wherein the distributing the labeled microparticles onto the substrate includes flowing the microparticles onto the substrate within a solution, the microparticles falling onto the substrate in a random distribution.

10. The method of claim 9, wherein the code determining operation includes illuminating the microparticles on the substrate while submerged within the solution.

11. The method of claim 10, wherein the microparticles comprise a material having a refractive index and the solution has a refractive index, the material of the microparticles and the solution being substantially index-matched.

12. The method of claim 1, wherein the code determining operation includes illuminating the particles with an incident light, the incident light being substantially perpendicular to a plane of the substrate.

13. The method of claim 1, wherein the substrate is a two-dimensional substrate, the microparticles being arranged co-planar with each other.

14. The method of claim 1, wherein the substrate includes a plurality of grooves, the method further comprising orienting the elongated bodies of the microparticles within the grooves, the microparticles being randomly distributed within the grooves.

15. The method of claim 1, wherein the microparticles are rectangular and have a substantially square cross-sectional shape.

16. The method of claim 1, wherein the microparticles have an inner region and an outer region that surrounds the inner region, the inner region extending along a longitudinal axis of the microparticles and being located at a center of the microparticles, the code being within the inner region.

17. The method of claim 1, wherein the code is completely surrounded by a transparent material and extends along a longitudinal axis of the microparticle such that the code is determinable from any direction about the longitudinal axis.

18. The method of claim 1, wherein the code comprises a grating having a periodic or aperiodic variation in at least one of a refractive index and an optical absorption of at least a portion of the microparticle.

19. The method of claim 1, wherein the code is one of written, impressed, embedded, imprinted, etched, grown, and deposited within the microparticle.

20. A method of nucleic acid analysis, the method comprising:
providing a plurality of microparticles, the microparticles having elongated bodies with optically detectable codes extending along the bodies of the corresponding microparticles, the microparticles having nucleic acid probes attached thereto, each of the nucleic acid probes being associated with a corresponding one of the codes;
hybridizing target nucleic acids to complementary nucleic acid probes on the microparticles to produce labeled microparticles;
distributing the labeled microparticles to random locations of a substrate, thereby providing a random array of labeled microparticles;
determining the codes for the labeled microparticles in the random array and code positions of the codes in the random array;
detecting labels on the labeled microparticles in the random array and label positions of the labels in the random array; and
using the code positions and the label positions to analyze the target nucleic acids.

21. The method of claim 20, wherein the method comprises determining a genotype.

22. The method of claim 20, wherein the method comprises gene expression analysis.

23. The method of claim 20, wherein the code determining and label detecting operations are conducted in an automated manner.

24. The method of claim 20, wherein the labels are fluorescent labels and the label detecting operation includes capturing at least one image of fluorescent optical output emanating from the microparticles on the substrate.

25. The method of claim 20, wherein the code determining operation includes capturing at least one image of an optical output indicative of the codes for the microparticles.

26. The method of claim 25, wherein the optical output includes one of light reflected by the codes and light transmitted through the codes.

27. The method of claim 20, wherein the distributing the labeled microparticles onto the substrate includes flowing the microparticles onto the substrate within a solution, the microparticles falling onto the substrate in a random distribution.

28. The method of claim 20, wherein the code determining operation includes illuminating the microparticles on the substrate while submerged within a solution.

29. The method of claim 28, wherein the microparticles comprise a material having a refractive index and the solution has a refractive index, the material of the microparticles and the solution being substantially index-matched.

30. The method of claim 20, wherein the code determining operation includes illuminating the particles with an incident light, the incident light being substantially perpendicular to a plane of the substrate.

31. The method of claim 20, wherein the substrate is a two-dimensional substrate, the microparticles being arranged co-planar with each other.

32. The method of claim 20, wherein the substrate includes a plurality of grooves, the method further comprising orienting the elongated bodies of the microparticles within the grooves, the microparticles being randomly distributed within the grooves.

33. The method of claim 20, wherein the microparticles are rectangular and have a substantially square cross-sectional shape.

34. The method of claim 20, wherein the microparticles have an inner region and an outer region that surrounds the inner region, the inner region extending along a longitudinal axis of the microparticles and being located at a center of the microparticles, the code being within the inner region.

35. The method of claim 20, wherein the code is completely surrounded by a transparent material and extends along a longitudinal axis of the microparticle such that the code is determinable from any direction about the longitudinal axis.

36. The method of claim 20, wherein the code comprises a grating having a periodic or aperiodic variation in at least one of a refractive index and an optical absorption of at least a portion of the microparticle.

37. The method of claim 20, wherein the code is one of written, impressed, embedded, imprinted, etched, grown, and deposited within the microparticle.

38. The method of claim 20, further comprising determining the labels and determining the label positions.

39. The method of claim 20, wherein the code determining and label detecting operations comprise:
(a) the determining the codes for the labeled microparticles in the random array;
(b) the determining the code positions of the codes in the random array;
(c) the detecting labels on the labeled microparticles in the random array; and
(d) the detecting label positions of the labels in the random array;
and wherein the operations of (a)-(d) occur in any order or simultaneously.

40. The method of claim 20, wherein the label detecting operation includes capturing at least one image of the labeled microparticles in the random positions on the substrate.

41. The method of claim 20 further comprising capturing at least one image of the labeled microparticles in the random positions on the substrate, wherein the at least one image is utilized during at least one of the code determining and label detecting operations.

42. The method of claim 20, wherein the target nucleic acids include nucleic acids of a common sequence.

43. The method of claim 20, wherein the target nucleic acids include at least first and second types of target nucleic acids, the first and second types of target nucleic acids having different nucleic acid sequences, the labels including at least first and second labels, the first and second labels being different and being associated with the first and second types of target nucleic acids, respectively.

44. The method of claim 1, further comprising determining the labels and determining the label positions.

45. The method of claim 1, wherein the code determining and label detecting operations comprise:
   (a) the determining the codes for the labeled microparticles in the random array;
   (b) the determining the code positions of the codes in the random array;
   (c) the detecting labels on the labeled microparticles in the random array; and
   (d) the detecting label positions of the labels in the random array;
   and wherein the operations of (a)-(d) occur in any order or simultaneously.

46. The method of claim 1, wherein the label detecting operation includes capturing at least one image of the labeled microparticles in the random positions on the substrate.

47. The method of claim 1 further comprising capturing at least one image of the labeled microparticles in the random positions on the substrate, wherein the at least one image is utilized during at least one of the code determining and label detecting operations.

48. The method of claim 1, wherein the target analytes include one type of target analyte.

49. The method of claim 1, wherein the target analytes include at least first and second types of target analytes, the first and second types of target analytes having different chemical structures, the labels including at least first and second labels, the first and second labels being different and being associated with the first and second types of target analytes, respectively.

* * * * *